(12) United States Patent
Fan et al.

(10) Patent No.: US 10,274,486 B2
(45) Date of Patent: *Apr. 30, 2019

(54) SYSTEM, DEVICE AND METHOD FOR HIGH-THROUGHPUT MULTI-PLEXED DETECTION

(71) Applicant: Yale University, New Haven, CT (US)

(72) Inventors: Rong Fan, Cheshire, CT (US); Yao Lu, New Haven, CT (US); Jonathan Chen, San Jose, CA (US)

(73) Assignee: Yale University, New Haven, CT (US)

( * ) Notice: Subject to any disclaimer, the term of this patent is extended or adjusted under 35 U.S.C. 154(b) by 132 days.

This patent is subject to a terminal disclaimer.

(21) Appl. No.: 15/290,874

(22) Filed: Oct. 11, 2016

(65) Prior Publication Data

US 2017/0067887 A1 Mar. 9, 2017

Related U.S. Application Data

(63) Continuation of application No. 14/629,164, filed on Feb. 23, 2015, now Pat. No. 9,506,917, which is a continuation of application No. 14/562,061, filed on Dec. 5, 2014, now Pat. No. 9,188,586, which is a (Continued)

(51) Int. Cl.
*G01N 33/543* (2006.01)

(52) U.S. Cl.
CPC . *G01N 33/54366* (2013.01); *G01N 33/54306* (2013.01); *G01N 33/54386* (2013.01); *G01N 2570/00* (2013.01); *G01N 2800/7028* (2013.01)

(58) Field of Classification Search
None
See application file for complete search history.

(56) References Cited

U.S. PATENT DOCUMENTS

| 6,377,721 B1 | 4/2002 | Walt et al. |
| 6,429,027 B1 | 8/2002 | Chee et al. |
| 6,699,665 B1 | 3/2004 | Kim et al. |

(Continued)

FOREIGN PATENT DOCUMENTS

| WO | WO 96/28538 A1 | 9/1996 |
| WO | WO 2007/035633 A2 | 3/2007 |
| WO | WO 2010/065929 A2 | 6/2010 |

OTHER PUBLICATIONS

Adams et al., Multitarget magnetic activated cell sorter. Proc Natl Acad Sci USA. 2008;105(47):18165-18170. doi:10.1073/pnas.0809795105.

(Continued)

*Primary Examiner* — Changhwa J Cheu
(74) *Attorney, Agent, or Firm* — Wolf, Greenfield & Sacks, P.C.

(57) ABSTRACT

The present invention relates to a system, device, and method for the high throughput multiplexed detection of a wide number of compounds. The invention comprises of a microwell array coupled to a capture agent array to form a plurality of interfaces between a microwell and a set of immobilized capture agents. The set of capture agents comprises a plurality of distinguishable features, with each feature corresponding to the detection of a particular compound of interest. In certain embodiments, each microwell is configured to contain a single cell. The invention is therefore capable of performing a high throughput analysis of single cell profiles, including profiles of secreted compounds.

17 Claims, 85 Drawing Sheets

Related U.S. Application Data continuation of application No. PCT/US2013/056454, filed on Aug. 23, 2013.

(60) Provisional application No. 61/779,299, filed on Mar. 13, 2013, provisional application No. 61/692,895, filed on Aug. 24, 2012.

(56) References Cited

U.S. PATENT DOCUMENTS

| | | | |
|---|---|---|---|
| 7,381,375 | B2 | 6/2008 | Ravkin et al. |
| 8,460,878 | B2 | 6/2013 | Walt et al. |
| 9,188,586 | B2 | 11/2015 | Fan et al. |
| 9,506,917 | B2 | 11/2016 | Fan et al. |
| 2009/0137413 | A1 | 5/2009 | Burd et al. |
| 2010/0152054 | A1 | 6/2010 | Love et al. |
| 2015/0204862 | A1 | 7/2015 | Fan et al. |

OTHER PUBLICATIONS

Amir et al., viSNE enables visualization of high dimensional single-cell data and reveals phenotypic heterogeneity of leukemia. Nat Biotechnol. Jun. 2013;31(6):545-52. doi: 10.1038/nbt.2594. Epub May 19, 2013.

Balaban et al., Bacterial persistence as a phenotypic switch. Science. Sep. 10, 2004;305(5690):1622-5. Epub Aug. 12, 2004.

Bendall et al., From single cells to deep phenotypes in cancer. Nat Biotechnol. Jul. 10, 2012;30(7):639-47. doi: 10.1038/nbt.2283. Review.

Bendall et al., Single-cell mass cytometry of differential immune and drug responses across a human hematopoietic continuum. Science. May 6, 2011;332(6030):687-96. doi: 10.1126/science.1198704.

Chen et al., Multiplexed analysis of glycan variation on native proteins captured by antibody microarrays. Nat Methods. May 2007;4(5):437-44. Epub Apr. 8, 2007.

Cheong et al., Using a microfluidic device for high-content analysis of cell signaling. Sci Signal. Jun. 16, 2009;2(75):p12. doi:10.1126/scisignal.275p12. Review.

Choi et al., Immuno-hybridization chain reaction for enhancing detection of individual cytokine-secreting human peripheral mononuclear cells. Anal Chem. Sep. 1, 2011;83(17):6890-5. doi: 10.1021/ac2013916. Epub Aug. 15, 2011.

Fan et al., Integrated blood barcode chips. Nat Biotechnol. Dec. 2008;26(12):1373-8. doi: 10.1038/nbt.1507. Epub Nov. 16, 2008.

Han et al., Multidimensional analysis of the frequencies and rates of cytokine secretion from single cells by quantitative microengraving. Lab Chip. Jun. 7, 2010;10(11):1391-400. doi:10.1039/b926849a. Epub Apr. 8, 2010.

Han et al., Polyfunctional responses by human T cells result from sequential release of cytokines. Proc Natl Acad Sci U S A. Jan. 31, 2012;109(5):1607-12. doi: 10.1073/pnas.1117194109. Epub Dec. 12, 2011.

Henshall et al., Assay: Validating biomarkers with VeraCode. Genet Eng Biotechnol News. Oct. 2007;27(17):1-3.

Lecault et al., High-throughput analysis of single hematopoietic stem cell proliferation in microfluidic cell culture arrays. Nat Methods. May 22, 2011;8(7):581-6. doi: 10.1038/nmeth.1614.

Lee et al., Quantitative and dynamic assay of single cell chemotaxis. Integr Biol (Camb). Apr. 2012;4(4):381-90. doi: 10.1039/c2ib00144f. Epub Jan. 9, 2012.

Liotta et al., Protein microarrays: meeting analytical challenges for clinical applications. Cancer Cell. Apr. 2003;3(4):317-25. Review.

Love et al., A microengraving method for rapid selection of single cells producing antigen-specific antibodies. Nat Biotechnol. Jun. 2006;24(6):703-7. Epub May 14, 2006.

Ma et al., A clinical microchip for evaluation of single immune cells reveals high functional heterogeneity in phenotypically similar T cells. Nat Med. Jun. 2011;17(6):738-43. doi: 10.1038/nm.2375. Epub May 22, 2011.

Michor et al., the origins and implications of intratumor heterogeneity. Cancer Prey Res (Phila). Nov. 2010;3(11):1361-4. doi:10.1158/1940-6207.CAPR-10-0234. Epub Oct. 19, 2010.

Rowat et al., Tracking lineages of single cells in lines using a microfluidic device. Proc Natl Acad Sci U S A. Oct. 27, 2009;106(43):18149-54. doi: 10.1073/pnas.0903163106. Epub Oct. 13, 2009.

Sachdeva et al., Cytokine quantitation: technologies and applications. Front Biosci. May 1, 2007;12:4682-95. Review.

Shin et al., Protein signaling networks from single cell fluctuations and information theory profiling. Biophys J. May 18, 2011;100(10):2378-86. doi:10.1016/j.bpj.2011.04.025.

Unger et al., Monolithic microfabricated valves and pumps by multilayer soft lithography. Science. Apr. 7, 2000;288(5463):113-6.

Wang et al., Single cell analysis: the new frontier in 'omics'. Trends Biotechnol. Jun. 2010;28(6):281-90. doi: 10.1016/j.tibtech.2010.03.002. Epub Apr. 29, 2010. Review.

Wei et al., Microchip platforms for multiplex single-cell functional proteomics with applications to immunology and cancer research. Genome Med. Aug. 29, 2013;5(8):75. doi: 10.1186/gm479. eCollection 2013. Review.

Yang et al., Using a cross-flow microfluidic chip and external crosslinking reaction for monodisperse TPP-chitosan microparticles. Sensors and Acuators. 2007;124:510-6.

[No Author Listed], The Power of Human. Enumeral. Retrieved from http://www.enumeral.com. Accessed Feb. 8, 2018. 2 pages.

[No Author Listed], Isoplexis. Retrieved from http://isoplexis.com. Accessed Jun. 30, 2014. 1 page.

Green et al., Capturing the uncultivated majority. Current Opinion in Biotechnology 17 (3), 2006, 250-255.

Hughes, A. et al. Single-cell western blotting. Nat Methods. Jul. 2014;11(7):749-55.

Kwak, M. et al. Single-cell protein secretomic signatures as potential correlates to tumor cell lineage evolution and cell-cell interaction. Frontiers in Oncology 3, Feb. 2013, Art. 10, 1-8.

Lu, Y. et al. High-throughput secretomic analysis of single cells to assess functional cellular heterogeneity. Analytic Chemistry 85 (4) Feb. 2013, 2548-2556.

Shi et al., Single-cell proteomic chip for profiling intracellular signaling pathways in single tumor cells. Proc Natl Acad Sci U S A. Jan. 10, 2012;109(2):419-24. doi: 10.1073/pnas.1110865109. Epub Dec. 27, 2011.

Shin et al., Chemistries for patterning robust DNA microbarcodes enable multiplex assays of cytoplasm proteins from single cancer cells. Chemphyschem. Oct. 4, 2010;11(14):3063-9. doi: 10.1002/cphc.201000528.

Zhang, K. et al. Sequencing genomes from single cells by polymerase cloning. Nature Biotechnology 24 (6), Jun. 2006, 680-686.

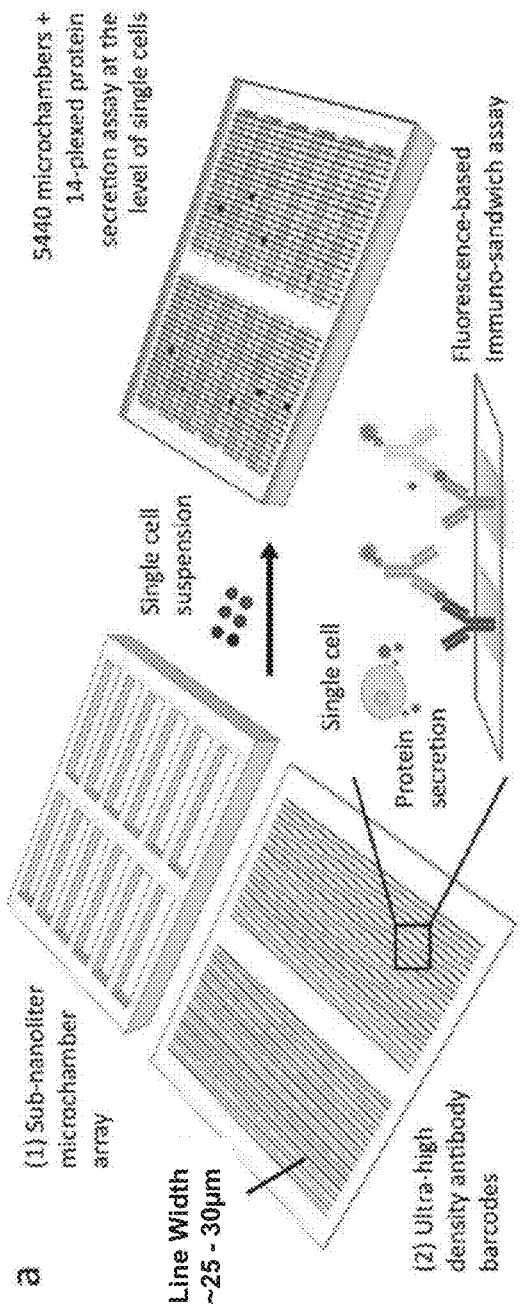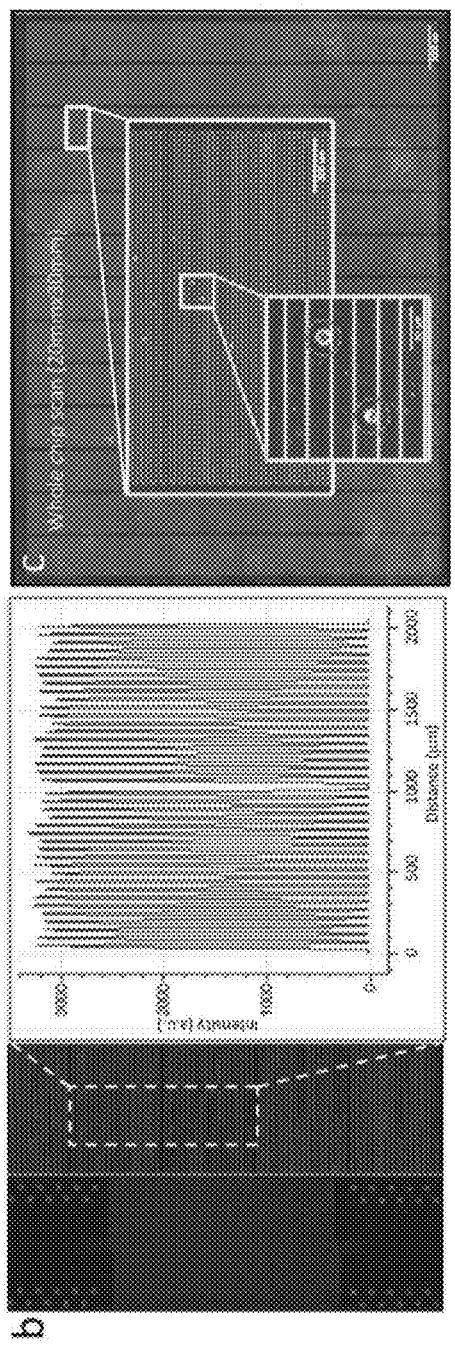
Figures 1A-1C

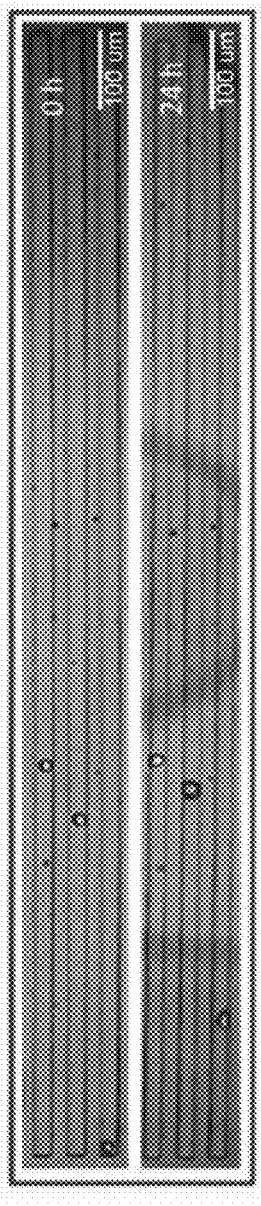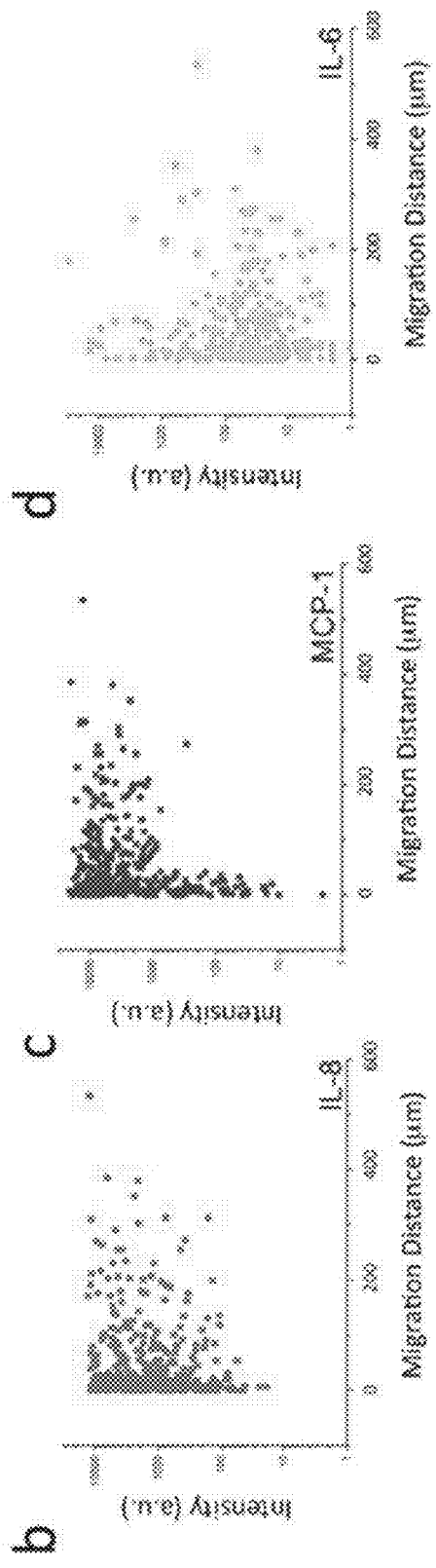
Figures 4A-4D

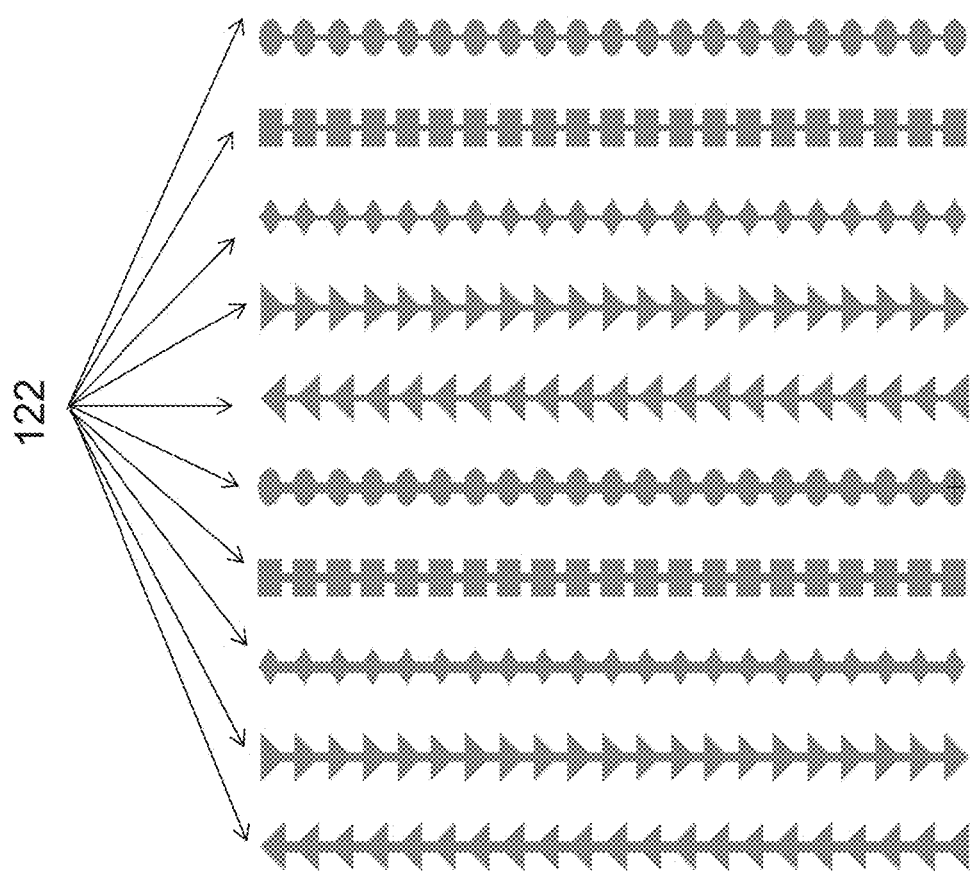

Figure 30

| | 488 color | 532 color | Biotin group 635 color |
|---|---|---|---|
| 1 | IL-1a | IL-17A | IL-2 |
| 2 | IL-1b | MCP-1 | MIP-1a |
| 3 | IL-3 | Rantes | TGF-a |
| 4 | IL-4 | TNF-a | TGF-b |
| 5 | IL-5 | TNF-b | G-CSF |
| 6 | IL-6 | IL-22 | IFN-g |
| 7 | IL-7 | MIP-1b | GMCSF |
| 8 | IL-8 | SCF | IL-9 |
| 9 | IL-10 | M-CSF | IL-23 |
| 10 | IL-12 | EGF | MMP-2 |
| 11 | IL-13 | HGF | MMP-9 |
| 12 | IL-15 | NGF-b | IL-27 |
| 13 | IL-1RA | PDGF | IL-29 |
| 14 | MIF | VEGF | TSLP |
| 15 | 488-BSA | 532-BSA | 635-BSA |

| | MIF | | IL-1b | | IL-4 | | GMCSF | |
|---|---|---|---|---|---|---|---|---|
| ICS Control-LPS | 99% | 99.7% | 92.8% | 97.4% | 63.9% | 66.8% | 6.5% | 44.5% |
| SCMA Control-LPS | 32.4% | 33.2% | 12.9% | 11.9% | 2.5% | 0.8% | 30.4% | 46.4% |

| | IL-8 | | IL-13 | | MIP-1a | | MIP-1b | |
|---|---|---|---|---|---|---|---|---|
| ICS Control-LPS | 18.2% | 90.4% | 3.7% | 2.5% | 99% | 99.7% | 29.3% | 99.4% |
| SCMA Control-LPS | 28.8% | 54.7% | 0% | 2.5% | 23.5% | 40.2% | 14.9% | 41.3% |

| | Rantes | | G-CSF | | MCP-1 | | TNF-a | |
|---|---|---|---|---|---|---|---|---|
| ICS Control-LPS | 12.6% | 20.3% | 66.6% | 50.7% | 98.6% | 99.7% | 0% | 7.1% |
| SCMA Control-LPS | 64.1% | 62.5% | 7% | 3.1% | 61.8% | 53.8% | 3.7% | 15.1% |

| | TNF-b | | EGF | | IL-6 | | IL-10 | |
|---|---|---|---|---|---|---|---|---|
| ICS Control-LPS | 0% | 0.4% | 95.1% | 92.6% | 89.3% | 78.8% | 17.9% | 41.2% |
| SCMA Control-LPS | 0% | 0.5% | 0% | 1.2% | 2.1% | 14.3% | 4.9% | 16.7% |

*Threshold definition:*
*0 cell average + 2sd*

Figure 40

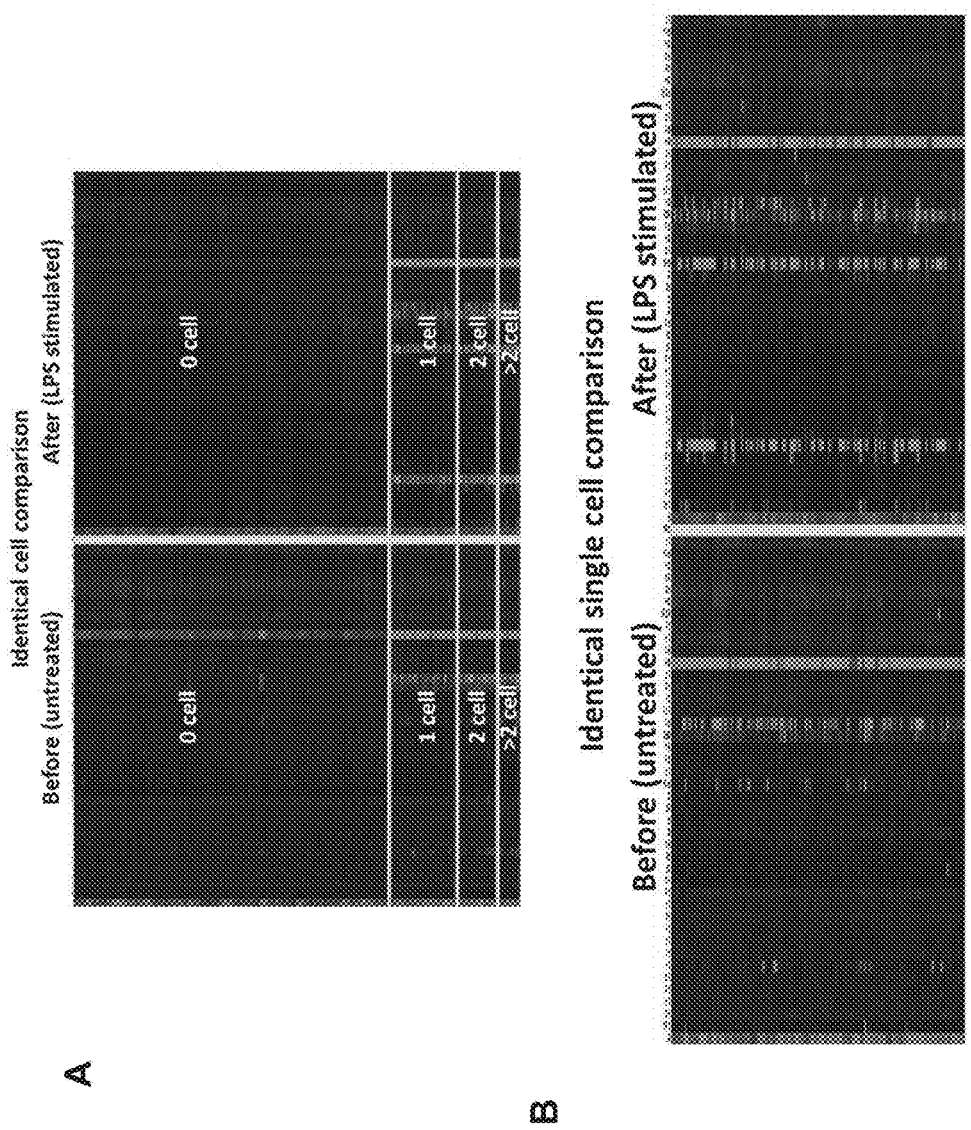
Figures 56A-B

| Single-Cell Functional Proteomics Tools | Mass Cytometry | IsoPlexis Microchip Device |
|---|---|---|
| Multiplexing | 42-plex, expandable | 45-plex, expandable |
| Proteins | Surface protein, intra-cellular proteins, "secreted" proteins | Secreted proteins (can be extended to surface and intracellular proteins) |
| Throughput | High ($10^6$ cells per run) | Low (~1000 per run) |
| Cost | High (>$1M), require staffing and run with the core facility | Low (<$10K), even for point of care applications |
| Sample Consumption | Large (excellent statistic power) | Small (very useful when the sample size is limited) |
| Live cell recoverable | No (all cells burned in ICP) | Yes (secreted proteins); No (intracellular proteins) |
| | Complementary to each other | |

Figure 57

SYSTEM, DEVICE AND METHOD FOR HIGH-THROUGHPUT MULTI-PLEXED DETECTION

CROSS-REFERENCE TO RELATED APPLICATIONS

This application is a continuation of U.S. application Ser. No. 14/629,164, filed Feb. 23, 2015, which is a continuation of U.S. application Ser. No. 14/562,061, filed Dec. 5, 2014, which is a continuation of international application number PCT/US2013/056454, filed Aug. 23, 2013, which claims the benefit under 35 U.S.C. § 119(e) of U.S. provisional application No. 61/692,895, filed Aug. 24, 2012, and of U.S. provisional application No. 61/779,299, filed Mar. 13, 2013, each of which is herein incorporated by reference in its entirety.

STATEMENT REGARDING FEDERALLY-SPONSORED RESEARCH OR DEVELOPMENT

This invention was made with government support under NIH UO1 CA164252, NIH 4R00 CA136759, NIH U54CA143868, NIH RO1 GM084201, and NIH U54 CA143798, awarded by the National Institutes of Health (NIH). The government has certain rights in the invention.

BACKGROUND OF THE INVENTION

Secreted proteins including cytokines, chemokines, and growth factors represent important functional regulators mediating a range of cellular behavior and cell-cell paracrine/autocrine signaling, e.g., in the immunological system (Rothenberg, 2007, Nat. Immunol 8(5):441-4), tumor microenvironment (Hanahan and Weinberg, 2011, Cell 144 (5):646-74), or stem cell niche (Gnecchi et al., 2008, Circ. Res 103(1):1204-19). Detection of these proteins is of great value not only in basic cell biology but also for disease diagnosis and therapeutic monitoring. However, because of coproduction of multiple effector proteins from a single cell, referred to as polyfunctionality, it is biologically informative to measure a panel of secreted proteins, or secretomic signature, at the level of single cells. Recent evidence further indicates that a genetically identical cell population can give rise to diverse phenotypic differences (Niepel et al., 2009, Curr Opin Chem Biol 13(5-6):556-561). Nongenetic heterogeneity is also emerging as a potential barrier to accurate monitoring of cellular immunity and effective pharmacological therapies (Gascoigne and Taylor, 2008, Cancer Cell 14(2):111-22; Cohen et al., 2008, Science 322(5907):1511-6), suggesting the need for practical tools for single cell analysis of proteomic signatures.

Fluorescence-activated cell sorting (FACS) represents the state-of-the-art for single cell analysis (Sachs et al., 2005, Science 308(5721):523-9). FACS is typically used to detect and sort cell phenotypes by their surface markers. It has been extended to the detection of intracellular proteins (Sachs et al., 2005, Science 308(5721):523-9; Kotecha et al., 2008, Cancer Cell 14(4):335-43; Irish et al., 2004, Cell 118(2): 217-28), including cytokines within the cytoplasm, by blocking vesicle transport (Prussin, 1997, Clin Immunol 17(3):195-204). However, intracellular cytokine staining (ICS) is not a true secretion analysis, and it also requires cell fixing, which means the cells are no longer alive after flow cytometric analysis and cannot be recovered for further studies. A further disadvantage to ICS is the spectral overlap and the possibility of non-specific binding of intracellular staining antibodies, which will ultimately prevent accurate multiplexing over the current capability of 12-plexing. The mainstay of real single cell secretion analysis to date is a simple approach called ELISpot, a plate based cell culture assay using standard ELISA detection, which detects the secretion footprint of individual cells using an immunosandwich-based assay (Sachdeva and Asthana, 2007, Front Biosci 12:4682-95). Immune cells are loaded into a microtiter plate that has been precoated with a layer of primary antibody. After incubation, secreted proteins are captured by the antibodies located proximal to the cells, giving rise to spots indicative of a single cell secretion footprint (Stratov et al., 2004, Curr Drug Targets 5(1):71-88). Recently, a variant of ELISpot, called FLUOROSpot, which exploits two fluorescent dyes to visualize protein secretion footprints, enabled a simultaneous dual function analysis, though this technique is limited to low multiplexing capabilities. Highly multiplexed measurements of proteins secreted from a population of cells can be done using an encoded bead assay such as the Illumina VeraCode system (Henshall and Gorfain, 2007, Genet Eng Biotechnol News 27(17): 1) or antibody microarrays manufactured using a pin-spotting technique (Chen et al., 2007, Nat Methods 4(5):437-44; Liotta et al., 2003, Cancer Cell 3(4):317-25). However, these highly multiplexed technologies cannot perform single cell measurements. Microfabricated chips have emerged as a new category of single cell analytic technologies (Wang and Bodovitz, 2010, Trends Biotechnol 28(6): 281-90; Cheong et al., 2009, Sci Signal 2(75):p 12; Love et al., 2006, Nat Biotechnol 24(6):703-7; Lee et al., 2012, Integr Biol (Camb) 4(4):381-90; Rowat et al., 2009, Proc Natl Acad Sci USA 106(43):18149-54; Lecault et al., 2011, Nat. Methods 8(7):581-6). A prototype microchip has demonstrated the feasibility of the multiplexed protein secretion assay and revealed significant polyfunctional heterogeneity in phenotypically similar immune cells from patients (Shin et al., 2011, Biophys J 100(10):2378-86; Ma et al., 2011, Nat Med 17(6):738-43), pointing to the urgent need for single cell secretion profiling in clinical diagnosis and therapeutic monitoring. However, these microchips either lack sufficient throughput or multiplicity or require sophisticated operation, precluding widespread application in cell biology and clinical evaluation of cellular functions. These technologies cannot perform highly multiplexed protein analysis on single cells. For example, thus far there is no technology available to perform high-content (>1000 cells) and highly multiplexed (>35 proteins) measurement of secreted proteins at the single cell level.

Thus, there is a need in the art for a device and method for multiplex analysis of a wide number of compounds from single cells. The present invention satisfies this unmet need.

SUMMARY OF THE INVENTION

The present invention includes a device for the multiplexed detection of a plurality of compounds from single cells comprising a microwell array and a capture agent array. The microwell array comprises a plurality of individual microwells in uniform arrangement, at least some of the plurality of individual microwells having a length of greater than 50 µm and configured to contain an isolated single cell in a sub-nanoliter volume of contents. The capture agent array comprises a plurality of immobilized capture agents, each immobilized capture agent capable of specifically binding to one of the plurality of compounds. The immobilized capture agents are arranged in uniform capture agent sets, where each capture agent set comprises a plurality of isolated features at spatially identifiable locations, each isolated feature comprising at least one immobilized capture agent. The microwell array and capture agent array are coupled to form a plurality of enclosed interfaces, each enclosed interface comprising a microwell and a capture agent set such that the contents of each microwell are accessible to all of the isolated features of at least one set, thereby accessible to all of the immobilized capture agents.

In one embodiment, each of the plurality of isolated features has a distinguishable spatial localization. In one embodiment, each of the plurality of isolated features is a feature selected from the group consisting of a line, shape, and dot. For example, in one embodiment, the shape of each isolated feature is distinguishable from the shape of all other isolated features.

In one embodiment, at least some of the plurality of microwells is a high aspect ratio rectangular well, having dimensions of about 1-2 mm in length and about 5-50 μm in depth.

In one embodiment, the plurality of compounds comprise at least one compound selected from the group consisting of a protein, peptide, peptide fragment, cell surface receptor, nucleic acid, hormone, antigen, and growth factor. In one embodiment the plurality of compounds comprise at least one protein secreted from a single cell contained within a microwell.

In one embodiment, the plurality of capture agents comprise at least one compound selected from the group consisting of an antibody, protein, peptide, peptide fragment, and nucleic acid.

In one embodiment, at least one isolated feature comprises one or more immobilized capture agents, wherein each immobilized capture agent within the isolated feature has an associated secondary capture agent with a different detectable label.

In one embodiment, each microwell is rectangular with a length of about 10-2000 μm, a width of about 10-100 μm, and a depth of about 10-100 μm.

In one embodiment, each capture agent set comprises about 10-100 isolated features, each isolated feature comprising at least one immobilized capture agent that specifically binds to one compound.

In one embodiment, each isolated feature has a width of about 25-30 μm. In one embodiment, each isolated feature is separated from another isolated feature of the same set at a distance of about 25 μm for a pitch size of about 50 μm or more.

In one embodiment, the capture agent array comprises greater than 10 different capture agents, thereby allowing for the detection of greater than 10 different compounds. In one embodiment the capture agent array comprises greater than 40 different capture agents, thereby allowing for the detection of greater than 40 different compounds.

In one embodiment, the microwell array comprises a microwell density of about 200 microwells per $cm^2$ to about 20,000 microwells per $cm^2$.

The present invention also includes a method of spatially encoded multiplexed detection of a plurality of compounds from a single cell, the method comprising providing a microwell array comprising a plurality of individual microwells in uniform arrangement; applying a fluid to a surface of the microwell array such that a sub-nanoliter volume of the fluid comprising a single cell flows into at least one microwell; providing a capture agent array comprising a plurality of immobilized capture agents, each capture agent capable of specifically binding to one of the plurality of compounds, where the immobilized capture agents are arranged in capture agent sets, wherein each capture agent set comprises a plurality of isolated features at spatially identifiable locations, each isolated feature comprising at least one immobilized capture agent; and contacting the microwell array with the capture agent array to form a plurality of enclosed interfaces, each enclosed interface comprising a microwell and a capture agent set such that the fluid within each microwell is accessible to all of the isolated features of a set and is thereby accessible to all of the of immobilized capture agents. The method further comprises providing suitable conditions to allow for the binding of the plurality of compounds to the immobilized capture agents to form immobilized capture agent—compound complexes; removing the capture agent array from the microwell array; contacting the capture agent array with a plurality of labeled secondary capture agents, wherein each labeled secondary capture agent specifically binds to a formed immobilized capture agent-compound complex, to form immobilized capture agent-compound-labeled secondary capture agent complexes; detecting the presence of the detectable label on the capture agent array; and correlating the presence of the detectable label on the capture agent array with the presence of at least one compound.

In one embodiment each of the plurality of isolated features is a feature selected from the group consisting of a line, shape, and dot. For example, in one embodiment, the shape of each isolated feature is distinguishable from the shape of all other isolated features.

In one embodiment, the fluid applied to the microwell surface comprises a cell. In one embodiment, the fluid flows into an individual microwell by gravitational force alone.

In one embodiment, the plurality of compounds comprise at least one compound selected from the group consisting of a protein, peptide, peptide fragment, cell surface receptor, nucleic acid, hormone, antigen, and growth factor. In one embodiment, the plurality of compounds comprise at least one protein secreted from a single cell contained within a microwell.

In one embodiment, the plurality of capture agents comprise at least one compound selected from the group consisting of an antibody, protein, peptide, peptide fragment, and nucleic acid.

In one embodiment, at least one isolated feature comprises more than one immobilized capture agent, wherein each immobilized capture agent within the isolated feature has an associated secondary capture agent with a different detectable label.

In one embodiment, each microwell is rectangular with a length of about 10-2000 μm, a width of about 10-100 μm, and a depth of about 10-100 μm.

In one embodiment, each capture agent set comprises about 10-100 isolated features, each isolated feature comprising at least one immobilized capture agent that specifically binds to one compound.

In one embodiment, each isolated feature has a width about 25-30 μm. In one embodiment, each isolated feature is separated from another isolated feature of the same set at a distance of about 25 μm.

In one embodiment, the capture agent array comprises greater than 10 different capture agents, thereby allowing for the detection of greater than 10 different compounds. In one embodiment, the capture agent array comprises greater than 40 different capture agents, thereby allowing for the detection of greater than 40 different compounds.

In one embodiment, the microwell array comprises a microwell density of about 200 microwells per cm² to about 20,000 microwells per cm².

In one embodiment, applying the fluid to the microwell array surface produces a plurality of individual microwells which comprise a single cell.

In one embodiment, the spatial location of the detected detectable label on the capture agent array is correlated to the identity of at least one of the plurality of compounds and to the individual microwell from which the compound was detected. In one embodiment, the shape of the detected detectable label on the capture agent array is correlated to the identity of at least one of the plurality of compounds. In one embodiment, the spectral properties of the detected detectable label on the capture agent array is correlated to the identity of at least one of the plurality of the compounds. In one embodiment, the spatial location of the detected detectable label and spectral properties of the detected detectable label on the capture agent array is correlated to the identity of one of the plurality of compounds and to the individual microwell from which the compound was detected. In one embodiment, the spatial location of the detected detectable label, shape of the detected detectable label, and the spectral properties of the detected detectable label on the capture agent array is correlated to the identity of one of the plurality of compounds and to the individual microwell from which the compound was detected.

In one embodiment, the method assays the phenotype of a plurality of single cells within the sample by detecting 5 or more compounds secreted by the single cells.

In one embodiment, applying the suspension to the microwell array surface produces a plurality of individual microwells which each comprise a single cell, thereby providing a high throughput method of multiplexed detection of compounds secreted by a plurality of single cells.

In one embodiment, the combination of compounds detected in an individual microwell is indicative of the phenotype of the single cell contained within the microwell. In one embodiment, the phenotype of the cell defines the cell as a cancer cell. In one embodiment, the phenotype of the cell defines the cell as a metastasizing cancer cell. In one embodiment, the phenotype of the cell defines the aggressiveness of a cancer cell.

In one embodiment, the plurality of single cells comprises a population of immune cells and the method assays the heterogeneity of the immune cells. In one embodiment, the phenotype of one or more single cells indicates the progression of a disease or delineates individual disease stages.

The present invention also includes a method of spatially and spectrally encoded multiplexed detection of a plurality of compounds from a single cell, the method comprising providing a microwell array comprising a plurality of individual microwells in uniform arrangement; applying a fluid to a surface of the microwell array such that a sub-nanoliter volume of the fluid comprising a single cell flows into at least one microwell; providing a capture agent array comprising a plurality of immobilized capture agents, each capture agent capable of specifically binding to one of the plurality of compounds, where the immobilized capture agents are arranged in capture agent sets, wherein each capture agent set comprises a plurality of isolated features at spatially identifiable locations, each isolated feature comprising more than one immobilized capture agent; and contacting the microwell array with the capture agent array to form a plurality of enclosed interfaces, each enclosed interface comprising a microwell and a capture agent set such that the fluid within each microwell is accessible to all of the isolated features of a set and is thereby accessible to all of the of immobilized capture agents. The method further comprises providing suitable conditions to allow for the binding of the plurality of compounds to the immobilized capture agents to form immobilized capture agent—compound complexes; removing the capture agent array from the microwell array; contacting the capture agent array with a plurality of labeled secondary capture agents, wherein each secondary capture agent is labeled with one of a plurality of detectable labels, where each secondary capture agent is configured to bind to a immobilized capture agent-compound complex at an isolated feature to form an immobilized capture agent-compound-secondary agent complex, such that the immobilized capture agent-compound-secondary capture agent complexes of an isolated feature each have a spectrally distinct label; detecting the presence of the plurality of detectable labels on the capture agent array; and correlating the spatial location and spectral properties of each detected detectable label on the capture agent array with the presence of at least one compound.

In one embodiment each of the plurality of isolated features is a feature selected from the group consisting of a line, shape, and dot. For example, in one embodiment, the shape of each isolated feature is distinguishable from the shape of all other isolated features.

In one embodiment, the fluid applied to the microwell surface comprises a cell. In one embodiment, the fluid flows into an individual microwell by gravitational force alone.

In one embodiment, the plurality of compounds comprise at least one compound selected from the group consisting of a protein, peptide, peptide fragment, cell surface receptor, nucleic acid, hormone, antigen, and growth factor. In one embodiment, the plurality of compounds comprise at least one protein secreted from a single cell contained within a microwell.

In one embodiment, the plurality of capture agents comprise at least one compound selected from the group consisting of an antibody, protein, peptide, peptide fragment, and nucleic acid.

In one embodiment, at least one isolated feature comprises more than one immobilized capture agent, wherein each immobilized capture agent within the isolated feature has an associated secondary capture agent with a different detectable label.

In one embodiment, each microwell is rectangular with a length of about 10-2000 µm, a width of about 10-100 µm, and a depth of about 10-100 µm.

In one embodiment, each capture agent set comprises about 10-100 isolated features, each isolated feature comprising at least one immobilized capture agent that specifically binds to one compound.

In one embodiment, each isolated feature has a width about 25-30 µm. In one embodiment, each isolated feature is separated from another isolated feature of the same set at a distance of about 25 µm.

In one embodiment, the capture agent array comprises greater than 10 different capture agents, thereby allowing for the detection of greater than 10 different compounds. In one embodiment, the capture agent array comprises greater than 40 different capture agents, thereby allowing for the detection of greater than 40 different compounds.

In one embodiment, the microwell array comprises a microwell density of about 200 microwells per cm² to about 20,000 microwells per cm².

In one embodiment, applying the fluid to the microwell array surface produces a plurality of individual microwells which comprise a single cell.

In one embodiment, the spatial location of the detected detectable label and spectral properties of the detected detectable label on the capture agent array is correlated to the identity of one of the plurality of compounds and to the individual microwell from which the compound was detected. In one embodiment, the spatial location of the detected detectable label, shape of the detected detectable label, and the spectral properties of the detected detectable label on the capture agent array is correlated to the identity of one of the plurality of compounds and to the individual microwell from which the compound was detected.

In one embodiment, the method assays the phenotype of a plurality of single cells within the sample by detecting 5 or more compounds secreted by the single cells.

In one embodiment, applying the suspension to the microwell array surface produces a plurality of individual microwells which each comprise a single cell, thereby providing a high throughput method of multiplexed detection of compounds secreted by a plurality of single cells.

In one embodiment, the combination of compounds detected in an individual microwell is indicative of the phenotype of the single cell contained within the microwell. In one embodiment, the phenotype of the cell defines the cell as a cancer cell. In one embodiment, the phenotype of the cell defines the cell as a metastasizing cancer cell. In one embodiment, the phenotype of the cell defines the aggressiveness of a cancer cell.

In one embodiment, the plurality of single cells comprises a population of immune cells and the method assays the heterogeneity of the immune cells. In one embodiment, the phenotype of one or more single cells indicates the progression of a disease or delineates individual disease stages.

The present invention also includes a system for the multiplexed detection of a plurality of compounds from single cells comprising a device comprising a microwell array and a capture agent array, and a plurality of secondary capture agents. The microwell array comprises a plurality of individual microwells in uniform arrangement, at least some of the plurality of individual microwells configured to contain a single cell in a sub-nanoliter volume of contents. The capture agent array comprises a plurality of immobilized capture agents, each immobilized capture agent capable of specifically binding to one of the plurality of compounds, where the immobilized capture agents are arranged in uniform capture agent sets, wherein each capture agent set comprises a plurality of isolated features at spatially identifiable locations, each isolated feature comprising at least one immobilized capture agent. The microwell array and capture agent array are coupled to form a plurality of enclosed interfaces, each enclosed interface comprising a microwell and a capture agent set such that the contents of each microwell are accessible to all of the isolated features of at least one set, thereby accessible to all of the immobilized capture agents. Each secondary capture agents comprises a detectable label and is configured to bind to a immobilized capture agent-compound complex formed at an isolated feature by the binding of a compound of the plurality of compounds to an immobilized capture agent of the plurality of immobilized capture agents.

In one embodiment, each of the plurality of isolated features has a distinguishable spatial localization. In one embodiment, each of the plurality of isolated features is a feature selected from the group consisting of a line, shape, and dot. For example, in one embodiment, each isolated feature is distinguishable from the shape of all other isolated features.

In one embodiment, at least some of the plurality of microwells is a high aspect ratio rectangular well, having dimensions of about 1-2 mm in length and about 5-50 μm in depth.

In one embodiment, the plurality of compounds comprise at least one compound selected from the group consisting of a protein, peptide, peptide fragment, cell surface receptor, nucleic acid, hormone, antigen, and growth factor. In one embodiment the plurality of compounds comprise at least one protein secreted from a single cell contained within a microwell.

In one embodiment, the plurality of capture agents comprise at least one compound selected from the group consisting of an antibody, protein, peptide, peptide fragment, and nucleic acid.

In one embodiment, at least one isolated feature comprises one or more immobilized capture agents, wherein each immobilized capture agent within the isolated feature has an associated secondary capture agent with a different detectable label.

In one embodiment, each microwell is rectangular with a length of about 10-2000 μm, a width of about 10-100 μm, and a depth of about 10-100 μm.

In one embodiment, each capture agent set comprises about 10-100 isolated features, each isolated feature comprising at least one immobilized capture agent that specifically binds to one compound.

In one embodiment, each isolated feature has a width of about 25-30 μm. In one embodiment, each isolated feature is separated from another isolated feature of the same set at a distance of about 25 μm for a pitch size of about 50 μm or more.

In on embodiment, the capture agent array comprises greater than 10 different capture agents, thereby allowing for the detection of greater than 10 different compounds. In one embodiment the capture agent array comprises greater than 40 different capture agents, thereby allowing for the detection of greater than 40 different compounds.

In one embodiment, the microwell array comprises a microwell density of about 200 microwells per $cm^2$ to about 20,000 microwells per $cm^2$.

In one embodiment, the detectable label is selected from the group consisting of a fluorescent label, radioactive label, ferromagnetic label, paramagnetic label, luminescent label, electrochemiluminescent label, phosphorescent label, and chromatic label.

In one embodiment, each of the plurality of secondary capture agents comprise the same detectable label.

In one embodiment, each secondary capture agent is labeled with one of a plurality of detectable labels, where each secondary capture agent is configured to bind to a immobilized capture agent-compound complex at an isolated feature to form an immobilized capture agent-compound-secondary agent complex, such that the immobilized capture agent-compound-secondary capture agent complexes of an isolated feature each have a spectrally distinct label.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 1A-1C show a set of images depicting the structure of an exemplary high-throughput multiplexed single cell secretomic assay. FIG. 1A depicts a schematic illustration showing integration of a high-density capture agent array chip and a subnanoliter microchamber array chip for high-throughput multiplexed protein secretion assay at the single cell level. FIG. 1B is a scanned fluorescence image showing high uniformity of protein loading across the entire capture agent microarray (1 in.×2 in.). Fluorescently labeled bovine serum albumin (FITC-BSA) was used in this test. FIG. 1C is a photograph stitched from a large number of individual pictures collected by an automated, motorized phase contrast microscope. Together it covers the entire subnanoliter microchamber chip that was loaded with human immune cells (U973). Scale bar 2 mm. The first enlarged image shows a column of microchamber array (scale bar 300 µm). The second enlarged image shows individual cells loaded in microchambers (scale bar 50 µm).

FIG. 2A is a list of all 22 proteins assayed in single cell microchips and their functions in human physiology. FIG. 2B is a set of titration curves obtained using recombinant proteins. A total of 18 antibody pairs were validated and 4 others were left out in the titration curves due to the lack of working recombinants. Fluorescence intensity represents the original photon counts averaged from 16 spots for each protein. Error bars indicate 3×SD.

FIG. 3A is an image depicting a representative region of the scanned image showing the raw data of single cell secretomic measurement. Three subpanels on the right are optical micrograph, fluorescence image, and overlay for 16 microchambers. FIG. 3B depicts a heat map that shows the profile of 14 proteins secreted from 1278 single cells (U87). Each row is a single cell and each column corresponds to a protein of interest. FIG. 3C is a set of scatter plots showing fluorescence intensity measured for six selected proteins (FGF, VEGF, MIF, IL-6, IL-8, MCP-1) versus the number of cells in a microchamber. (* $P<0.05$,  $P<0.01$, * $P<0.001$) FIG. 3D depicts the population kinetics for U87 cell line. Control (MEM medium), secretion supernatant from population at different time points (0 h, 1 h, 2 h, 3 h, 6 h, 9 h, 12 h, 24 h).

FIGS. 4A-4D show a set of images depicting the results of experiments demonstrating the correlation between protein secretion profiles and cellular migration for A549 cells. FIG. 4A is an image depicting representative optical images showing three single cells (n=384) before (0 h) and after (24 h) protein secretion assay. FIG. 4B is a scatter plot showing the fluorescence intensity corresponding to IL-8 secretion versus migration distance of individual cells ($P<0.05$). FIG. 4C is a scatter plot showing a similar analysis on MCP-1 ($P=0.14$). FIG. 4D is a scatter plot showing a similar analysis on IL-6 ($P=0.75$). Each dot represents a single cell.

FIG. 5A depicts a schematic for the procedure for processing tissue specimens, preparation of single cell suspension and application of primary cells to the subnanoliter microchamber array chip. FIG. 5B depicts a representative region of the scanned image for patient 1. FIG. 5C and FIG. 5D depict heat maps showing single-cell secretomic signatures of primary tumor cells from two patients (patients 1 and 2), respectively. The data are presented as a result of unsupervised hierarchical clustering analysis. FIG. 5E is a set of scatter plot matrices showing protein-protein correlation in single cells. Each subpanel is the scatter plot showing the level of a protein versus the other in all single cells measured. The proteins are indicated at the diagonal line. The correlation coefficient is computed as R via a linear regression analysis. The entire matrix is color-coded by red (positive correlation) and blue (negative correlation). The color intensity is proportional to the R value.

FIG. 9A is an image depicting a representative region of the scanned image showing the raw data of single cell secretomic measurement. Three subpanels on the right are optical micrograph, fluorescence image and overlay for 14 microchambers. FIG. 9B is a heat map that shows the profile of 14 proteins secreted from 551 single cells (U937). Each row is a single cell and each column corresponds to a protein of interest. FIG. 9C is a pair of scatter plots showing fluorescence intensity measured for four selected proteins (IL8, MCP-1, RANTES and TNFa) versus the number of cells in a microchamber. The cells were stimulated with 20 µg/mL of PMA to differentiate to macrophage and then challenged by 1 mg/mL of LPS to become activated right before they were loaded onto the microchip to secretion analysis.

FIGS. 23A-23B show a set of schematics depicting exemplary isolated features of the invention. FIG. 23A depicts an exemplary set of isolated features. Features are measured at 25 microns per line and have a 25 micron spacing to realize a pitch size of 50 microns per non-parallel line set. FIG. 23B is a schematic depicting exemplary isolated features of the invention, with features having distinct geometries.

FIG. 30 is a table of an exemplary panel of 42 different cytokines, extracellular proteins, growth factors, and antigens, using 14 spatial locations (lines) and 3 colors per location.

FIG. 40 is a table comparing the single-cell assay of the invention (SCMA) with intracellular cytokine staining (ICS) in detection of cytokines in nonstimulated (control) and LPS stimulated cells.

FIG. 44A depicts a comparison of the U937 derived macrophage single cell protein secretion results with population cell secretion results. FIG. 44B depicts a comparison of protein secretion frequency obtained from single cell secretion platform and ICS (intracellular cytokine staining). FIG. 44C is a set of graphs demonstrating similar cell subpopulation definitions defined by IL-8 and MCP-1 protein secretion results both by SCMA (left) and ICS (right). FIG. 44D depicts U937 macrophage single cell polyfunctionality analysis based on their protein secretion results.

FIG. 45A depicts heatmaps showing comparison between untreated and LPS stimulated U937 monocyte derived macrophage protein secretion profiles. FIG. 45B depicts visualization of ingle cell secretion results with VISNE. FIG. 45C depicts visualization of individual proteins (MIF, IL-8, MCP-1, RANTES, MIP-1a, MIP-1b) secretion results with VISNE.

FIG. 46A depicts heatmaps showing protein secretion profiles comparison between untreated and stimulated (LPS, PAM3, poly IC) U937 monocyte derived macrophage. FIG. 46B depicts a heat map showing the frequency of U937 macrophage cell that secrete any individual protein under different stimulations. FIG. 46C depicts the visualization of single cell results with VISNE. FIG. 46D depicts the visualization of individual proteins (MIF, IL-8, MCP-1, MIP-1b) secretion results with VISNE.

FIG. 47A: Alexa fluor 488 conjugated BSA was spotted onto poly-1-lysine glass slide. The 488 channel signal and 532 channel signal showed good and stable correlation between each other ($R^2 \approx 98\%$) and compensation equation can be extracted; FIG. 47B: correlation between real signal from 532 channel and crosstalk from 488 channel for Alexa fluor 532 conjugated BSA.

FIG. 51A: the ratio of single cell signal vs zero cell signal are quite similar from these two chips. FIG. 51B: the ratios of the single cell secretion signal from these two chips are very close to 1.

FIG. 53A presents a bar and line graph demonstrating the wide variety in the number of proteins secreted. FIG. 53B depicts a set of pie graphs demonstrating the percentage of cells secreting various ranges of proteins.

FIG. 55A: control; FIG. 55B: LPS stimulated. The results shows different protein has different secretion dynamics at differing time points of analysis under selected stimulation conditions.

FIGS. 56A-56F depict the results of experiments demonstrating the U937 derived macrophage protein secretion profile before (untreated) and after 100 ng/mL LPS stimulation. FIG. 56A: All identical cells before and after stimulation. FIG. 56B: Identical single cells comparison before and after stimulation. FIG. 56C-FIG. 56E: Scatterplots showing the relation between IL-8 (before treatment and after) and IL-6, IL-10, TNF-a. FIG. 56F: the change of IL-8, MCP-1, Rantes, MMP-9 from the same cell before and after LPS stimulation.

FIG. 57 depicts a comparison of the single cell multiplexing array of the present invention (IsoPlexis) with CyTOF® Mass Cytometer system.

DETAILED DESCRIPTION

Figures 2A, 2B:
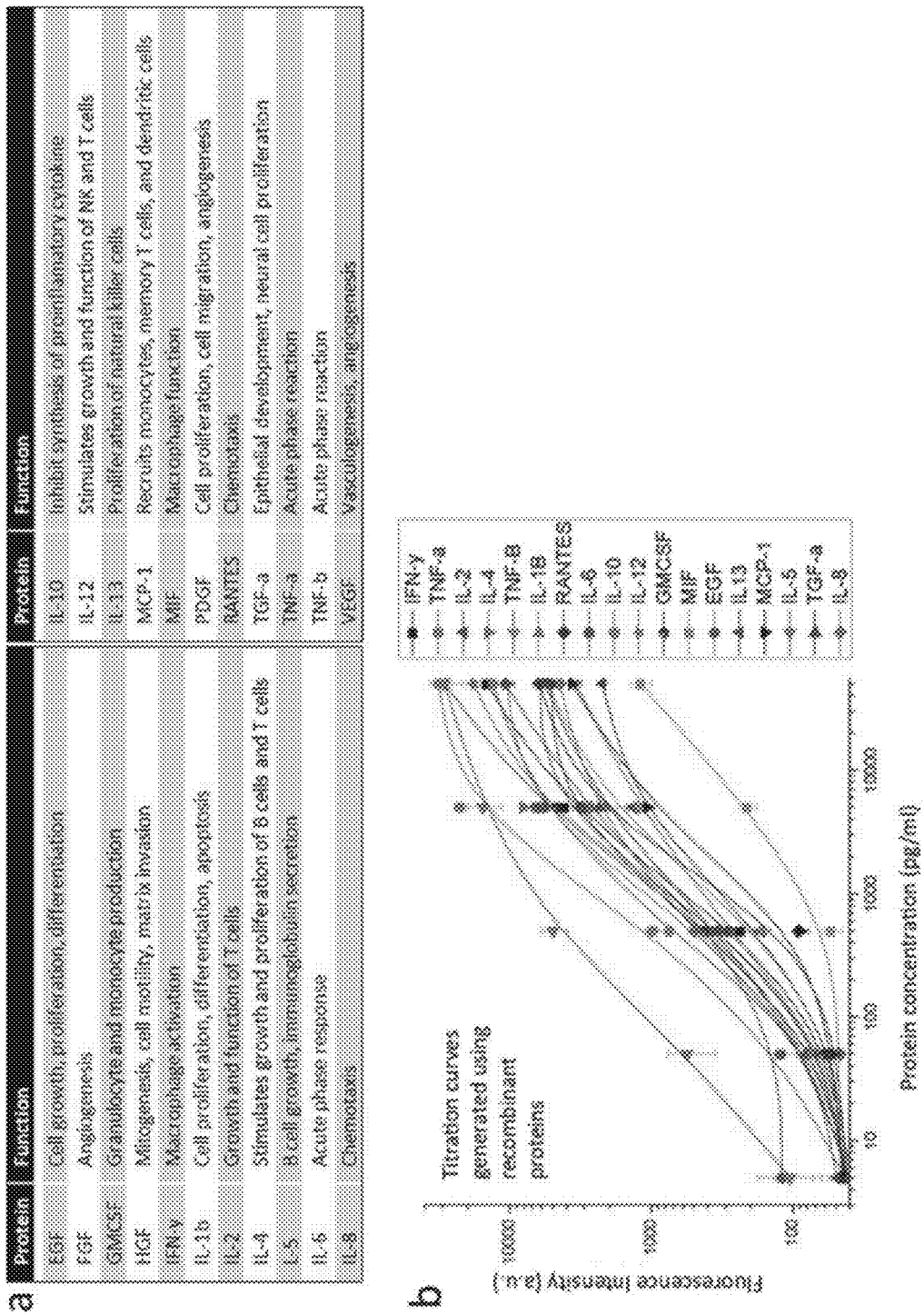
FIGS. 2A-2B illustrate an exemplary protein panel assayed in an exemplary device of the invention.

The present invention relates generally to a system, device, and method for high-throughput single-cell analysis. In one embodiment, the invention is used to quantitatively detect the presence of a wide number of compounds derived from single cells. For example, in one embodiment, the invention is used for the multiplexed detection of secreted compounds from a single cell. In certain embodiments, the invention allows for the multiplexed detection of secreted proteins, including chemokines, cytokines, growth factors, antigens, and the like, from single cells. The ability to analyze the secreted compounds from single cells allows for assessment of the variability of cellular phenotype within a cell population. Further, the invention provides an effective mechanism for identifying phenotypically rare and/or potential harmful cell types within a population, whose activity would be otherwise hidden in traditional population-based assays. In one embodiment, the device of the invention is a microchip comprising two independent components: (1) a high-density sub-nanoliter microwell array and (2) a substrate comprising a high-density capture agent array. In one embodiment, the invention uses spatial and spectral encoding of compound capture.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody" as used herein, refers to an immunoglobulin molecule, which is able to specifically bind to a specific epitope on an antigen. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1988; Houston et al., 1988; Bird et al., 1988).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

The term "polypeptide" as used herein is defined as a chain of amino acid residues, usually having a defined sequence. As used herein the term polypeptide is mutually inclusive of the terms "peptide" and "protein".

By the term "specifically binds," as used herein, is meant that a capture agent recognizes a specific compound, but does not substantially recognizes or binds to other compounds in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

As used herein, an "isolated feature" or "feature" refers to a distinguishable element found within the capture agent set described herein. In certain embodiments, an isolated feature is a continuous line, non-continuous line, dot, square, triangle, or other distinguishable geometry, or combination of geometries. The geometry may be any in which a capture agent set comprises reproducible numbers and arrangements of isolated features.

As used herein, an "interface" refers to a unit comprising one microwell and a capture agent set, described herein. An interface is formed when the microwell array and capture agent array of the invention are contacted together in a consistent and repeated pattern.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates generally to a system, device, and method for high-throughput single-cell analysis. In certain embodiments, the invention is used for the quantitative multiplexed detection of a wide number of secreted compounds from single cells. The invention provides an effective mechanism for identifying single cell phenotypes within a cell population, where single cell phenotype would be otherwise hidden in traditional population-based assays. For example, the invention allows for the identification of single cells that are phenotypically rare, or are of diagnostic value. In one embodiment, the invention allows for the identification and quantification of single cell polyfunctionality upon stimulation or challenge. In certain embodiments, the invention allows for the identification of potentially harmful single cells within a cell population. The ability to analyze the secreted compounds from single cells allows for assessment of the variability of cellular phenotype within a cell population.

In one embodiment, the device of the invention is a microchip comprising two independent components: (1) a high-density sub-nanoliter microwell array and (2) a substrate comprising a high-density capture agent array.

The capture agent array is comprised of a plurality of capture agents, with each capture agent specifically recognizing a compound of interest. The capture agents are arranged in distinct isolated features along the substrate to provide spatial distinction between the various capture agents, herein described as "spatial encoding." For example, in one embodiment, the capture agent array is comprised of a plurality of lines, with each line comprised of one or more specific capture agent. In one embodiment, the capture agent array comprises repeats of isolated feature sets, where each set comprises all of the features needed to encompass all of the plurality of capture agents. As described elsewhere herein, the device of the invention allows for detection and quantification of 5-100 different compounds. Thus, the capture agent array of the invention comprises 5-100 capture agents, each specific for one compound of interest. In certain embodiments, the capture agents of the invention specifically bind to a secreted protein of interest. In one embodiment, the capture agents of the invention specifically bind one of 45 secreted proteins or antigens of interest, which are captured within one microwell.

The multiplexing ability of the present invention allows for the detection of 2 or more, 3 or more, 4 or more, 5 or more, 10 or more, 20 or more, 40 or more, 50 or more, 100 or more, and the like, compounds. For example, as is described elsewhere herein, the spatial and spectral encoding provided by the invention allows for the ability to detect very large number of different compounds.

It is noted herein that while the description presented herein describes a feature having one or more than one capture agent, it is not meant that the feature has one molecule of the capture agent. Rather, a skilled artisan will understand that a feature having an immobilized capture agent describes that the feature comprises some number or concentration of a specific capture agent. Further, a feature having three capture agents is meant that the feature comprises some number or concentration of three different specific capture agents.

The microwell array is comprised of a plurality of sub-nanoliter sized microwells, each configured to house a single cell. Each microwell allows for constraint of a single cell while also, in certain embodiments, constraining the secreted compounds, secreted by the single cell, to the microwell. As such, the microwell array of the invention allows for analysis of the secreted proteins, specifically secreted by the constrained single cell.

The device of the invention comprises the microwell array attached to the capture agent array, to form interfaces between each microwell and a complete set of capture agents disposed upon the capture agent array. In certain embodiments, compounds secreted from a single cell, housed in a microwell, bind specifically to a capture agent on the capture agent array. Bound proteins are then visualized by, for example, use of a group of labeled secondary capture agents in a sandwich ELISA.

In certain embodiments, bound compounds are visualized be the use of a secondary capture agent. In one embodiment, bound compounds are visualized by use of a group of labeled secondary capture agents with one or more differently labeled secondary capture agents directed to bind to a particular line or feature, herein referred to as "spectral encoding," as described elsewhere herein.

In one embodiment, the device of the invention allows for a multiplexed assay using the spatial position or shape of the plurality of isolated features to determine the presence or absence of each compound of interest. For example, observation of a detectable label (through binding of a labeled secondary detection agent), at a particular spatial location and/or within a distinguishable feature provides information about the presence of the particular compound.

In another embodiment, the device of the invention allows for a multiplexed spatial and spectral assay, where the distinguishable spatial feature as well as the color of selected labels at the feature determines the presence or absence of each compound of interest.

For example, in certain embodiments, each feature is comprised of more than one capture agent, each of which corresponds to a distinct colored label. For example, in one embodiment, the assay allows for the detection of m×n compounds of interest, where m is equal to the number of distinguishable isolated features, and n is equal to the number of detectable labels used per feature. Importantly, the assay does not require a unique label for each of the m×n compounds. Rather, the combination of spatial features and colored labels provides only the need for n different labels. For example, in one embodiment, three different capture agents are positioned in each isolated feature, with three differently labeled secondary capture agents used, each differently labeled secondary capture agent corresponding to one of the three positioned capture agents. In one embodiment, each set comprises fifteen isolated features, which thereby allow the detection of 45 (15×3) compounds per single cell.

The invention also provides a method for analyzing the secretome of a single cell. The method comprises providing a microwell array and contacting the array with a solution comprising a cell. The solution spreads over the array such that the cell flows into a well of the array. The method further comprises affixing a capture agent array to the microwell array, such that the cell and solution within the well are in contact with a population of capture agents immobilized on the capture agent array. Compounds (e.g. proteins) secreted from the single cell are thus able to specifically bind to a capture agent located on the capture agent array. In one embodiment, the method further comprises administering a group of secondary capture agents, which are tagged with a detectable label, to the capture agent array to form a detectable complex at a site of binding between a secreted compound and an immobilized capture agent.

The invention also provides a method of identifying the presence of a cell with a specific phenotype within a sample obtained from a subject. As described elsewhere herein, the device of the invention allows for the ability to detect the specific profile of secreted compounds from individual cells. Thus, the device and method of the invention allows for the identification of one or more cells whose profile is indicative of a particular cellular phenotype. For example, in one embodiment, the method comprises identifying a cell whose profile of secreted proteins is indicative of a cancer cell, a malignant cancer cell, or the like. In one embodiment, the method identifies subpopulations of individual cells with specific characteristics.

Device

Figure 21:
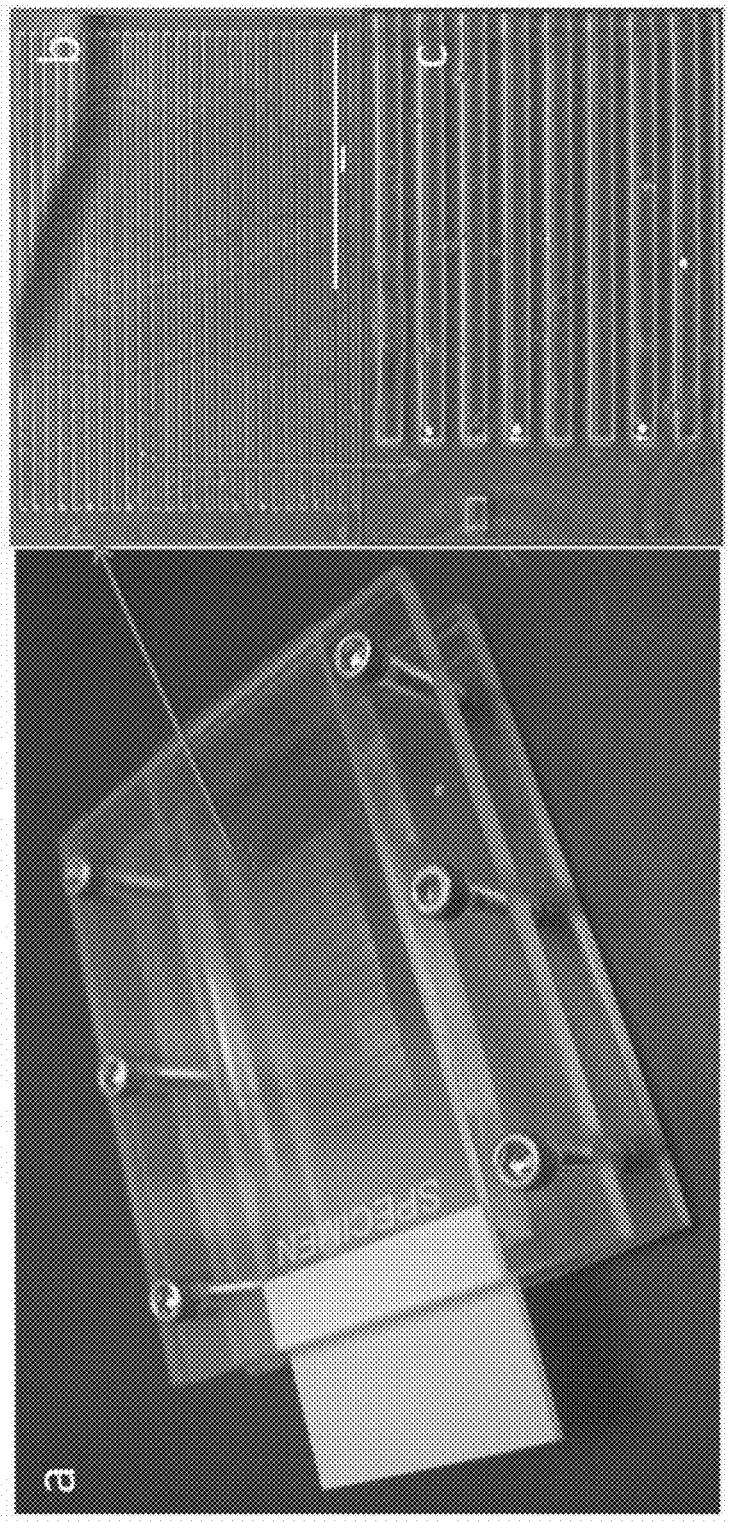
FIG. 21 is a set of images depicting an exemplary device of the invention.
Figure 22:
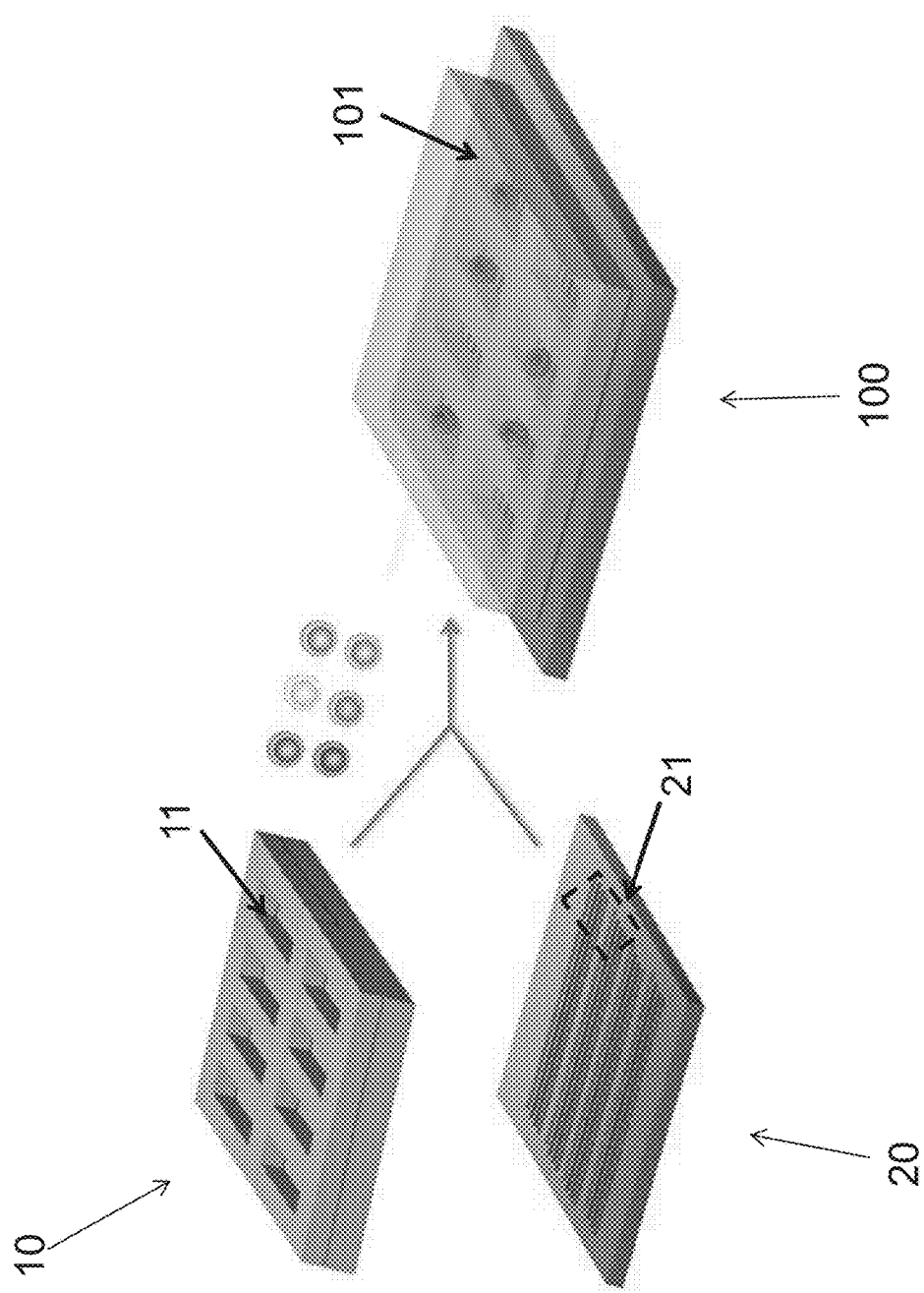
FIG. 22 is a schematic depicting an exemplary microwell array and capture probe array of the invention.

In one embodiment, the device of the invention comprises a microwell array interfaced with a capture agent array. An image of an exemplary device is depicted in FIG. 21, while an exemplary schematic of the device and its components are shown in FIG. 1 and FIG. 22. As shown in FIG. 22, device 100 comprises microwell array 10 coupled to capture agent array 20. Device 100 couples individual microwells 11 with a complete set 21 of capture agents to form a plurality of interfaces 101. Each interface 101 comprises an individual microwell 11 and a capture array set 21, which is used to perform multiplexed detection of a wide number of compounds present within microwell 11. Microwell array 10 and capture agent array 20 are thus configured for precise coupling to allow for high throughput detection and analysis from individual microwells. In one embodiment, the device comprises about 1,000-100,000 microwells coupled to capture agent sets. Further description of microwell array 10 and capture agent array 20 are provided below.

Microwell Array

In certain embodiments, the device of the invention comprises a microwell array. The microwell array captures and constrains cells and their secreted compounds within the spatial limitations of each well thereby preventing escape of the cells during implementation. Further, the microwell array allows cells to function normally in terms of release of secreted compounds. In one embodiment, the cells remain alive (i.e. unfixed) and function normally within the microwell.

The microwell array of the invention comprises a plurality of individual microwells. In certain embodiments, the microwell array comprises a high-density array of individual microwells in order to provide a device that allows for high throughput analysis. The microwell array can be of any shape or size suitable for the desired implementation of the device. In one embodiment, the microwell array is rectangular, having a defined length and width.

In one embodiment, the microwell array is 0.5-10 cm in length. In another embodiment, the microwell array is 1-5 cm in length. In another embodiment, the microwell array is 2-3.5 cm in length.

In one embodiment, the microwell array is 0.5-10 cm in width. In another embodiment, the microwell array is 1-5 cm in width. In another embodiment, the microwell array is 2-3.5 cm in width.

In one embodiment, the microwell array comprises about 10-1,000,000 individual microwells. In another embodiment, the microwell array comprises about 500-500,000 individual microwells. In another embodiment, the microwell array comprises about 100-100,000 individual microwells.

In one embodiment, the microwell array comprises microwells at a density of about 200 microwells per cm$^2$ to about 20,000 microwells per cm$^2$.

As used herein, a microwell is a chamber that captures and constrains cells in an environment in which they remain alive and function. Each microwell is configured to ensure reasonable survival of the cells. For example, cells within a microwell have a survival rate similar to that expected in an in vivo environment. Further, each microwell is configured to allow for normal functionality of captured cells during the length of the implementation of the device of the invention.

The dimensions of each microwell of the microwell array are designed to effectively constrain cells and secreted compounds while promoting the normal function and survival of constrained cells. The microwell is designed to cover the full area of one or more of the interfaced capture agent set. As such, the size and shape of each microwell is not limited, but rather can take any size and shape suitable for the cell type used and multiplexing ability desired. In one embodiment, each microwell is rectangular, with a defined length, width and depth. Each microwell captures a sub-nanoliter volume of fluid, including, for example cell suspension, physiological fluid, fluidic sample, possible reagents, and the like.

In one embodiment, each microwell is 1-10,000 µm in length. In another embodiment, each microwell is 5-5,000 µm in length. In another embodiment, each microwell is 10-2,000 µm in length.

In one embodiment, each microwell is 1-1,000 µm in width. In another embodiment, each microwell is 5-500 µm in width. In another embodiment, each microwell is 10-100 µm in width.

In one embodiment, each microwell is 1-1,000 µm in depth. In another embodiment, each microwell is 5-500 µm in depth. In another embodiment, each microwell is 10-100 µm in depth.

In one embodiment, each microwell is a high aspect ratio rectangular well. For example, in one embodiment, each microwell is about 1.8 mm long and about 20 µm wide.

In one embodiment, each microwell is about 10-100 µm in width, 20-200 µm in depth, and 100-2,000 µm in length.

In certain embodiments, individual microwells are spaced laterally and longitudinally in an array of rows and/or columns. In one embodiment, individual microwells are regularly spaced at about 10-100 µm in separation.

Fabrication of the microwell array may be done making use of any suitable method or methods necessary to construct the array described herein. For example, in one embodiment, the microwell array is fabricated by negative photolithography wafer molding and subsequent soft-polymer (PDMS, Sylgard 184) using standard procedures for laydown. In one embodiment, soft lithography techniques are used for elastomer stamping and molding of the array.

In one embodiment, the microwell array is optically transparent to allow for imaging of the array or of a cell or cells within the array. In certain embodiments of the invention, imaging of the array is desired for cell-counting, microwell alignment, and/or determination of cellular localization within a microwell.

In one embodiment, the microwell array is manufactured and configured for a single use. In another embodiment, the microwell array is manufactured and configured to be reusable. For example, in certain embodiments, the microwell array is reusable after a standard wash procedure using water, saline, buffers, or a combination thereof. In certain embodiments, the microwell array is suitable to be sterilized, for example by use of an autoclave or UV irradiation.

In one embodiment the microwell is functionalized or otherwise manipulated for the purposes of cell tethering or other immobilization.

Each microwell is configured to capture and constrain an individual cell or cells over the area of the accompanying capture agent array. For example, each microwell may be specifically designed such that the microwell contains a desired number of cells of a particular cell type. In certain embodiments, each microwell contains 1, 2, 3, 5, 10, 15, 20, 50, or 100 cells. In a particular embodiment, each microwell is configured to contain a single cell. As used herein, a single cell is defined as an individual cell of any cell type or cell line. In certain embodiments, the cell is a secretory cell. In other embodiments, the cell is a non-secretory cell. In a preferred embodiment, the single cell remains alive for some, most, or all of the implementation time of the device. In a more preferred embodiment, the single cell remains alive during the entire duration of the implementation of the device. For example, in certain embodiments, the device is used to assay the profile of secreted proteins from a single cell during a 24 hour period. It is preferred that the microwell allows for survival of a single cell for the 24 hour period.

In one embodiment, the microwell array is configured to be compatible with the capture agent array, such that when the microwell array is affixed to the capture agent array, each individual microwell, and cells and proteins contained therein, are in contact with at least one full set of capture agent features (e.g. lines, dots, etc) to ensure that all of the plurality of capture agents are accessible to the contents of the microwell.

Capture Agent Array

In certain embodiments, the device of the invention comprises a capture agent array. The capture agent array comprises a plurality of capture agent sets, where each capture agent set comprises all of the plurality of capture agents desired for the multiplexed detection of compounds. As described elsewhere herein, each set is configured to be accessible to the contents of a single microwell.

In certain embodiments, the capture agent array comprises repeats of capture agent sets. In one embodiment, each set is spatially distinct from all other sets. In one embodiment, each set is separated by about 10-100 µm.

In one embodiment, the capture agent array comprises 10-1,000,000 individual capture agent sets. In another embodiment, the capture agent array comprises about 500-500,000 individual capture agent sets. In another embodiment, the capture agent array comprises about 100-100,000 individual capture agent sets.

Each set is sized and shaped to correspond with one or more microwells, as described above. For example, in one embodiment each set corresponds to a single microwell. Assembly of the device by contacting the microwell array with the capture agent array thereby forms a plurality of interfaces, with each interface comprising a microwell and a set. The device is only limited in that the contents of each microwell must be accessible to all the isolated features comprised in a set, as further described elsewhere herein. In certain embodiments, each set is configured based upon the size of multiplexing desired. Thus, in one embodiment, each set is rectangular having with a defined length and width In one embodiment, each set is 1-10,000 µm in length. In another embodiment, each set is 5-5,000 µm in length. In another embodiment, each set is 10-2,000 µm in length.

In one embodiment, each set is 1-1,000 µm in width. In another embodiment, each set is 5-500 µm in width. In another embodiment, each set is 10-100 µm in width.

Figure 23A:
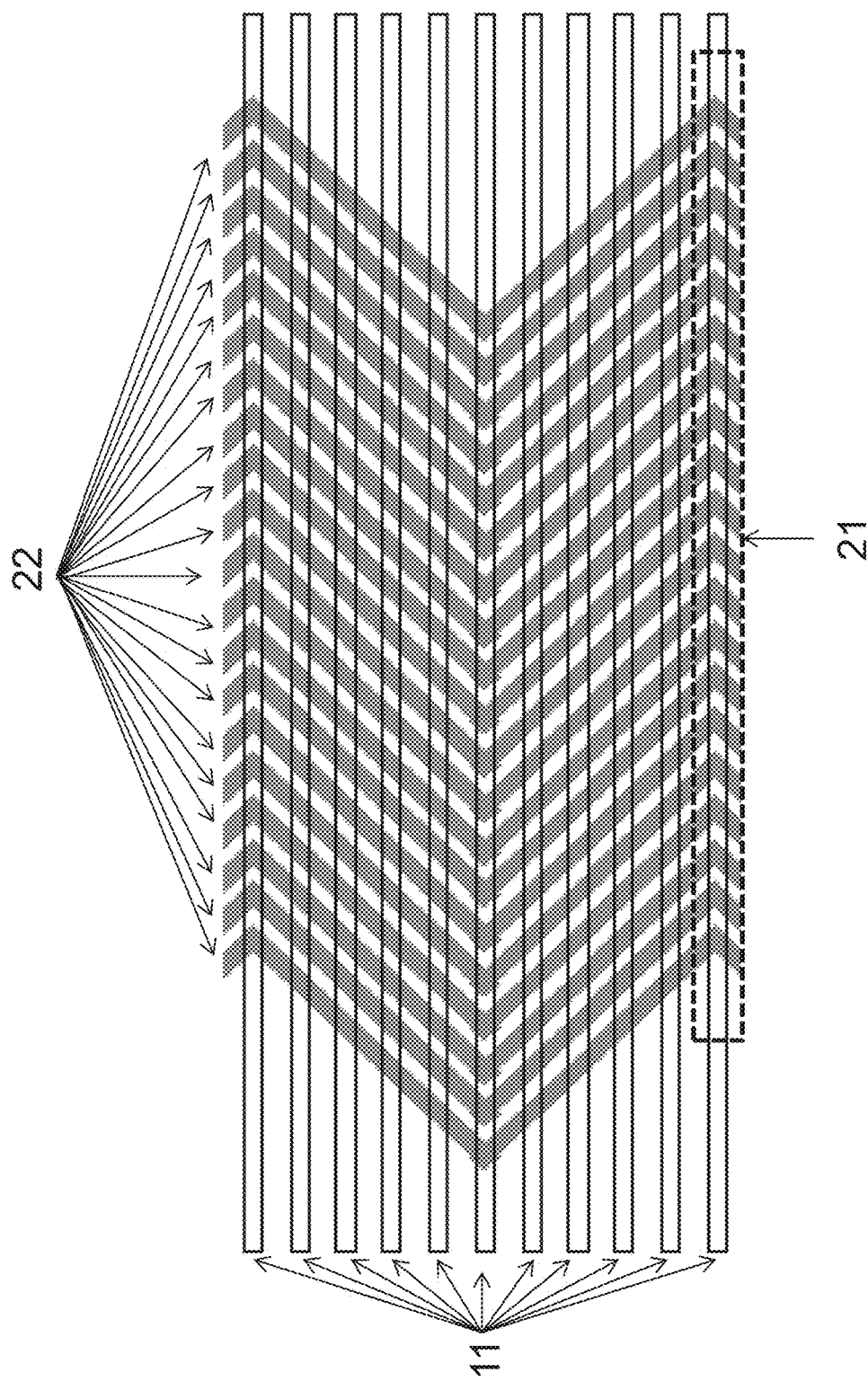

As shown in FIG. 23A, in certain embodiments, each set 21 comprises a plurality of spatially isolated features 22 that comprise one or more different immobilized capture agents. Device 10 is assembled such an interface 101 is formed between each set 21 and each microwell 11, such that the contents of each microwell 11 are accessible to each of the plurality of features 22. For example, in one embodiment, set 21 comprises a plurality of features 22, where each feature 22 is a line, where each line comprises one or more immobilized capture agents. Features 22 are not limited to any particular size or shape. For example, in one embodiment, features 22 are straight lines. In another embodiment, features 22 are zig-zag lines (as depicted in FIG. 23). Each feature 22 comprises one or more immobilized capture agents for the detection of a compound of interest. For example, in one embodiment, set 21 comprises twenty individual features 22, with each feature comprising a specific capture agent to detect one of twenty compounds of interest. In one embodiment, the capture agent immobilized on one feature 22 is not comprised in another feature 22. Thus, detecting compound binding at a particular feature 22, as described elsewhere herein, provides information as to the presence of a particular compound of interest.

Figure 24:
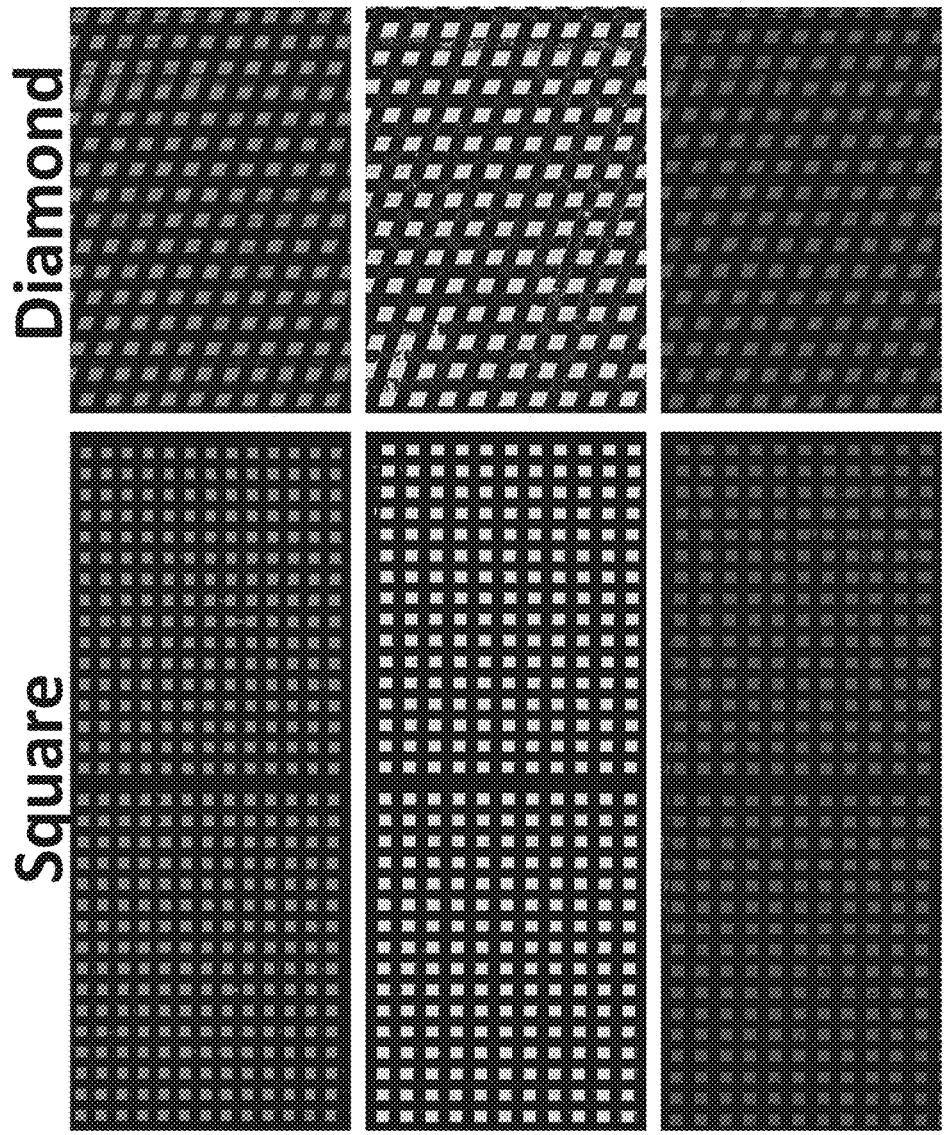
FIG. 24 is a set of images depicting an ultra-high-density antibody microarray. The shape of each microwell can be varied (i.e., square vs. diamond shapes) and this array can be interfaced with single-cell microwell cell capture chip to conduct single-cell high-plex protein profiling. This array is fabricated by cross-flow patterning technique and can also be fabricated by micro-scale printing techniques such as microspotting and inject printing.

FIG. 23B, depicts an alternative embodiment of a comprising a plurality of isolated features 122. In this embodiment, each feature 122 comprises a distinctive shape or geometry. Each feature 122 comprises one or more immobilized capture agents immobilized in the particular shape of feature 122. Micropatterning technology can be used to fabricate feature size and shape with very high resolution. Exemplary techniques include microinject printing, microcontact printing, dip-pen lithography, microchannel-guided flow patterning, and the like. However, the device is not limited to any particular method of immobilizing capture agents into isolated features. For example, FIG. 24, depicts exemplary capture agent arrays, comprising capture agents arranged as squares or diamond features. This array is fabricated by cross-flow patterning technique and can also be fabricated by micro-scale printing techniques such as micro spotting and inject printing.

Isolated features allow for the determination of which compound (or combination of compounds) are present within each microwell. For example, the spatial location of the feature, the shape of the feature, and/or the combination thereof is used to identify which compound of interest (or combination of compounds of interest) bound to its specific capture agent immobilized on the feature. Further, as each set corresponds to an individual microwell, the spatial location of a capture agent set on the capture agent array allows for the determination of within which individual microwell the compound (or combination of compounds) were present. This therefore allows for determining an individualized profile stemming from the contents of each microwell. In certain embodiments, the isolated features are repeating and at least one set of isolated features in full in contained per microwell. In one embodiment, two or more sets may be contained in each microwell, for example as a control.

In one embodiment, detection of the bound compound of interest is made with an ELISA-based immunoassay, as described elsewhere herein. Importantly, the use of distinguishable isolated features (spatially distinguishable and/or distinguishable by shape or geometry) allows for multiplexing for a large number of compounds from single cells, as a unique secondary antibody label is not needed for each compound. This type of "spatial encoding" allows for the detection of the relevant secreted compounds for each microwell from its observed binding to a spatial location within the isolated feature set interfaced with the specific microwell, rather than a specific label on each secondary capture agent specific to the compound, as in traditional ELISA. For example, traditional assays require a 1:1 compound to detectable label relationship in order to correlate the label to the particular compound of interest. As described herein, the use of isolated features allows that each compound be associated with the same detectable label (or at least same group of labels used in spectral assays described elsewhere herein).

As described elsewhere herein, each specific capture agent specifically binds to a compound (protein, antigen, receptor, nucleic acid, etc) of interest. Each isolated feature has a defined spatial location and/or shape within the capture agent set, thereby allowing for easy and effective determination of whether or not a specific compound of interest is present in the corresponding microwell. For example, in one embodiment, each isolated feature is spaced at about 2-25 µm from one another. In one embodiment, each set comprises at least one of the plurality of isolated features. That is, each isolated feature is represented at least once in each set. In some embodiments, one or more isolated features are repeated a multitude of times within each interface. For example, in one embodiment, an interface may comprise a single well interfaced with multiple sets.

In one embodiment, each set comprises a total of about 5-100 different capture agents. In another embodiment, each set comprises a total of about 10-75 different capture agents. In another embodiment, each set comprises a total of about 20-50 different of capture agents. For example, in one embodiment, the invention provides for a 45-plexed detection of compounds, wherein each set comprises 45 different capture agents.

In one embodiment, each set comprises about 5-100 isolated features. In another embodiment, each set comprises about 10-50 isolated features. In another embodiment, each set comprises about 20-30 isolated features.

In certain embodiments, isolated features are continuous over multiple capture agent sets. For example, in some fabrication techniques it may be easier to fabricate continuous lines or shapes that would span over a plurality of sets. Contacting the capture agent array with the microwell array then breaks the continuous features into individual sets corresponding to individual microwells. In another embodiment, the capture array is fabricated such that isolated features are non-continuous, and are thus placed only at locations that will correspond to the interface between a microwell and capture agent set.

In certain embodiments, each isolated feature (e.g. line, shape, etc) comprises a single specific capture agent. In another embodiment, each isolated feature comprises 2, 3, 5, 10, or more different capture agents. In these embodiments, specific binding to a particular capture agent within the feature is determined by use of different detectable labels on a second set of capture agents used in an ELISA-based assay, with each label corresponding to a particular capture agent, termed herein as "spectral encoding."

For example, in one embodiment, the array comprises at least one set comprising fifteen features (e.g. lines, dots, or the like). In one embodiment, the first feature comprises one or more molecules of a first capture agent, the second feature comprises one or more molecules of a second capture agent, the third feature comprises one or more molecules of a third capture agent, and so on. This is repeated until the fifteenth feature, which comprises one or more molecules of a fifteenth capture agent.

In one embodiment, each feature comprises more than one capture agent. For example, in one embodiment, the first feature comprises one or more molecules of a first capture agent, one or more molecules of a second capture agent, and one or more molecules of a third capture agent; while the second feature comprises one or more molecules of a fourth capture agent, one or more molecules of a fifth capture agent, and one or more molecules of a sixth capture agent. This is repeated until the fifteenth feature, which comprises one or more molecules of the forty-third capture agent, one or more molecules of the forty-fourth capture agent, and one or more of the forty-fifth capture agent. In this embodiment, each capture agent within a feature is distinguishable by the color of a secondary capture agent targeted to the capture agent, defined as spectral encoding as described elsewhere herein.

For example, in one embodiment, an isolated feature comprises three different capture agents, each specific for a different compound of interest. Determination of which of the three compounds of interest (or combination of compounds of interest) is found in the microwell is done by applying a second set of three different capture agents, one labeled with a red label, one with a green label, and one with a blue label, to the immobilized capture agents in an ELISA based reaction to produce a detectable complex at the feature. Detecting the presence of a red, green, and blue label at the spatial location of each isolated feature in the capture agent arrays thus allows for determination of which of the three compounds (or combination of three compounds) of interest is present per said isolated feature. Scaling this principle over all the isolated features present in the capture agent set allows for the multiplexed detection of a very large number of compounds. For example, devices have been configured and demonstrated to detect for up to 60 different compounds.

In certain embodiments, the invention provides spatial and spectral multiplexing of compounds of interest. For example, in one embodiment, the ability to multiplex is partially defined by the number of spatially distinguishable isolated features per capture agent set. In one embodiment, each isolated feature is about 5-50 µm in width. In one embodiment, each isolated feature is about 25-30 µm in width. In one embodiment each isolated feature is about 500-2000 µm in length. In one embodiment, each isolated feature is separated by about 5-50 µm. In one embodiment, each isolated feature is separated by about 25-30 µm. In one embodiment, each isolated feature is about 25 µm in width and separated by about 25 µm from the next feature, thereby giving a pitch size of about 50 µm. The present invention demonstrates the ability to produce very small spatially distinguishable isolated features to thereby increase the spatial multiplexing ability of the device.

In one embodiment, the ability to multiplex is partially defined by the number of spectrally distinct labels used such that each isolated feature can contain more than one capture agent, thus allowing for detection of more than one type of compound of interest per isolated feature. For example, in one embodiment, the capture array set comprises 15 spatially distinct features, each feature comprising 3 different capture agents, distinguishable through use of 3 different ELISA-based secondary capture agents conjugated to different detectable labels. This configuration therefore allows for 45-plexed detection.

The capture agent array performs a multiplexed highly-quantitative analysis of secretions per single cell by coupling to the single-cell isolating microwells. The repeating sets serve to allow each microwell to capture a full detection range of 5-100 compounds per single cell without significant deviation in accuracy of capture between each microwell due to the uniformity of design.

Patterning of capture agents at isolated features and sets is achieved through any suitable technique. For example, Capture agent patterning can be achieved at high accuracy through inkjet printing, fine print spotting, flow patterning on a functionalized substrate, contact printing on functionalized glass substrate, or microprinting using epoxy-coated glass substrate or poly-amine glass substrate with printing needles or strips at 2-30 µm feature resolution. In certain embodiments, the functionalized substrate comprises a poly-L-lysine coated substrate. However, any functionalized substrate that provides the physical and/or chemical affinity to immobilize the capture agents to a high degree of reproducibility with limited cross-reactivity of the capture agents in the array of the invention may be used.

As described above, each capture agent set comprises a plurality of capture agents, where each capture agent specifically binds to a compound of interest being assayed in the desired implementation. Exemplary compounds of interest, include, but are not limited to proteins, peptides, antibodies, enzymes, surface receptors, nucleic acids, peptide fragments, cytokines, growth factors, hormones, and the like. In certain embodiments, the compound or compounds of interest are compounds known or thought to be secreted by the cell or cells contained with the microwell of the device. However, the invention is not limited to detection of secreted compounds, but rather any compound that is accessible to the capture agent array. For example, a compound of interest can include one that is accessible upon lysis of the cell, either through the death of the cell or following user manipulation.

Capture agents include, but are not limited to, antibodies, antibody fragments, proteins, peptides, and nucleic acids. In certain embodiments, capture agents have a capture affinity of about 1 pM to about 150 pM to their target compound. As described elsewhere herein, detection of the binding between the immobilized capture agent on the array and its target compounds is performed through ELISA-based coupling using a second group of capture agents, where each of the second group of capture agents specifically binds to a capture agent-compound complex. In certain embodiments, each member of the second group of capture agents is labeled with a detectable label, including, but not limited to, a dye or fluorophore. The secondary capture agents may comprise antibodies, antibody fragments, proteins, peptides, and nucleic acids. In some embodiments, a secondary capture agent specifically binds an immobilized capture agent of the capture agent array. In another embodiment, a secondary capture agent, such as a detection antibody, specifically binds the compound of interest.

In one embodiment, the capture agent of the invention comprises a peptide. In certain embodiments, the peptide capture agent specifically binds to a compound of interest, for example a secreted compound of interest.

The peptide of the present invention may be made using chemical methods. For example, peptides can be synthesized by solid phase techniques (Roberge J Y et al (1995) Science 269: 202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer.

The peptide may alternatively be made by recombinant means or by cleavage from a longer polypeptide. The composition of a peptide may be confirmed by amino acid analysis or sequencing.

The variants of the peptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two peptides is determined by comparing the amino acid sequence and its conserved amino acid substitutes of one peptide to a sequence of a second peptide. Variants are defined to include peptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence. The present invention includes amino acid sequences that are at least 60%, 65%, 70%, 72%, 74%, 76%, 78%, 80%, 90%, or 95% similar or identical to the original amino acid sequence. The degree of identity between two peptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

The peptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction.

The peptides of the invention may include unnatural amino acids formed by post-translational modification or by introducing unnatural amino acids during translation.

In one embodiment, the capture agent of the invention comprises an antibody, or antibody fragment. In certain embodiments, the antibody capture agent specifically binds to a compound of interest, for example a secreted compound of interest. Such antibodies include polyclonal antibodies, monoclonal antibodies, Fab and single chain Fv (scFv) fragments thereof, bispecific antibodies, heteroconjugates, human and humanized antibodies.

Such antibodies may be produced in a variety of ways, including hybridoma cultures, recombinant expression in bacteria or mammalian cell cultures, and recombinant expression in transgenic animals. The choice of manufacturing methodology depends on several factors including the antibody structure desired, the importance of carbohydrate moieties on the antibodies, ease of culturing and purification, and cost. Many different antibody structures may be generated using standard expression technology, including full-length antibodies, antibody fragments, such as Fab and Fv fragments, as well as chimeric antibodies comprising components from different species. Antibody fragments of small size, such as Fab and Fv fragments, having no effector functions and limited pharmokinetic activity may be generated in a bacterial expression system. Single chain Fv fragments show low immunogenicity.

In one embodiment, the capture agent of the invention comprises an isolated nucleic acid, including for example a DNA oligonucleotide and a RNA oligonucleotide. In certain embodiments, the nucleic acid capture agent specifically binds to a compound of interest, for example a secreted compound of interest. For example, in one embodiment, the nucleic acid comprises a nucleotide sequence that specifically binds to a compound of interest. For example, in one embodiment, the nucleic acid is complementary to a secreted nucleic acid of interest.

The nucleotide sequences of a nucleic acid capture agent can alternatively comprise sequence variations with respect to the original nucleotide sequences, for example, substitutions, insertions and/or deletions of one or more nucleotides, with the condition that the resulting nucleic acid functions as the original and specifically binds to the compound of interest.

In the sense used in this description, a nucleotide sequence is "substantially homologous" to any of the nucleotide sequences describe herein when its nucleotide sequence has a degree of identity with respect to the nucleotide sequence of at least 60%, advantageously of at least 70%, preferably of at least 85%, and more preferably of at least 95%. Other examples of possible modifications include the insertion of one or more nucleotides in the sequence, the addition of one or more nucleotides in any of the ends of the sequence, or the deletion of one or more nucleotides in any end or inside the sequence. The degree of identity between two polynucleotides is determined using computer algorithms and methods that are widely known for the persons skilled in the art. The identity between two amino acid sequences is preferably determined by using the BLASTN algorithm [BLAST Manual, Altschul, S., et al., NCBI NLM NIH Bethesda, Md. 20894, Altschul, S., et al., J. Mol. Biol. 215: 403-410 (1990)].

System for Multiplexed Detection

In one embodiment, the present invention includes a system for multiplexed detection of compounds secreted by a single cell. In certain embodiments, the system comprises the device described in detail elsewhere herein. That is, in one embodiment the system comprises a device comprising a microwell array and a capture agent array, as described above.

In one embodiment, the device of the system comprises a capture agent array having a plurality of sets, each set comprising a plurality of isolated features, wherein each feature comprises one or more immobilized capture agents that bind to a specific compound of interest.

In one embodiment, the system comprises a group of secondary capture agents which are administered to the device following incubation of population of single cells with the immobilized capture agents of the capture agent array. The secondary capture agent specifically binds to an immobilized capture agent, the compound of interest, or to an immobilized capture agent-compound complex. That is, the secondary capture agent is used in a sandwich-type assay, and in certain embodiments aid in the detection of a compound bound to the capture agent array.

In certain embodiments, the secondary capture agents comprise antibodies, antibody fragments, proteins, peptides, and nucleic acids. In one embodiment, the secondary capture agents are labeled with a detectable label. Secondary capture agents, specific for binding an immobilized capture agent—compound complex, can be labeled with any detectable label, including but not limited to, fluorescent labels, radioactive labels, ferromagnetic labels, paramagnetic labels, luminescent labels, electrochemiluminescent labels, phosphorescent labels, chromatic labels, and the like. Non-limiting examples of fluorescent labels include, green fluorescent protein (GFP), cyan fluorescent protein (CFP), yellow fluorescent protein (YFP), red fluorescent protein (RFP), orange fluorescent protein (OFP), eGFP, mCherry, hrGFP, hrGFPII, streptavidin APC, Alexa 488, Alexa 532, Alexa 594, and the like. Fluorescent labels may also be photoconvertable such as for example kindling red fluorescent protein (KFP-red), PS-CFP2, Dendra2, CoralHue Kaede and CoralHue Kikume.

In one embodiment, the secondary capture agent is labeled with a tag region, including for example a peptide or other epitope. For example, in one embodiment, the secondary capture agent is labeled with biotin (i.e. biotinylated), such that the use of a fluorescently labeled streptavidin, or other detectably labeled streptavidin, is used to visualize the biotinylated secondary capture agent.

In one embodiment, all secondary capture agents are labeled with the same detectable label. In another embodiment, the secondary capture agents are differently labeled, in order to differentiate the binding of one secondary capture agent from another. In one embodiment, each capture agent immobilized on the capture agent array is assigned a corresponding labeled ELISA-detection secondary capture agent, such that each capture agent at a given feature has a distinct corresponding label. In certain embodiments, the plurality of labels corresponding to the plurality of immobilized capture agents within a given feature do not exhibit any cross-reactivity during the spectral encoding embodiments presented herein.

For example, in one embodiment, the group of secondary capture agents comprise one or more subgroups, with each subgroup having a particular detectable label. The system is thus devised such that a secondary capture agent from each subgroup is configured to bind to a single specific immobilized capture agent-compound complex formed at a specific feature. Thus, if, for example, all compounds were present in a given microwell, all of the different detectable labels would be observed at each feature. The differentially labeled secondary capture agents allows for the spectral encoding of the presence of a given compound. That is, the combination of the spatial location of the label and the precise type (i.e. color) of the label, identifies the compound that is present.

In one embodiment, the system comprises a detector for detecting the identity and location of each detectable label. The detector may be any suitable detector that is capable of detecting each label, including, but not limited to a fluorescent microscope, fluorescent detector, or fluorescent scanner.

In one embodiment, the system comprises a computing device. The computing device may include a desktop computer, laptop computer, tablet, smartphone or other device and includes a software platform for control of the system components, display of raw data, and analysis of acquired data. The computing devices may include at least one processor, standard input and output devices, as well as all hardware and software typically found on computing devices for storing data and running programs, and for sending and receiving data over a network.

In certain embodiments, the system of the invention comprises hardware and software which detect and quantify detection signals from the array. The signals may be quantified using any suitable analysis software package, or using custom made analysis algorithms. Exemplary analyses and graphical output of data are presented elsewhere herein.

Methods of Multiplexed Detection

The present invention provides methods of simultaneously detecting a large number of compounds of interest in a small sample. For example, in one embodiment, the invention allows multiplexed detection of proteins from a single cell housed in a microwell, as described elsewhere herein. The method allows for the determination of individualized profiles from single cells, which in certain embodiments is preferred over profiles from a population of cells. The ability to discriminate profiles from individual cells can aid in the determination of a particular cellular phenotype, hiding within a total population. This would, for example, be useful in detecting a cancerous cell, malignant cell, or metastasizing cell, in a tissue sample, that would otherwise be difficult or near impossible to detect. In certain embodiments, the method provides for the ability to calculate an average single cell parameter(s) that provide more information than population based assays. Such analysis can be used, for example, to identify sub-populations and/or grouped phenotypes. Isolating these subpopulations of individual cells, grouped by single cell multi-plexed parameters, can be valuable for isolating important active groups of malignant cancer cells and responsive immune cells in a tissue sample. The multiplexing ability of the present invention therefore allows for the isolation or identification of phenotypic subtypes. For example, the method identifies the relative amount of a given phenotype within a population. Further, such analysis can provide, but is not limited to, the quantification of cross-correlation between secreted compounds or cellular products, the creation of population or whole chip compound distribution statistics, and the evaluation of polyfunctionality expressed on the single cell level over the population tested.

In one embodiment, the method comprises loading a single cell into a microwell described herein. The device of the present invention allows for microwell loading that does not require active fluidics (i.e. pumps, pressurized flow, etc) or external force manipulation of live cells. Rather, the method comprises loading a single cell into a microwell using gravity alone. This allows for a method in which single cells are isolated and profiled in live conditions without extensive manipulation, which may be time consuming and/or expensive.

The cells profiled by way of the method of the invention may be of any suitable cell type. Applicable cells for consideration include both adherent and non-adherent cells, primary cells and immortalized cell lines, cells from organ tissue, and cells grown ex vivo. In certain embodiments, a cell is administered to the microwell in the form of a solution comprising the cell. For example, the solution can be a single-cell suspension, a media cell suspension, or a physiological fluid naturally comprising the cell. The cell may be from a cell line or isolated from a subject, including a human. In one embodiment, the solution is derived from tissue isolated from a subject. For example, the solution is derived from homogenized tissue.

In one embodiment, the method for loading a cell into the microwell comprises adding a solution comprising a cell directly over a wetted surface of the microwell array. For example, the surface of the microwell array may be wetted with water, saline, buffer, or a suitable cell culture medium. In one embodiment, addition is made in a single motion over approximately the middle of the microwell array at least about 0.1 mm above the surface. Addition of the solution to the surface may be done under any standard pipetting or liquid transfer method known in the art for standard cell culture preparation. The volume of the solution added to the microwell array surface is minimal compared to available multiplex analysis tools. In one embodiment, the method comprises administering about 1-500 µL to the surface. The number of cells within the solution is dependent upon the availability of the cells and the desired throughput. For example, the solution can comprise as low as about $10^3$, $10^2$, or $10^1$ cells. Upon addition of solution to the microwell array surface, the cells of the solution fall into each individual microwell by gravity alone and exhibit a Poisson distribution of cells per well. In certain embodiments, wells with zero cells or multiple cells can be later eliminated from analysis, or included for control and/or background signal processing.

In certain embodiments, the solution comprises one or more components that promote the survival and/or normal function of the cell during implementation. For example, the solution can comprise growth factors, hormones, proteins, enzymes, small molecules, antimicrobials, and the like typically used in cell culture. In some embodiments, the solution comprises suitable cell culture medium. In some embodiments, the solution comprises a test agent or test compound whose effects are desired to be assayed during implementation of the invention. For example, the test agent can comprise a small molecule, protein, nucleic acid, peptide, or the like which may or may not have an effect on the detected profile. For example, the agent may or may not increase the secretion of one or more compounds of interest or decrease the secretion of one or more compounds of interest.

The method further comprises contacting the capture agent array with the microwell array. Creating the proper interface between the microwell array and capture agent array, with the alignment of individual microwells with their corresponding capture array sets, is performed, in one embodiment, by a pressurized clamp mechanism using an integrated device housing. It is noted herein, however, that no precise alignment of the microwell array and capture agent array is necessary. For example, the uniformity of the arrays allow for a loose alignment that does not necessarily require a specific microwell to align with a specific set on the capture array. Further, in certain embodiments, automated analyses conducted post-experiment performs signal matching, which can overcome non-precise alignment. However, the present method is not limited to any particular method of forming this interface. For example, permanent and non-permanent adhesives, screws, clamps, and the like may also be used.

This loading method is solely dependent upon the size of the individual cells and size of microwells, which both dictate the average number of single cells per microwell. In some embodiments, the loading procedure described herein ensures the constraint of about 0 to 20 cells per microwell. The overall distribution of the number of cells per well approximates a Poisson distribution.

In one embodiment, the cells are constrained within the device for a desired period of time over single or multiple time points. In one embodiment, the method comprises constraining the cells within the device for about 1 minute, 5 minutes, 10 minutes, 30 minutes, 1 hour, 2 hours, 4 hours, 8 hours, 16 hours, 1 day, 2 day, 4 days, 1 week, 2 weeks, 1 month, one year, or more.

In one embodiment, the method comprises acquiring images recording the number and location of cells within each microwells. In certain embodiments, this allows for the determination of whether a determined profile was produced by a single cell or rather by a population of single cells. Image acquisition may be carried out by any method known in the art.

In one embodiment, after the desired time course as elapsed, the device is disassembled to remove the capture agent array. The capture agent array is then subjected to known ELISA immunoassay procedures to produce detectable complexes at the sites of compound binding. For example, in one embodiment, a plurality of secondary capture agents, each specific for a different immobilized capture agent—compound complex, as described elsewhere herein, is applied to the surface of the capture agent array under suitable conditions to promote specific binding. As detailed elsewhere herein, each secondary capture agent is labeled with a detectable label, for example, a fluorescent label. In certain embodiments, each of the plurality of secondary capture agents are all labeled with the same label. In other embodiments, secondary capture agents are labeled with different labels to spectrally discriminate between complexes that may have been formed at the same spatial location.

Figure 25:
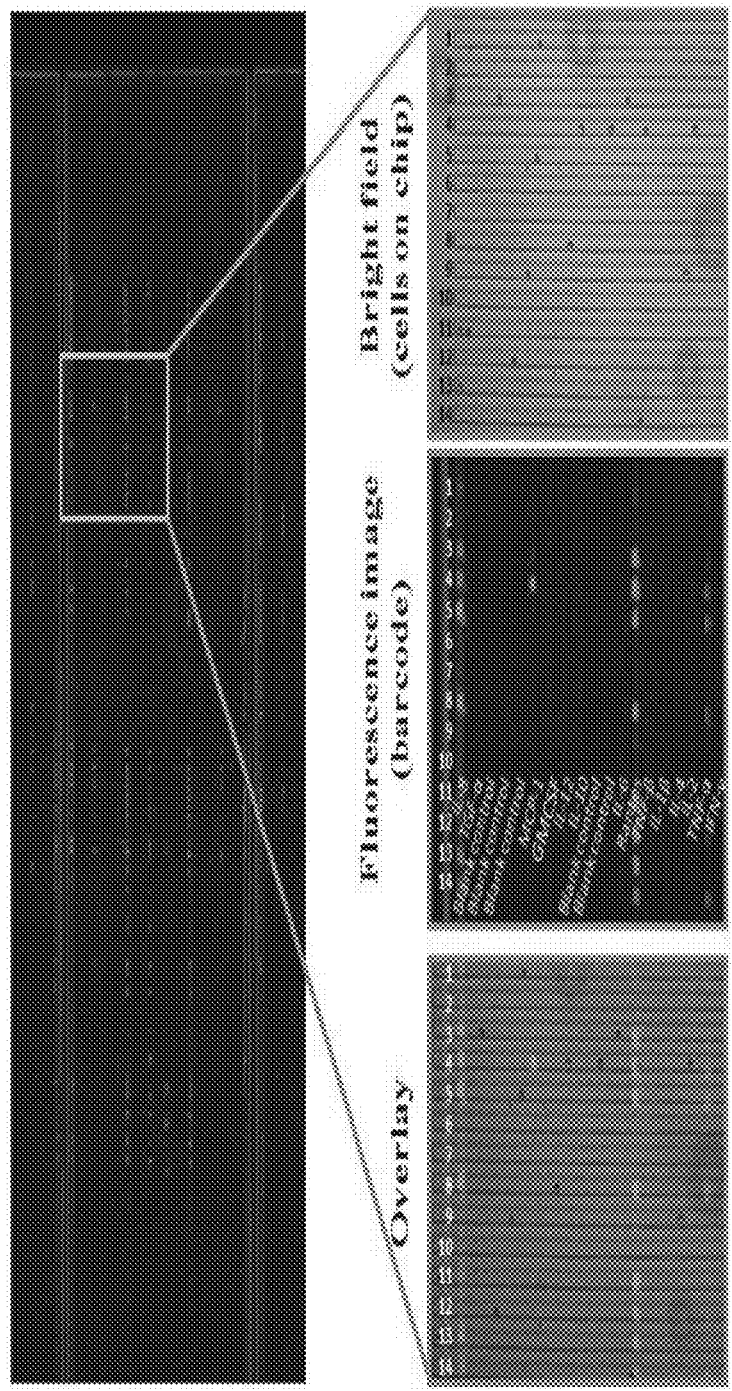
FIG. 25 is a set of images depicting detection of cells within individual microwells (bottom right) and detection of the presence of particular compounds of interest (bottom center).

In one embodiment, following application of the group of secondary capture agents, the capture agent array is imaged for the presence of one or more detectable labels at distinct spatial locations. FIG. 25 depicts an exemplary read-out illustrating (1) a bright-field image of a group of microwells used to detect the presence and/or quantity of cells per microwell, (2) a fluorescent image to detect the presence of a detectable label at specific spatial locations, with each location corresponding to a particular compound of interest, and (3) an overlay of the bright field and fluorescent image.

Imaging of the capture agent array may be done by any suitable method known in the art. For example, in certain embodiments, imaging of the capture agent array comprises use of a fluorescent microscope, fluorescent detector, and/or fluorescent scanner. Image analysis, including the determination of which spatial features of each capture agent set have a detectable label, is then used to construct a multiplexed profile from each set, which thus corresponds to a profile from each microwell. In certain embodiments where a plurality of detectable labels is used, images may be color combined prior to analysis.

Methods of Single Cell Phenotype Determination

The present invention provides a method to elucidate a single cell profile. For example, in one embodiment, the invention provides a method to determine a proteomic profile from a single cell. In another embodiment, the invention provides a method to determine a genomic profile from a single cell. In another embodiment, the invention provides a method to determine a secretomic (i.e. secreted proteins and compounds) from a single cell. In another embodiment, the invention provides a method to determine a combined proteomic, genomic, and/or secretomic profile from a single cell. Further the method provides a high throughput method of determining the profiles for a large quantity of single cells simultaneously.

In one embodiment, the method of the invention is used to evaluate heterogeneity or multifunctionality of immune cells. Immune cells have an essential role in prevention and protection against a variety of infections (Seder et al., 2008, Nature Reviews Immunology, 8: 247). Despite the rapid development of immune cell phenotyping using the powerful flow cytometry technology, it remains difficult to fully dissect the functions of different phenotypes due in part to the extremely high level of cellular heterogeneity including in T cells and monocyte/macrophage (Gordon et al., 2005, Nature Reviews Immunology, 5: 953-964). Moreover, such heterogeneity exists not only at the level of phenotype but also at the level of cell behavior as reflected by the diverse effector functions and activated states (Seder et al., 2008, Nature Reviews Immunology, 8: 247). An immune cell often displays a number of functions, termed multifunctionality, and the combinations of multiple functions determines the immunobiology of a single cell and the "quality" of this cell against a given infection. In a simplified linear differentiation model of the $T_H1$ cells, both phenotypic and functional heterogeneity have been observed in term of CD4+ T-cell cytokine responses. It is noted that these cells display different effector functions (cytokine profiles) at different stages and such functional patterns dynamically evolve with time. It was also found that cells with multiple functions serve best as the memory CD4+ T cells with potent effector potential. The truth is likely far more complex than this linear differentiation model, and over 40 effector functions are associated with helper T cells. The importance of multifunctionality is further exemplified by the observation that non-progressor AIDS patients developed a repertoire of HIV-specific T cells that secret a greater number of different cytokines as compared to the progressor patients. However, there are no technologies available to assess the full spectrum of immune effector functions at the single cell level, and the cellular immunobiology of these dynamically evolving cells remain poorly understood. In certain embodiments, the present method allows for the evaluation of the heterogeneity of immune cells by detecting the secretome of one or more single immune cells, by use of the presently described multiplexed system. For example, the secretome of single immune cells can be evaluated when left untreated, or when stimulated with one or more test compounds. This can thus be used to evaluate the quality of a subject's immune response.

The singular term "cancer" is never one kind of disease, but deceivingly encompasses a large number of heterogeneous disease states, which makes it impossible to completely treat cancer using a generic approach. This is due in part to the significant intratumoral heterogeneity (Furnari et al., 2007, Genes Dev, 21: 2683-2710). Moreover, such heterogeneity is so profound that it exists at the single cell level within a tumor microenvironment. For example, in human brain tumor glioblastoma multiforme, there are never just glioma cells, but also other key cell types such as tumor initiating immune cells (Bao et al., 2006, Cancer Research, 66: 7843-7848; Singh et al., 2004, Nature, 432: 396-401), neural/glial progenitor cells, neurons, astrocytes, oligodendrocytes and the brain-resident immune cells—microglia. Such a remarkable heterogeneity of glioblastoma microenvironment and the lineage relationships of different cells within a solid human tumor can be an important determinant of tumor cell competencies. Individual GBMs can harbor a series of phenotypically distinct self-renewing cell types that promote a range of tumor growth patterns (Chen et al., 2010, Cancer Cell, 17: 362-375). Thus, it is crucial to reveal the hierarchical heterogeneous structure of glioma stem/initiating cells in GBMs and delineate the cell-cell interaction network.

Such interactions are largely mediated by soluble mediators secreted from different cell types. Glioma cells secrete cytokines and chemokines to recruit and subvert their untransformed neighbor microglia that in turn produces inflammatory factors to promote tumorigenesis (Leung et al., 1997, Acta Neuropathol, 93: 518-527; Prat et al., 2000, Neurosci Lett, 283: 177-180; Platten et al., 2003, Annals of Neurology, 54: 388-392; Galasso et al, 2000, Experimental Neurology, 161: 85-95), reflecting the mutual paracrine stimulation between microglial cells and glioma cells. Such a complex cell-cell dialogue in a highly heterogeneous tumor microenvironment is a paramount governing mechanism in cancer immunobiology, but remains difficult to study due to the lack of technologies that can perform informative analysis of single cell protein profiles, in particular, the proteins secreted to modulate cell-cell communications. In certain embodiments, the present method allows for the single cell analysis of secreted proteins from cells within or in the vicinity of a tumor in order to evaluate the cell-cell signaling within the microenvironment. This can allow for the characterization of the tumor, including the aggressiveness, or stage of a tumor, based on the observed signaling phenotype.

The device and method of the invention may be used to determine the presence and/or quantity of any compound. Suitable types of compounds include proteins, nucleic acids, protein fragments, surface receptors, hormones, growth factors, and the like. The precise combination of compounds of interest being assayed by way of the invention is easily controllable and defined by the eventual user. For example, detection of a particular compound is only limited by the availability of a capture agent (e.g. antibody, peptide, nucleic acid sequence, etc.) that specifically binds to the compound. In certain embodiments, the combination of compounds of interest provides the user information about the phenotype of a cell contained within the microwell of the device. In one embodiment, the device is configured for the multiplexed detection of secretable proteins. For example, in one embodiment, the device is configured for the multiplexed detection of one or more of MIF, IL-1RA, IL-15, IL-13, IL-12, IL-10, IL-8, IL-7, IL-6, IL-5, IL-4, IL-3, IL-1b, IL-1a, VEGF, PDGF, NGFβ, HGF, EGF, MCSF, SCF, MIP-1b, IL-22, TNFβ, TNFα, RANTES, MCP-1, IL-17A, TSLP, IL-27, IL-27-1, MMP9, MMP2, IL-23, IL-9, GMCSF, IFN, GCSF, TGFβ, TGFα, MIP-1a, and IL-2.

Figure 26:
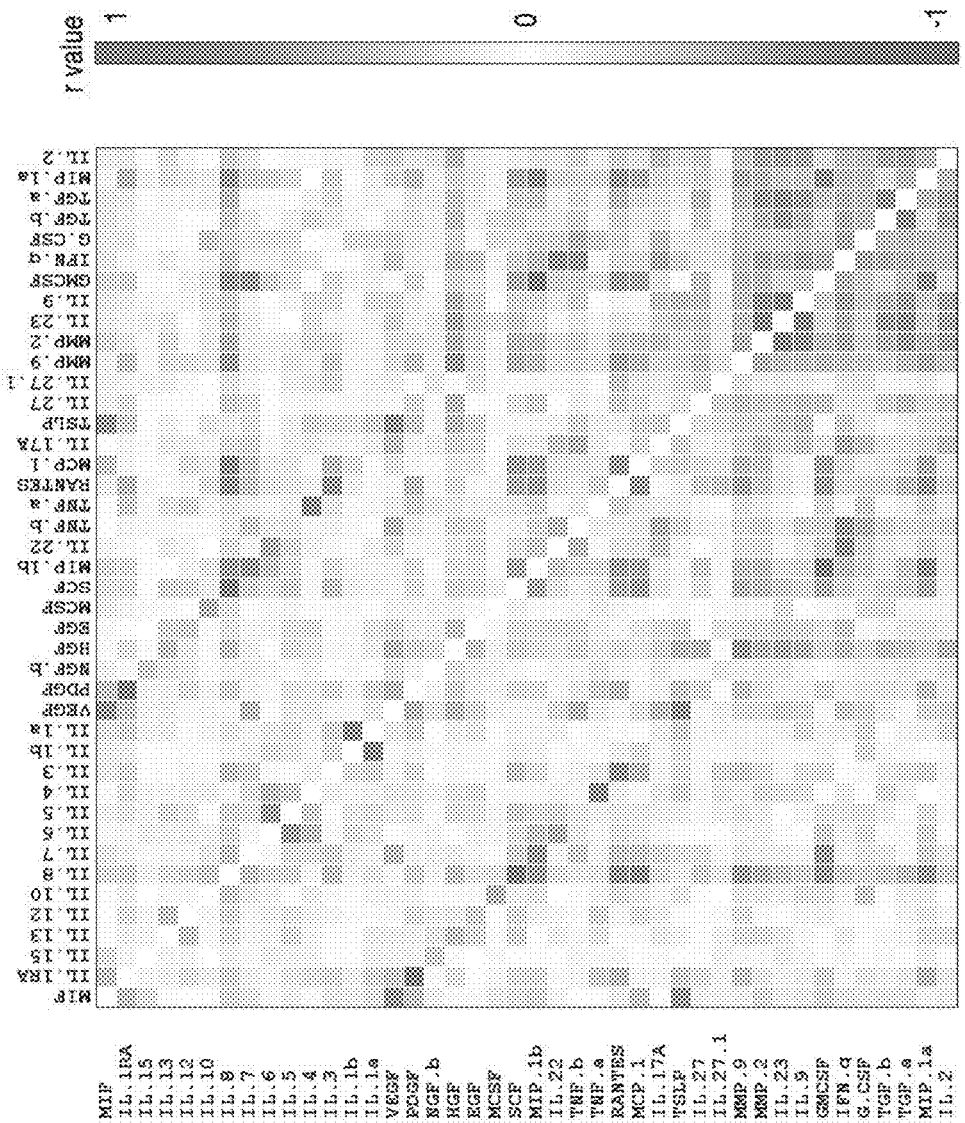
FIG. 26 is a correlation map analysis of a 45-plexed cytokine, chemokine, and extracellular protein (e.g, growth factor) 3-color spectral detection using the device of the invention.

As detailed herein, the device and method of the invention allows for he multiplexed simultaneous detection of a large number of compounds. By utilizing the spatial location/shape of isolated features and different detectable labels within each feature, the invention provides simultaneous detection of, in certain embodiments, up to 20, up to 30, up to 40, up to 50, up to 75, up to 100, up to 200, or more compounds. For example, FIG. 26 depicts a correlation map of 45 compounds as detected using a device and method described herein.

Given the heterogeneity of single cells, even within a given tissue, the present method provides a powerful tool to quickly and effectively determine the presence of a plurality of phenotypes within a population. For example, the method and device of the invention allows for the determination of whether all cells share the same or similar proteomic, genomic, and/or secretomic profile, or rather if there is the presence of isolated single cells within the population which has an altered profile.

The method allows for the determination of distinct cellular phenotypes that can be used, among other things, to determine the presence of a particular harmful phenotype. Determination of profiles on a single cell basis allows for detection of particular phenotypes whose individual profile would be hidden in a population profile. Further, determination of profiles based upon the multiplexed detection of a large number of compounds can identify phenotypes that would be hidden in methods that only detect one or a few compounds.

This may be used, for example, in determining the presence of cell with a profile indicative of a cancer cell. In one embodiment, the method is used to evaluate the progression of a particular disease based upon the observed phenotypical stage of one or more single cells. In another embodiment, the method could be used to detect a particular type of cancer cell or to characterize the aggressiveness or invasiveness of a cancer cell. In another embodiment, the method could be used to detect a cell with a phenotype indicative of a metastasizing cell. For example, the multiplexed single cell profiling described herein can be used to investigate the secretomic profile of single cells from a tumor, which can identify the presence a subset of individual cells whose profile is indicative of metastasis. This therefore would allow for very early diagnoses, at stages when it would otherwise be near impossible to detect.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: High-Throughput Secretomic Analysis of Single Cells to Assess Functional Cellular Heterogeneity Secreted proteins dictate a range of cellular functions in human health and disease. Because of the high degree of cellular heterogeneity and, more importantly, polyfunctionality of individual cells, there is an unmet need to simultaneously measure an array of proteins from single cells and to rapidly assay a large number of single cells (more than 1000) in parallel. Described herein is a simple bioanalytical assay platform consisting of a large array of subnanoliter microchambers integrated with high-density capture agent microarrays for highly multiplexed protein detection from over a thousand single cells in parallel. This platform has been tested for both cell lines and complex biological samples such as primary cells from patients. Distinct heterogeneity among the single cell secretomic signatures was observed, which, for the first time, can be directly correlated to the cells' physical behavior such as migration. Compared to the state-of-the-art protein secretion assay such as ELISpot and emerging microtechnology-enabled assays, the approach described herein offers both high throughput and high multiplicity. It also has a number of clinician-friendly features such as ease of operation, low sample consumption, and standardized data analysis, representing a potentially transformative tool for informative monitoring of cellular function and immunity in patients. Further description of the data presented herein may be found in Lu et al., 2013, Anal Chem, 85(4): 2518-2556, which is herein incorporated by reference in its entirety.

The materials and methods employed in the experiments are now described.

Fabrication of Capture Agent Arrays

The mold for PDMS replica is a silicon master etched with deep reactive-ion etching (DRIE) method. It was pretreated with chlorotrimethylsilane (Aldrich) vapor overnight to facilitate PDMS release. PDMS prepolymer and curing agent (RTV615, Momentive) was mixed completely (parts A and B in 10:1 ratio) and poured onto the silicon master. Air bubbles were removed via vacuum desiccator for 1 h, and the PDMS was cured in the oven at 80° C. for 2 hrs. After curing, the PDMS layer was peeled off the mold and holes for inlet and outlet ports were punched. The device was cleaned via sonication in ethanol and 2-propanol before bonding with a poly-L-lysine microarray slide (Erie Scientific). The assembly was then baked in the oven at 80° C. for 2 hrs to strengthen the bonding. The PDMS microchip for antibody flow patterning contains 20 separate microchannels which can pattern up to 20 different antibodies respectively. The typical width and pitch of set of lines is 25 μm, 50 μm respectively in the PDMS flow patterning microchip.

For the flow patterning of the capture agent array, 1.5 μL of different antibodies were injected into microchannels separately and flowed through the microfluidic channels until dry. All the antibodies used in experiments are summarized in Table 1. Antibodies are immobilized on the poly-L-lysine glass slide to form the capture agent array. After flow patterning, the glass slide can be stored in the refrigerator at 4° C., and the PDMS layer will be released before use.

TABLE 1

List of all antibodies used

| Primary antibody (vendor: clone)(catalog No.) | Secondary antibody (vendor: clone) (catalog No.) |
| --- | --- |
| Mouse Anti-Human IFN gamma (ebio: NIB42)(14-7318) | Anti-Human IFN gamma Biotin(ebio: 4S.B3)(13-7319) |
| Anti-Human TNF alpha Purified(ebio: MAb1)(14-7348) | Anti-Human TNF alpha Biotin(ebio: MAb11) (13-7349) |
| Rat Anti-Human IL-2(ebio: MQ1-17H12)(14-7029) | Rabbit Anti-Human IL-2 Biotin(ebio: Polyclonal) (13-7028) |
| Mouse Anti-Human IL-4(ebio: 8D4-8) (14-7049) | Mouse Anti-Human IL-4 biotin(ebio: MP4-25D2)(13-7048) |
| Anti-human IL-1b(ebio: CRM56)(16-7018) | Mouse Anti-Human IL-1 beta Biotin(ebio: CRM57)(13-7016) |

TABLE 1-continued

List of all antibodies used

| Primary antibody (vendor: clone)(catalog No.) | Secondary antibody (vendor: clone) (catalog No.) |
|---|---|
| Mouse Anti-Human TNF beta(ebio: 359-238-8)(14-7329) | Mouse Anti-Human TNF beta Biotin(ebio: 359-81-11) (13-7327) |
| Mouse anti-human RANTES(R&D) (DY278) | Goat anti-human RANTES(R&D) (DY278) |
| Rat Anti-Human IL-6(ebio: MQ2-13A5) (14-7068) | Rat Anti-Human IL-6 biotin(ebio: MQ2-39C3)(13-7068) |
| Rat Anti-Human IL-10(ebio: JES3-9D7)(14-7108) | Rat Anti-Human IL-10 biotin(ebio: JES3-12G8)(13-7109) |
| Mouse Anti-Human IL-12(ebio: B-T21 (BT21))(14-7128) | Mouse Anti-Human IL-12 biotin(ebio: C8.6)(13-7129) |
| Anti-Human GMCSF(BD)(555126) | Anti-Human GMCSF biotin(BD)(555126) |
| Mouse Anti-CCL2 (MCP-1)(ebio: 5D3-F7)(14-7099) | Armenian Hamster Anti-CCL2 (MCP-1) Biotin(ebio: 2H5)(13-7096) |
| Mouse Anti human EGF(R&D) (DY236) | Goat Anti human EGF Biotin (R&D) (DY236) |
| Mouse Anti human FGF basic(R&D) (DY233) | Mouse Anti human FGF basic Biotin (R&D) (DY233) |
| Mouse Anti human HGF (R&D) (DY294) | Goat Anti human HGF Biotin (R&D) (DY294) |
| Mouse Anti human PDGF-AB (R&D) (DY222) | Goat Anti human PDGF-AB Biotin (R&D) (DY222) |
| Goat Anti human TGF-a Biotin (R&D) (DY239) | Goat Anti human TGF-a Biotin (R&D) (DY239) |
| Mouse Anti human VEGF (R&D) (DY293B) | Goat Anti human VEGF Biotin (R&D) (DY293B) |
| Mouse Anti human MIF (R&D) (DY289) | Goat Anti human MIF Biotin (R&D) (DY289) |
| Rat Anti-Human IL-5(ebio: TRFK5)(14-7052) | Rat Anti-Human IL-5 biotin(ebio: JES1-5A10)(13-7059) |
| Mouse Anti-Human IL-13(ebio: PVM13-1)(14-7139) | Rabbit Anti-Human IL-13 biotin(ebio: Polyclonal)(13-7138) |

Fabrication of Sub-Nanoliter Microchamber Array Chips

The mold for the sub-nanoliter microchamber array is a silicon master etched with DRIE method. It was also pre-treated with chlorotrimethylsilane (Aldrich) vapor overnight to facilitate PDMS release. The sub-nanoliter microfluidic chamber array chips for single cell capture were fabricated out of PDMS (RTV615, Momentive, parts A and B in 10:1 ratio) using soft lithography techniques. Air bubbles were removed via vacuum desiccator for 1 h, and the PDMS was cured in the oven at 80° C. for 2 hrs. The sub-nanoliter microchamber array chips contain 5044 cell capture chambers in 14 columns with approximately 550 microwells per column. Image "markers" are included on the lithography mask for automated microwell and cell recognition at distinct spatial locations on the resultant microwell array Cell Culture and Stimulation Human A549 cell line was cultured in F12/K medium supplemented with 10% fetal bovine serum (FBS, ATCC). Human U937 cell line was purchased from ATCC (American Type Culture Collection, ATCC) and cultured in RPMI 1640 medium (Gibco, Invitrogen) supplemented with 10% fetal bovine serum (FBS, ATCC). Every 100 uL of U937 cell suspension was differentiated with 1 µL 20 µg/mL phorbol 12-myristate 13-acetate (Fisher) and challenged by 1 µL 1 mg/mL lipopolysaccharide (Calbiochem) to activate Toll-like receptor 4 (TLR4) signaling before its suspension was pipetted onto PDMS microwell array.

Human Tissue Specimens

Human samples were obtained from individuals with meningioma. Patient primary tissue was first minced with a scalpel and then placed in 1× TrypLE Select (Invitrogen). Tissue was triturated with fire-polished glass pipettes and allowed to incubate for 5 mins at 37° C. The cell suspension was triturated again with fire-polished glass pipettes and allowed to incubate for another 5 mins at 37° C. The cell suspension was then strained through a 40 µm cell strainer (BD Falcon) and washed with DMEM-F12 (Gibco, Invitrogen). The suspension was then centrifuged at 300 RCF for 5 min. The pellet was resuspended in DMEM-F12. Red blood cell lysis solution (Miltenyi Biotec) was then used to remove erythrocytes and centrifuged at 300 RCF for 5 min. The cells were then resuspended in DMEM-F12 at $10^6$ cells/mL.

Single Cell Trapping with PDMS Microwell Array

Before performing the single cell trapping experiment, the PDMS microwell array and capture agent array glass slide was blocked with 3% BSA solution (Sigma) respectively for 2 hrs and then rinsed with fresh cell medium. Cells were suspended in fresh medium just before cell capture. The PDMS microwell array was placed facing upward and cell culture medium solution was removed until a thin layer was remained on the PDMS microwell array surface. Cell suspension was pipetted (50-200 µL) onto the microwell array and allowed to settle for 10 mins so that cells would fall into the microwells. The antibody glass slide was put on the top of PDMS microwell array with capture agent array resting on the cell capture chambers. Then the PDMS microwell array and glass slide were clamped tightly with screws and pressure was distributed by springs. Single cells will be trapped in the microwell array and the assembly was allowed to incubate for 24 hours to allow for cell secretion. After the trapped cells were incubated for 24 hours, the screws were released to remove the capture agent array glass slide, and ELISA immunoassay procedures were performed and the results were detected and analyzed with Genepix scanner and software.

Population Micro Array

Cell population assay was performed on custom printed antibody microarray, which was spotted with a Spotbot 3 microarrayer (Arrayit) on poly-L-lysine glass slides. Twelve identical subgroups which had the same antibody pattern were printed on each glass slide. After printing, the antibody glass side was kept in a wet box (containing saturated NaCl solution at 75% relative humidity) for 5 hours. Before cell population assay, the glass side was bonded with a PDMS microwell slab and blocked with 3% BSA solution for 2 hours. Then cell culture supernatant was added into different microwells and allowed to incubate for 1 hour. Following incubation, ELISA immunoassay procedures are performed, and the results were detected and analyzed with Genepix scanner and software.

Immunoassay Procedures

ELISA procedures were followed to translate secreted cytokines by single cells into detectable signals. A mixture of biotinylated detection antibodies (Table 1) were pipetted onto the glass slide and incubated for 45 min at room temperature to complete the sandwich immunoassay followed by washing with 3% BSA solution. APC dye-labeled streptavidin (eBioscience, 200 µL, 5 µg/mL) was added onto glass slide and incubated for another 45 min. Following, the glass slide was washed with 3% BSA again and blocked with 3% BSA for 0.5 hr. Following the BSA blocking, the glass slide was dipped in DPBS, DPBS, DI water, DI water sequentially and finally blown dry.

Fluorescence Detection and Analysis

Genepix 4000B and 4200A scanners (Molecular Devices) were used to obtain scanned fluorescent images for FITC and APC channels. Two color channels 488 (blue) and 635 (red) were used to collect fluorescence signals. The image was analyzed with GenePix Pro software (Molecular Devices) by loading and aligning the microwells array template followed by extraction of fluorescence intensity values. Fluorescence results were extracted with the image analysis tool in GenePix Pro. The fluorescence results were then matched to each of the chambers of the sub-nanoliter microchamber array chips analyzed via optical imaging.

Automated Optical Image Analysis and Cell Counting

The assembly was imaged on an automatic microscope stage (Prior) to acquire optical images recording the number and location of cells in each microwell. Automated whole chip optical images were taken with a Paxcam (Paxit!) attached to a Nikon Diaphot SA optical microscope (Nikon), and stitched together using Paxit software (Paxit!). After imaging, the assembly was put into an incubator at 37° C. for 24 hrs to allow for cell secretion. After 24 hours of incubation, cells are imaged again to observe cell function. A home developed software using OpenCV (Intel) was written to automate cell counting, and the cell counts were matched with the extracted fluorescent data to their respective cell chambers.

Data and Statistical Analyses

All fluorescent scanned arrays were processed with Genepix software to extract background subtracted average fluorescent signal for all features in each set. A home developed Matlab (MathWorks) code was created for automated extraction of fluorescent data and generation of scatterplots. Excel (Microsoft) and OriginPro 8 (OriginLab) was used to compile extracted data. Heatmaps and unsupervised clustering were generated from the extracted data using the software Cluster/Treeview (Eisen Laboratory). Statistical analysis was conducted in Excel, OriginPro 8, and R (R Development Core Team).

The results of the experiments are now described.

Described herein is a high-throughput single-cell secretomic analysis platform that integrates a subnanoliter microchamber array and high-density capture agent array for simultaneous detection of 14 cytokines from more than a thousand single cells in parallel. The chip can be executed in a simple assay "kit" with no need for sophisticated fluid handling or bulky equipment. The utility of this device is demonstrated for analyzing the secretion of human cell lines and primary cell samples dissociated from the fresh tumor of patients. The results reveal that there is distinct heterogeneity among the single cell secretomic signatures of a population and that the correlations obtained between the various proteins studied are in agreement with their functional classifications. This technology diverges from prior works of antibody barcode-based protein secretion measurement technique (Ma et al., 2011, Nat Med 17(6):738-43) by using simplified schemes of cell capture (Balaban, et al, 2004, Science 305(5690):1622-5), quantification, automated data analysis, and eliminating bulky fluid handling systems, resulting in a truly practical and informative tool that may find immediate use in both laboratory research and clinical diagnosis.

Design, Fabrication, and Assembly of a Single-Cell Secretomic Analysis Chip

Figure 6:
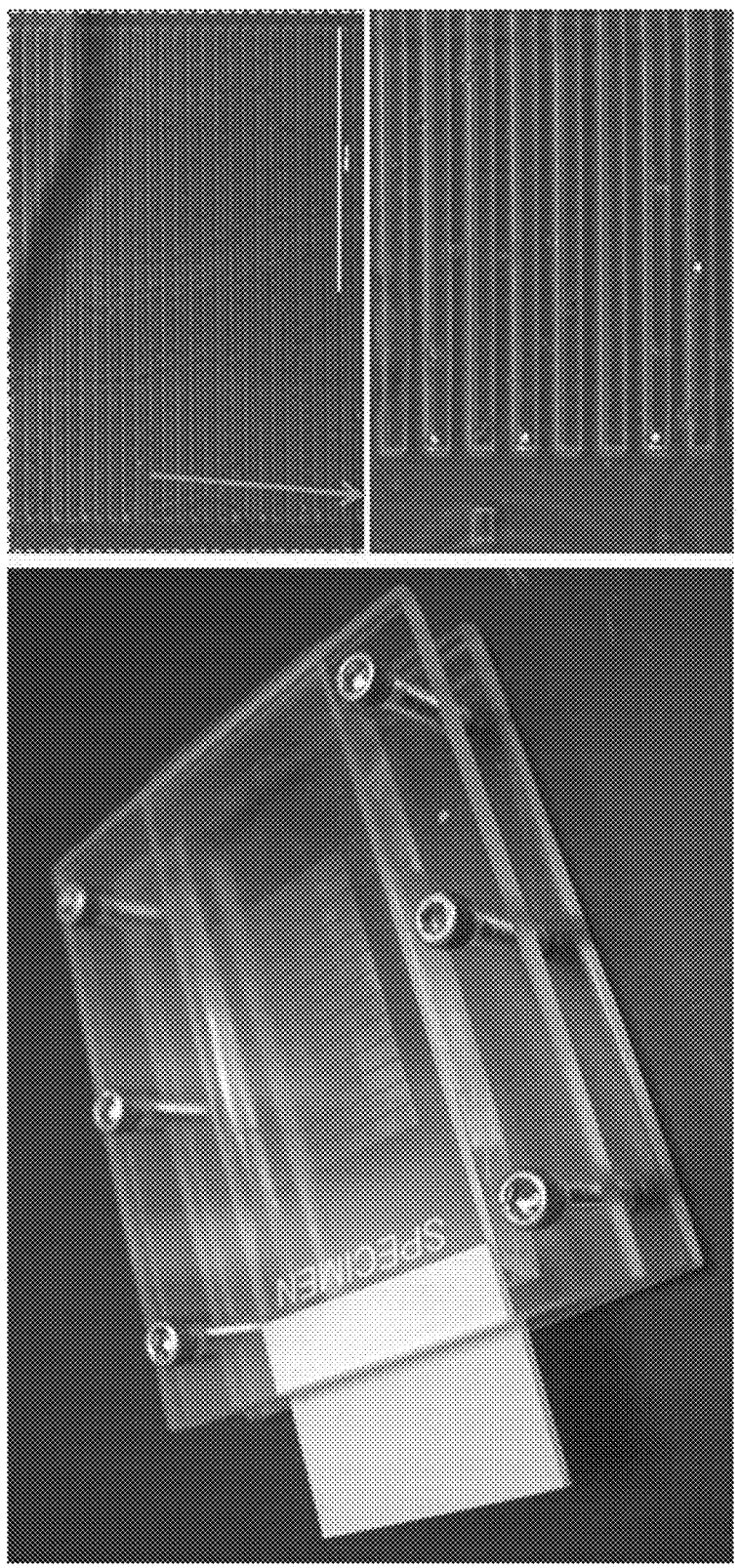
FIG. 6 is a set of images depicting the assembly of an exemplary complete single cell secretomic analysis device. A high-density antibody array glass slide and a 5440-microchamber PDMS slab were clamped together with two transparent plates using a device housing system containing a clamp with exerted spring force.

The single-cell secretomic analysis device consists of two separate parts (FIG. 1A): a high-density capture agent array glass substrate for surface-bound immunoassay and a sub-nanoliter microchamber array for capture of single cells. The capture agent array slide comprises 30 repeats of features, each of which contains up to 20 stripes of different antibodies, immobilized on a poly-L-lysine-coated surface. The antibody stripes are 20 µm in width and the pitch size of a full array is 1 mm. The microchamber array is a one-layer microchip fabricated by soft lithography (Unger et al., 2000, Science 288(5463):113-6) from polydimethylsiloxane (PDMS) (Unger et al., 2000, Science 288(5463):113-6), an optically transparent silicone elastomer widely used for biological microfluidics. It contains 5440 rectangular microchambers, each of which is 1.8 mm, 20 µm, and 15 µm, in length, width, and depth, respectively. These two parts were manufactured independently and combined during the assay such that the capture agent array slide acts as a disposable test strip and the microchamber array as a reusable device. To use this platform, a drop of single cell suspension (~$10^6$ cells/mL) is directly pipetted onto the surface of the microchamber array chip. The cells fall into the microchambers by gravity, and then the aforementioned capture agent array slide is placed antibody-side down on top of the microchambers such that the lines are perpendicular to the length of the microchambers. The microchamber is designed to be sufficiently long as to contain at least a full set of features, thereby eliminating the need for precise alignment. Finally this assembly is fixed by two transparent plastic plates with four spring-adjusted screws (FIG. 6) and placed in a conventional tissue incubator for single-cell secretion measurement. Proteins secreted from individual cells are captured by the capture agent array and read out by incubating with biotinylated detection antibodies and then streptavidin conjugated with a fluorescence probe (e.g., Cy5). As compared to the prototype single cell proteomic chip (Ma et al., 2011, Nat Med 17(6):738-43), this setup does not require a sophisticated microfluidic control system or any bulky equipment to operate and thus is more amenable to widespread use by researchers and clinicians with minimal engineering background.

Figure 7:
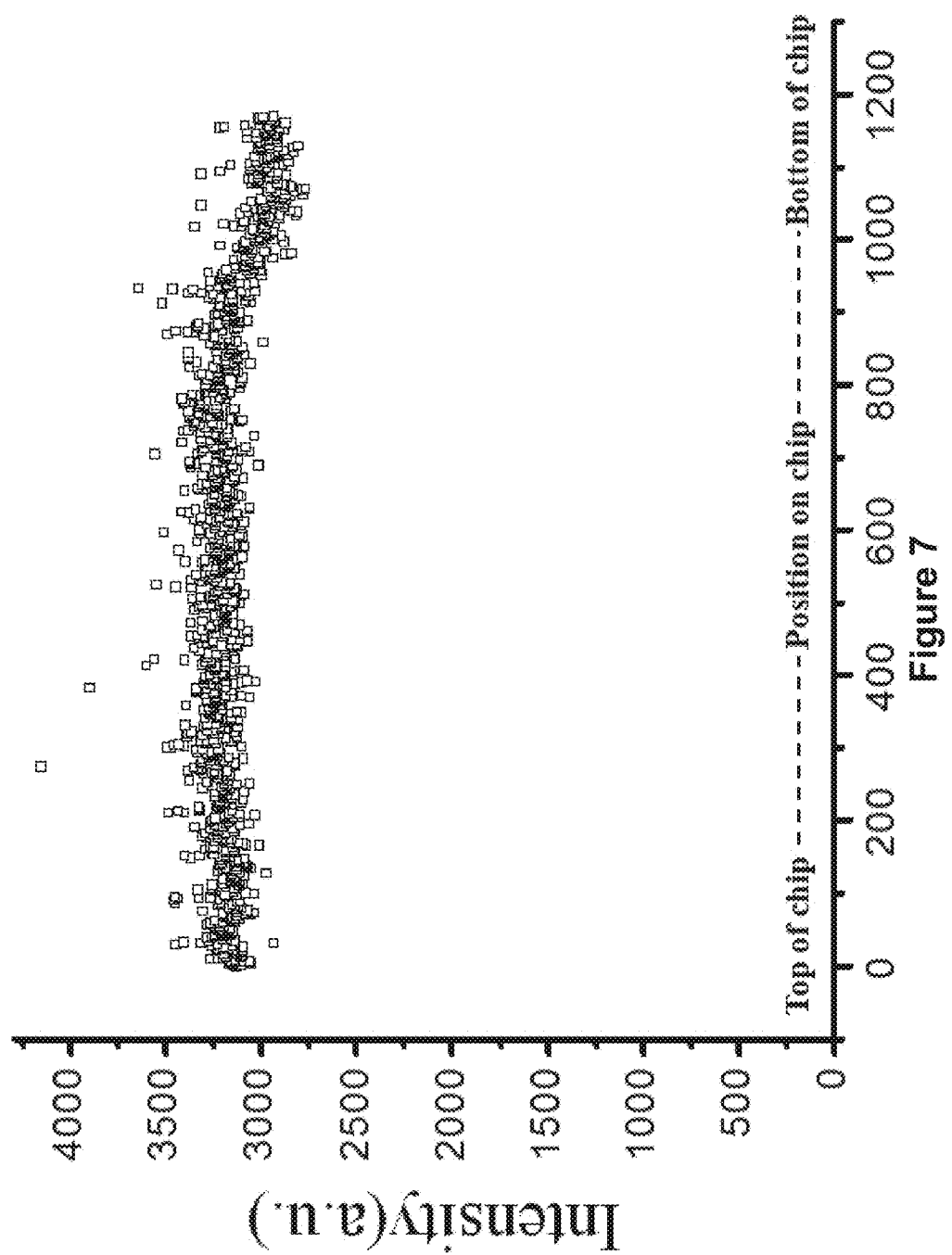
FIG. 7 is a graph depicting the evaluation of the whole chip uniformity of the capture agent array. Quantification of fluorescence intensity across the flow patterned poly-L-lysine slide (3 cm×2 cm) reveal excellent uniformity of the immobilized proteins (FITC-BSA), which ensures the validity of using this high-density array technology to assess single cell heterogeneity.

The high-density capture agent array is fabricated using a well-established microchannel guided patterning technique (Fan et al., 2008, Nat Biotechnol 26(12):1373-8), and in principal can be created by several other high-density microarray printing techniques such as inkjet printing or nanoscale tip-based spotting. The flowpatterning chip is a separate PDMS slab that has inlets leading to 20 individual serpentine microchannels in which individual antibody solutions (1 µL each) are precisely metered, added, and flowed through all microchannels in parallel to ensure uniform loading of antibodies on the surface. Fluorescein isothiocyanate labeled bovine serum albumin (FITC-BSA) solution was used to evaluate the patterning quality. The result shows successful fabrication of high-density protein array across a large area (1 in.×2 in.) and excellent uniformity (<5% in fluorescent intensity) as revealed by the fluorescence intensity line profile (FIG. 1B and FIG. 7). This ensures the observed protein signal variations (>10%) from the following single cell secretomic assays are attributed to cellular heterogeneity, rather than the nonuniformity of the starting capture agent array.

Figure 8:
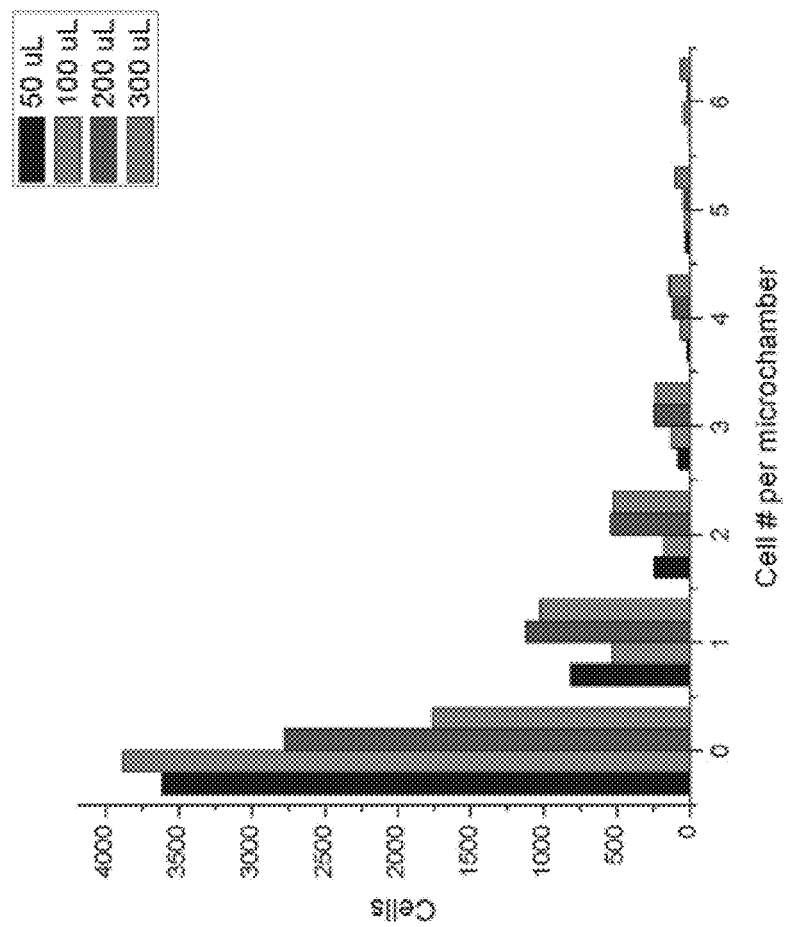
FIG. 8 is a graph depicting the distribution of the number of cells across a whole microchip. Four experiments were performed with different quantities of cell suspensions (cell density: $10^6$ cells/mL).

A motorized phase-contrast imaging system has been developed to image all cells in the cell capture chip within 10 min (FIG. 1C), and an image analysis algorithm allows for identification of individual cells and their x/y coordinates and counting of cells in each microchamber. The simple microchamber array chip format was chosen because it is easy to operate, but as a consequence it is not possible to ensure that one cell is captured per chamber. However, optimization of cell density in the stock solution readily gives rise to more than 1000 single cell chambers in a microchip (FIG. 8), permitting high-throughput analysis of single cells.

Protein Panel and Validation

The proteins assayed by the capture agent array are listed in FIG. 2A. Assessment of these particular proteins secreted from single cells is of particular importance due to their functions in a range of cellular processes (Raman et al., 2007, Cancer Lett 256(2):137-65; Wu et al., 2012, PLoS Comput Biol 8:e1002355; Zou, 2005, Nat Rev Cancer 5(4):263-74; Dranoff 2004, Nat Rev Cancer 4(1):11-22). They include cytokines, chemokines, and growth factors involved in a wide range of immunological or pathophysiological processes. Assessment of these proteins secreted from single cells is of importance in the study of cellular immunity and cell-cell signaling networks. In order to simultaneously measure these proteins from single cells, capture antibodies are immobilized on the substrate as a high-density capture agent array. Prior to performing single-cell analysis, the assay was validated using recombinant proteins. Individual recombinant protein was spiked into fresh cell culture medium over a 4-log range of concentrations and exposed to the full panel of antibodies in order to assess cross-reactivity, the limit of detection (LOD), and dynamic range. The antibodies with cross-reactivity over 5% (at 5 ng/mL of protein concentration) is eliminated or replaced. Ultimately a panel of antibody pairs were obtained as summarized in Table 1. The titration curves (FIG. 2B) demonstrate the feasibility of quantitative measurements of these proteins in the multiplexed array, with a typical measurement range of 3 orders of magnitude. The LOD ranged from 400 pg/mL to below 10 pg/mL depending on the affinity of antibody pairs. On the basis of the volume of a microchamber (~0.54 nL) and the representative detection sensitivity (~10 pg/mL), the amount of protein that can be detected by the capture agent array in a microchamber is on the order of 5.4 ag, which is approximately equal to ~160 molecules. Thus, the platform has the sensitivity to detect proteins secreted from a single cell (typical copy number ~$10^{2-5}$).

Single-Cell Protein Secretomic Analysis on Cell Lines

Figure 3A:
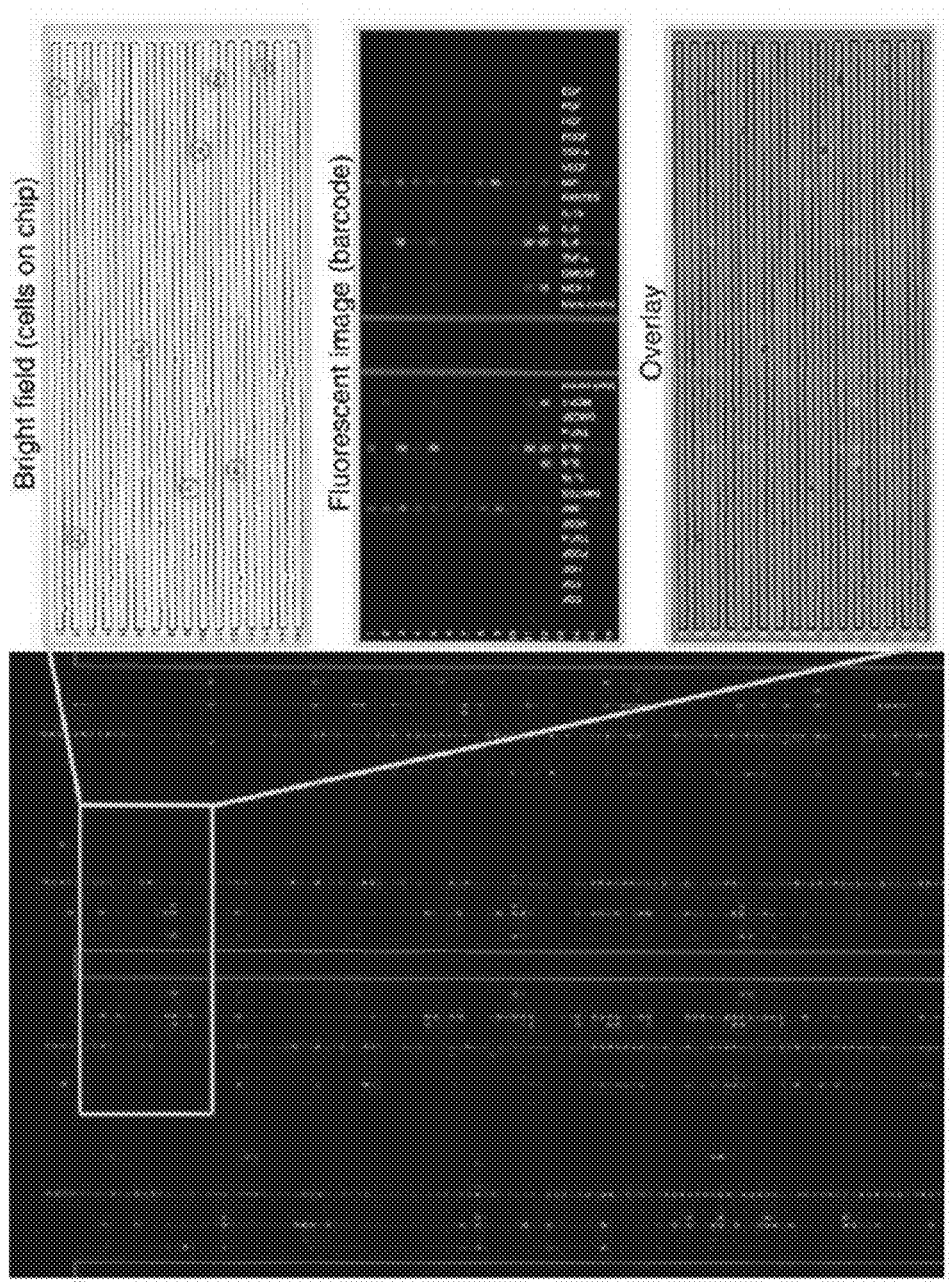
FIGS. 3A-3D show a set of images depicting the results of single-cell secretomic analysis on U87 cell lines.
Figure 9A:
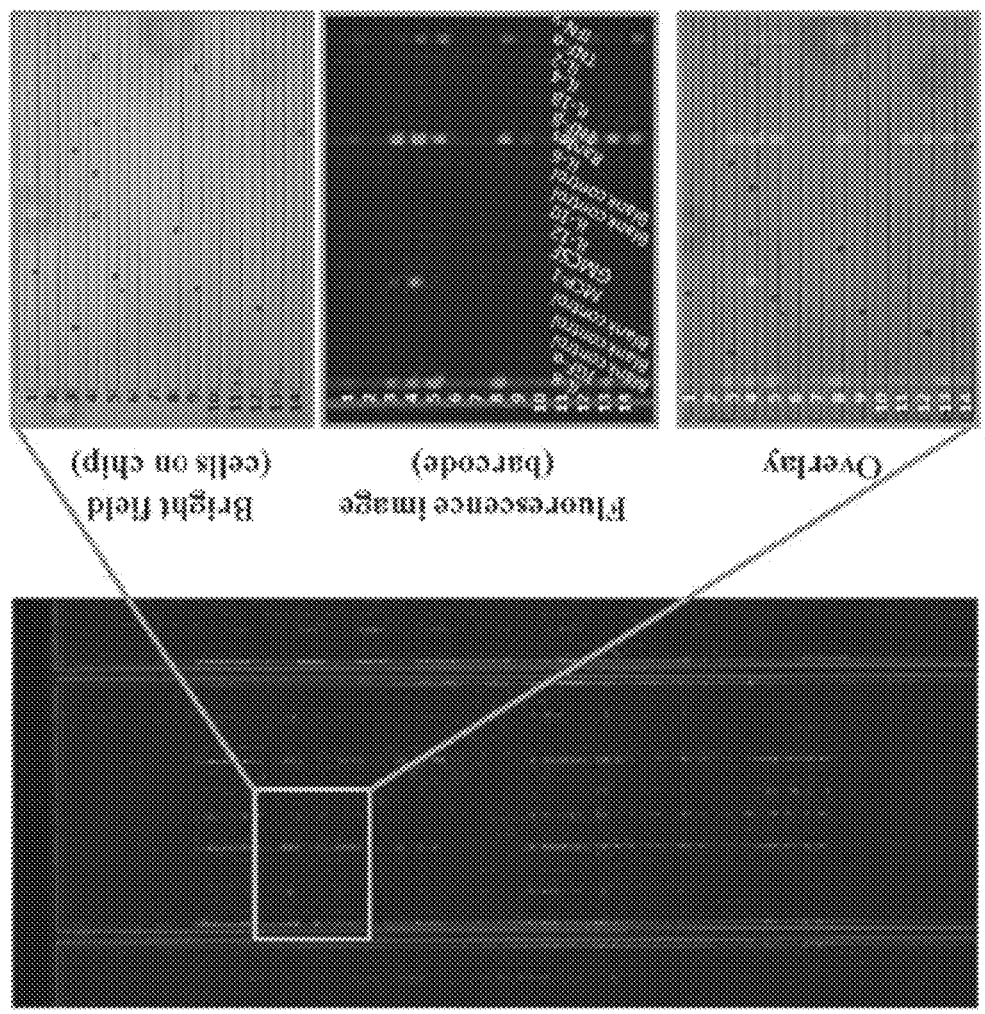
FIGS. 9A-9C show a set of images depicting the single-cell secretomic analysis on U937 cell lines.

The single-cell secretomic analysis chip was first used to measure 14 proteins from a human glioblastoma multiforme cell line (U87). In this experiment, up to 10 cells were captured in each microchamber, with 1278 of the microchambers capturing single cells. During the flow patterning of capture agent arrays, FITC-BSA (0.5 mg/mL) was always flowed in channel 1 to form a continuous line of fluorescence signal serving as both a position reference and an internal quality/uniformity control. As shown in a representative region of the scanned fluorescence image (FIG. 3A and FIG. 9A), both the blue FITC-BSA reference line and the red patterned signals corresponding to protein secretion levels are readily visible. Shown in the same figure are a bright field image of 14 microchambers with cells loaded, the corresponding fluorescent array image, and an overlay of the two. The major proteins observed after 24 h of incubation (FGF, VEGF, MIF, IL-6, IL-8, and MCP-1) are mainly pro-inflammatory cytokines or chemoattractant proteins.

Figure 3B:
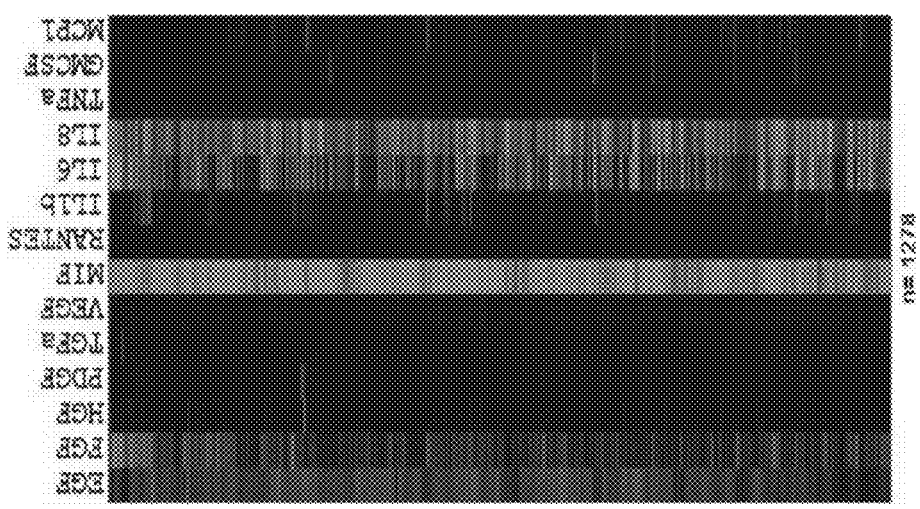
Figure 3C:
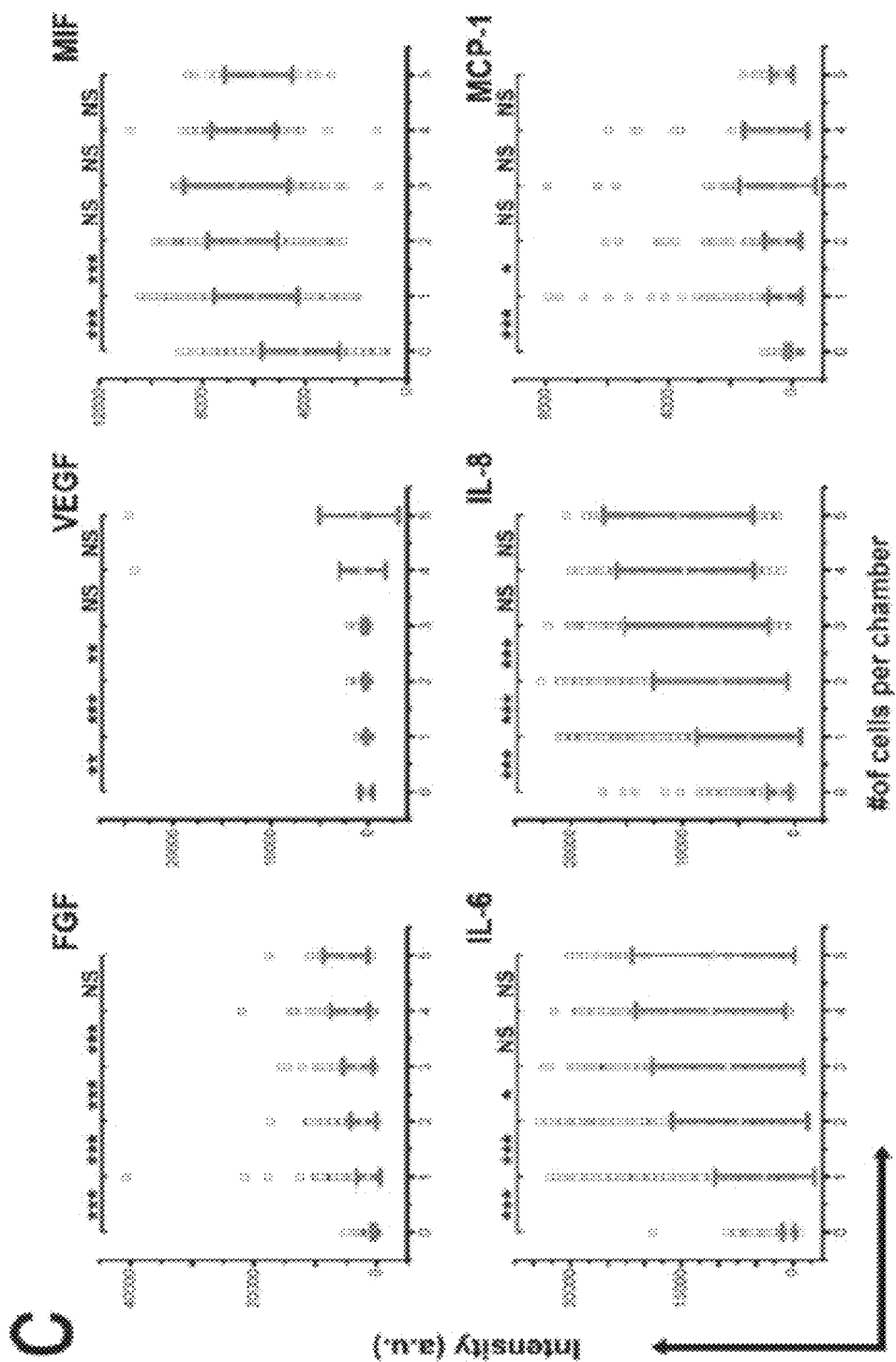
Figure 3D:
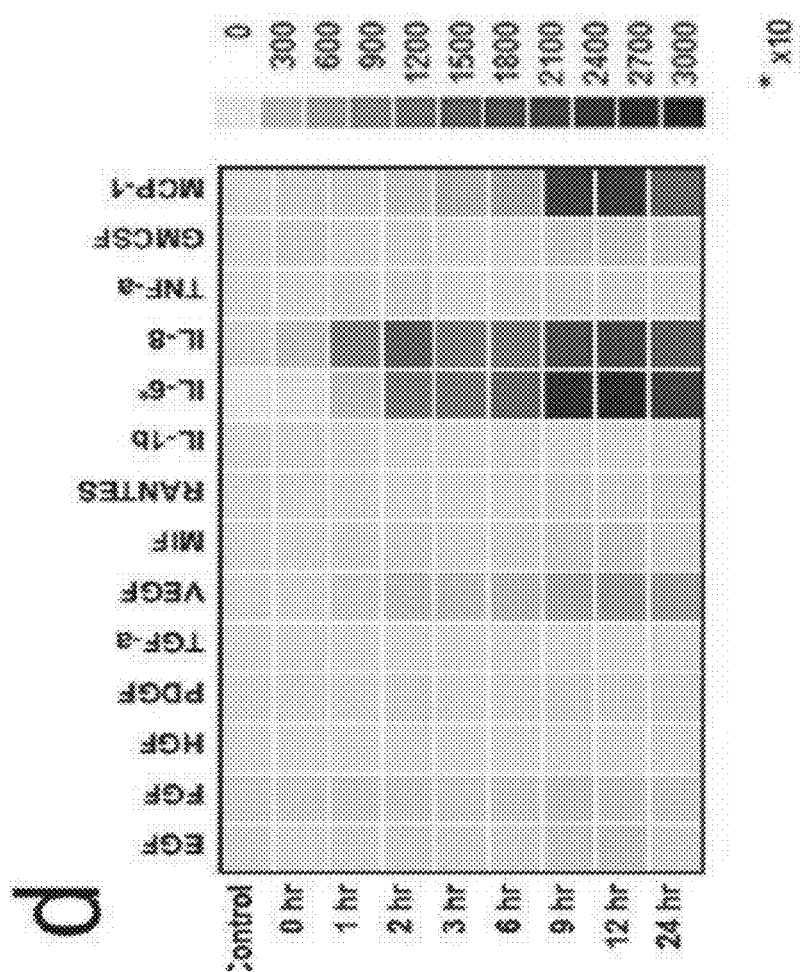
Figure 10:
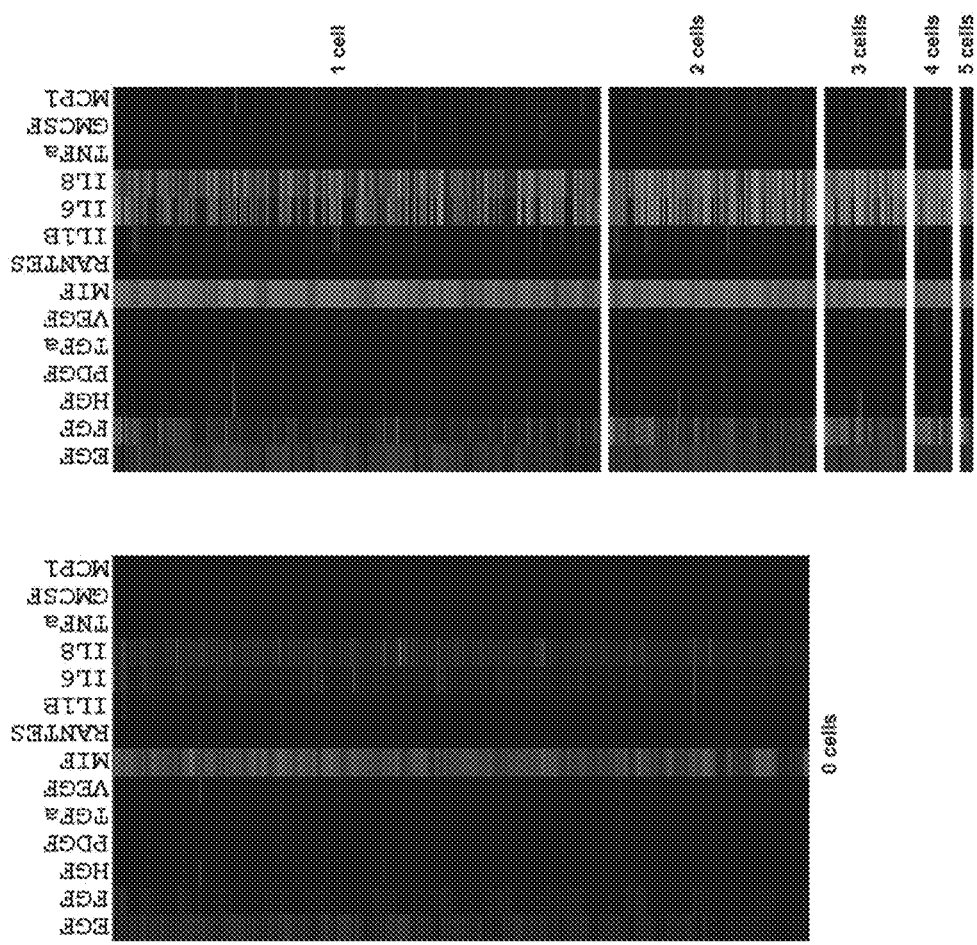
FIG. 10 is a set of heat maps that show the profile of 14 proteins secreted from chambers with U87 cell line. Each row is a cell chamber and each column corresponds to a protein of interest. Zero cells (n=1821), single cells (n=1278), two cells (n=544), three cells (n=214), four cells (n=100), and five cells (n=35).
Figure 11:
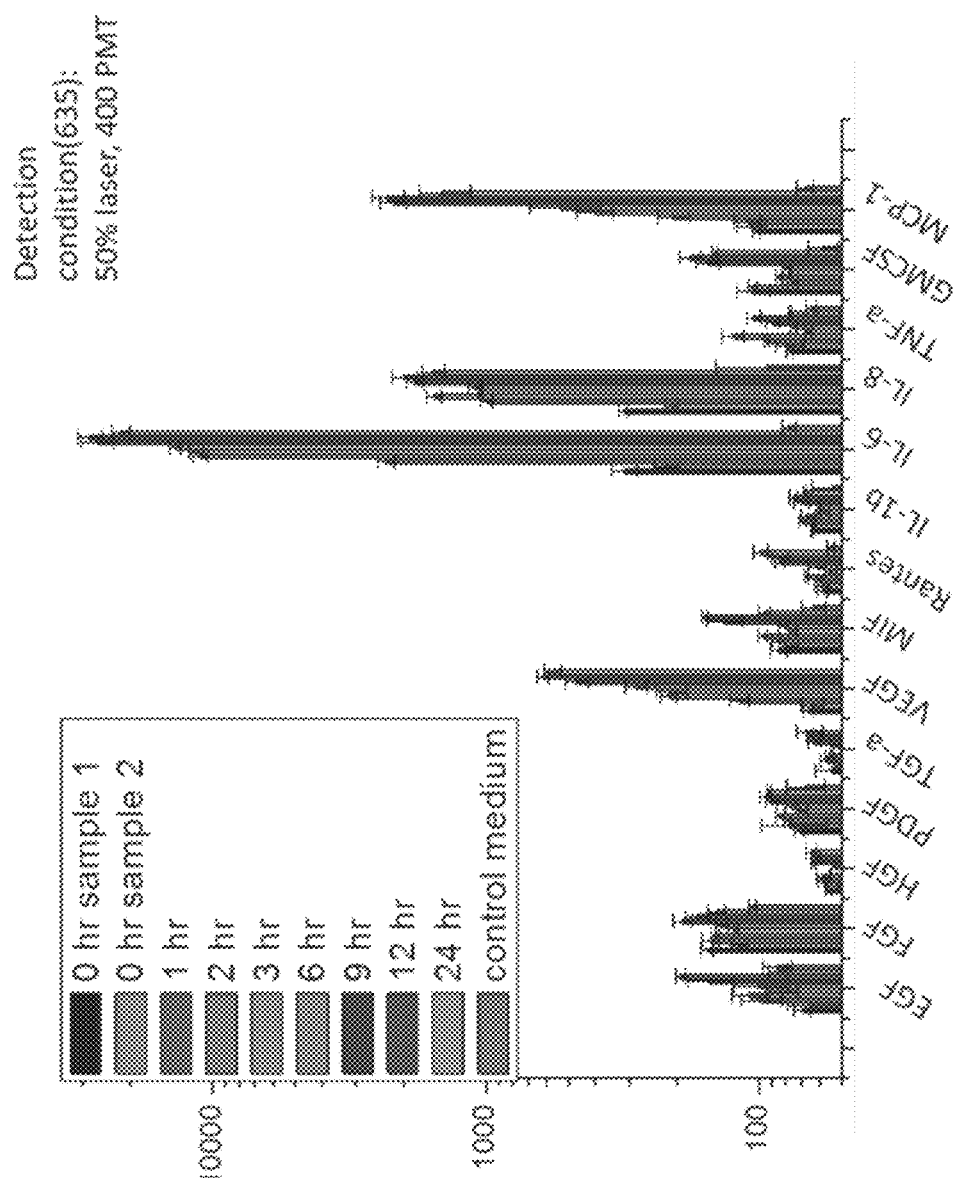
FIG. 11 is a graph depicting the population kinetics for U87 cell line. Control (MEM medium), secretion supernatant from population at different time points (0 hr, 1 hr, 2 hr, 3 hr, 6 hr, 9 hr, 12 hr, 24 hr)
Figure 12:
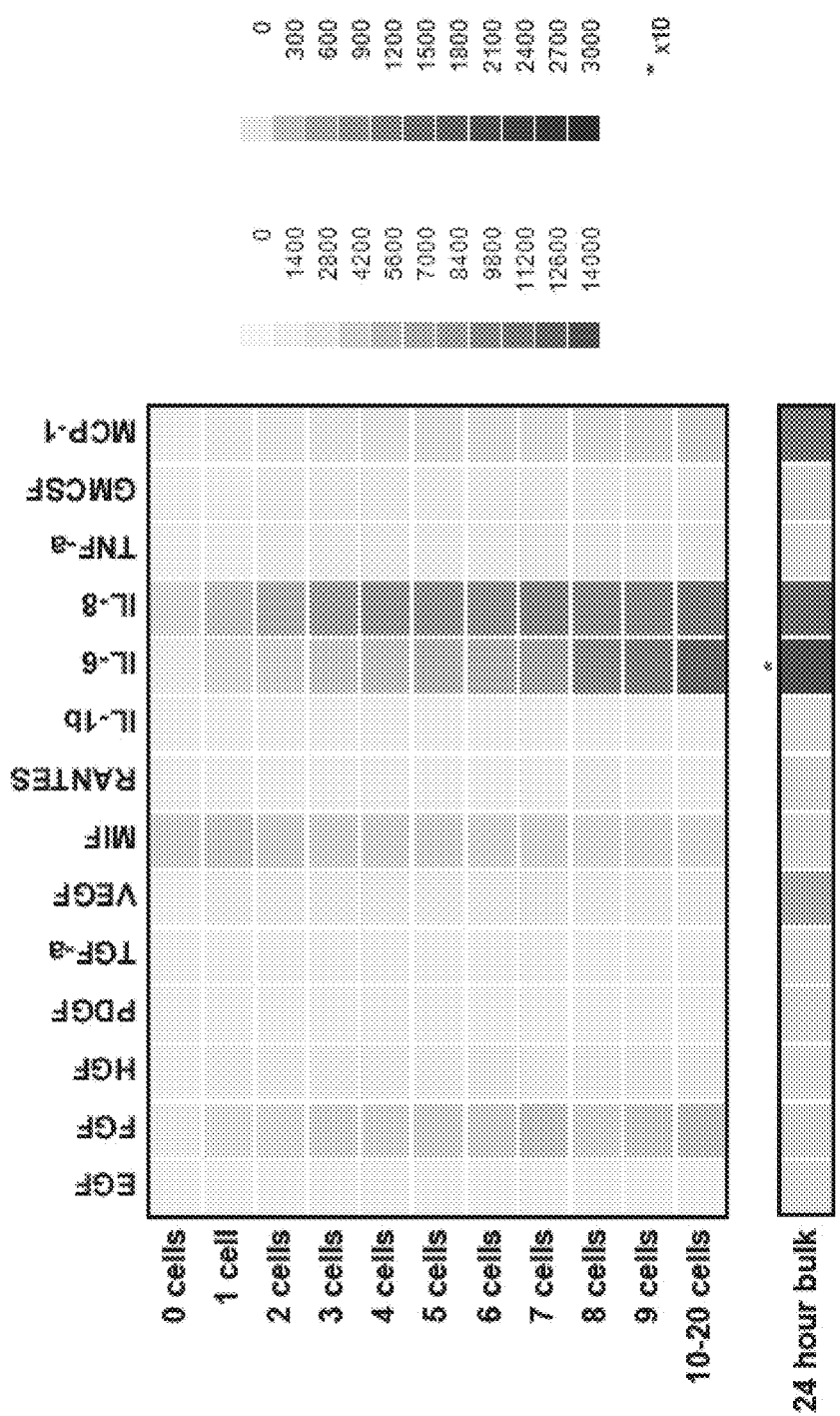
FIG. 12 is an image depicting the average. Average signal of U87 cells within the single cell platform approaching bulk patterns (top) and the 24 hour bulk secretion profile of U87 cells (bottom)

Automated quantitation of the fluorescence intensity of each protein in a microchamber was conducted using the image analysis software Genepix 6.0. The secretomic profile for only those microchambers containing single cells were extracted and a heat map of the resulting secretion profiles (FIG. 3B and FIG. 10) indicates the existence of cell-cell variation. While the majority of cells produce IL-6 and IL-8, the level of these proteins varies among individual cells and the secretion of other lower abundance proteins such as MCP-1 and FGF apparently exhibit heterogeneous signatures; only a small fraction of cells express these proteins at high levels. To verify the single cell measurements, a kinetic bulk population secretion measurement was performed in parallel on the supernatant collected from the same cells, incubated over the same time, and measured using a conventional pin-spotted microarray. The result (FIG. 3D and FIG. 11) also reveals FGF, VEGF, IL-6, IL-8, and MCP-1 as the top five proteins that are all consistent with single-cell analysis although the relative levels are different. However, MIF did not show up in the population assay. Interestingly, it was observed that the protein level as measured by fluorescence intensity is not always proportional to the number of cells and sometimes cannot be interpreted by an additive effect (FIG. 3C and FIG. 12). A secretomic analysis chip was loaded with many more cells, and MIF signal decreases with increasing number of cells in the capture chambers, revealing the possibility of paracrine signaling and the regulation of MIF with an increasing number of cells (FIG. 12). This small level of discrepancy is expected as the two assays are not biologically identical (for example, the bulk assay detects the end point protein profile while the single cell assay measures accumulated signals over the period of incubation; the population arrays are subjected to paracrine signaling while single cell measurements are not). Overall, these comparative studies are in good agreement with each other and demonstrated the validity of the single cell secretomic analysis microchip. Another advantage of this platform is that it also measures proteins secreted from multiple cells at the same time. While IL-6 and IL-8 secretion increases with increasing number of cells in a microchamber, the amount of MCP-1 or MIF increase does not change significantly when cell number exceeds 2, suggesting the existence of a possible mechanism similar to "quorum sensing" in which the paracrine mechanism in the multicellular system controls homeostasis.

Figure 9B:
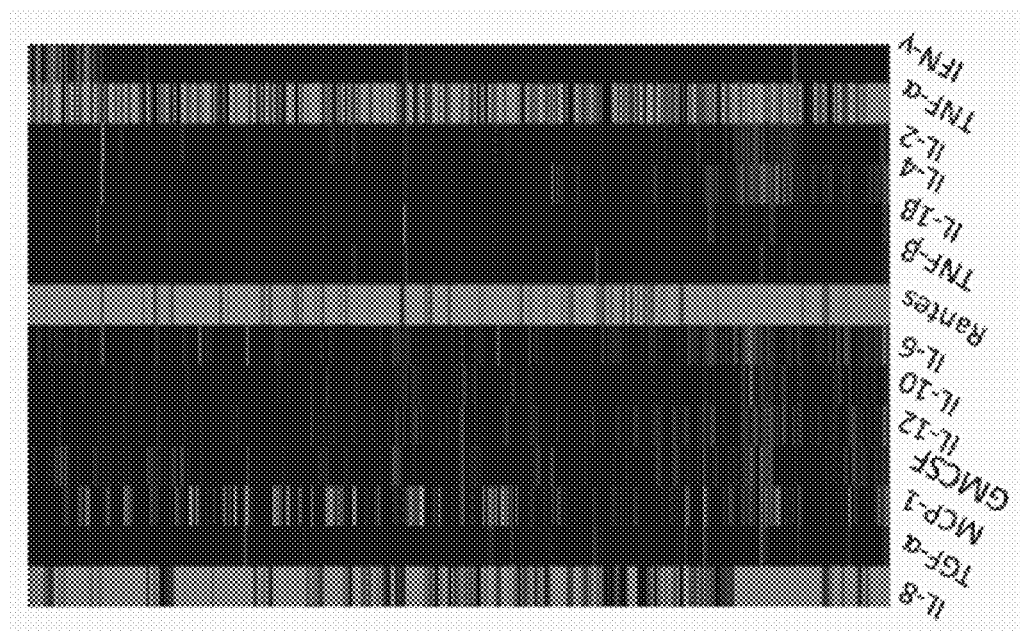
Figure 9C:
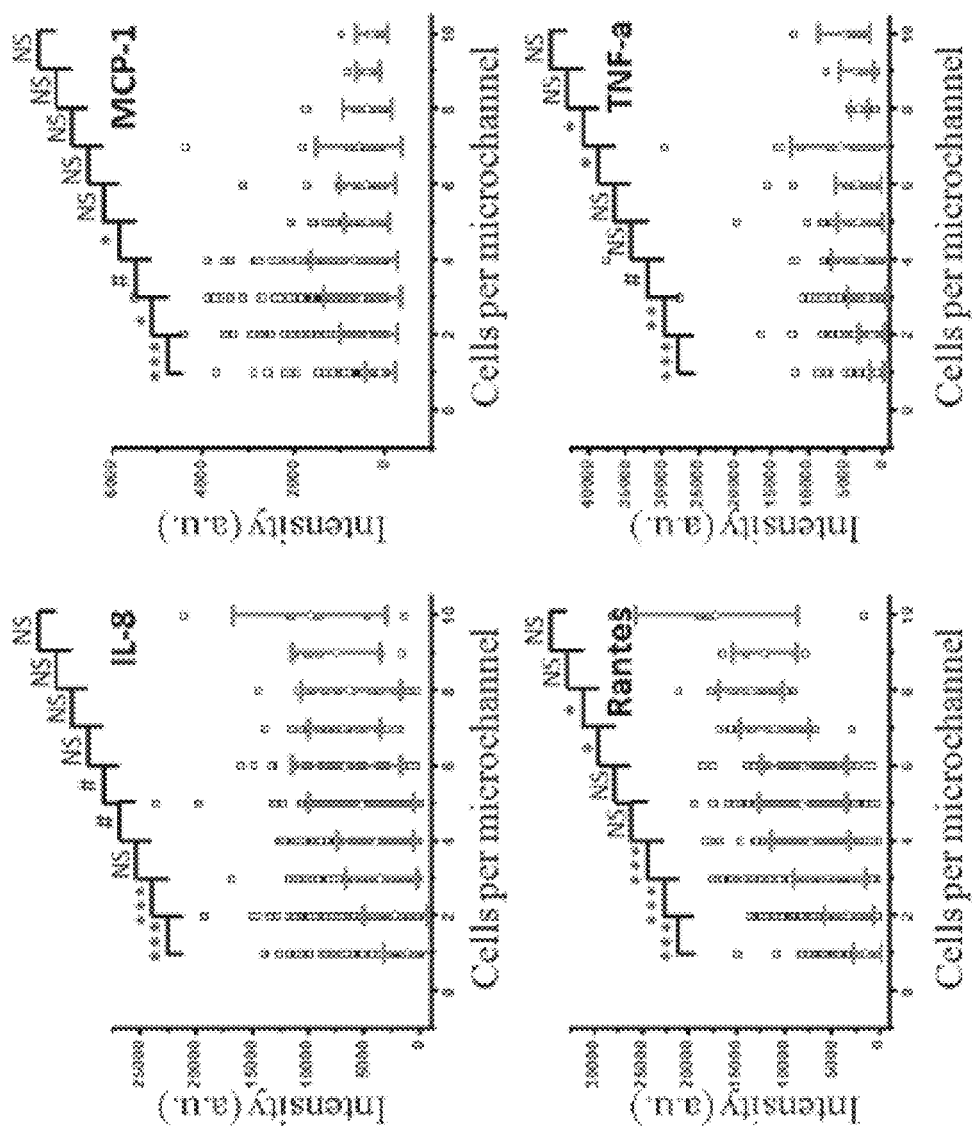
Figure 13:
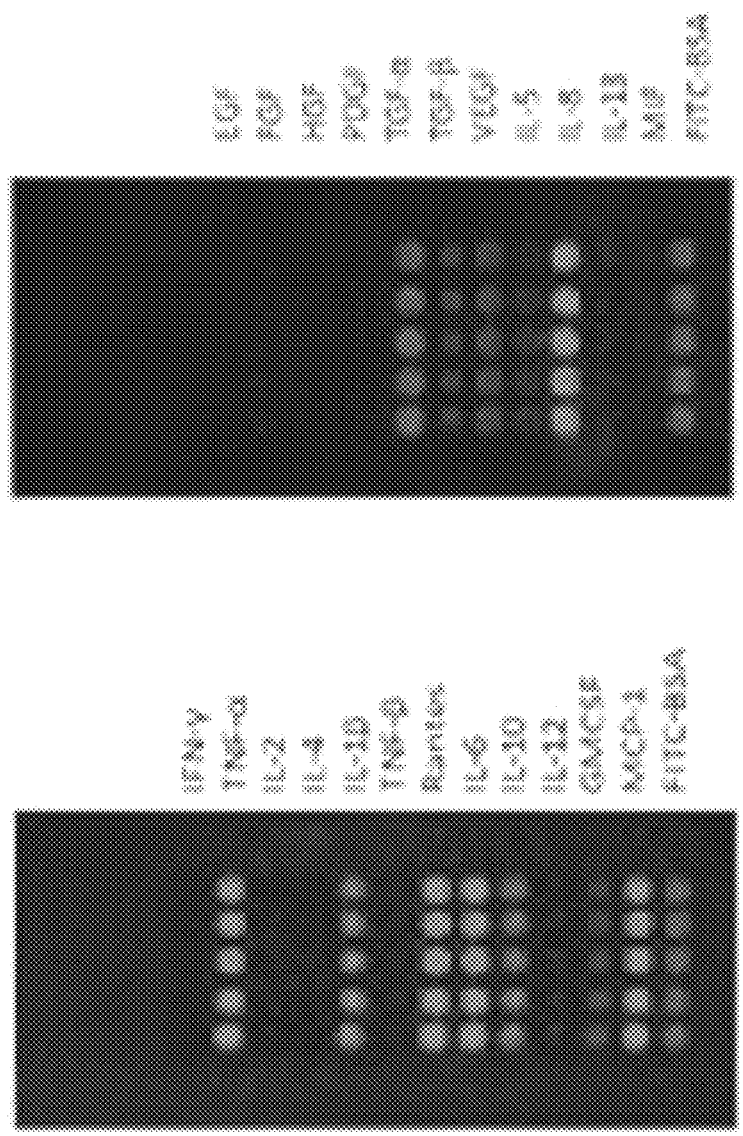
FIG. 13 is a set of images depicting the results of a control experiment measuring U937 population secretion. Proteins secreted from a large population of U937 cells were measured by a conventional antibody microarray (upper panels). Quantification of all 23 proteins are shown in the lower panel.
Figure 13:
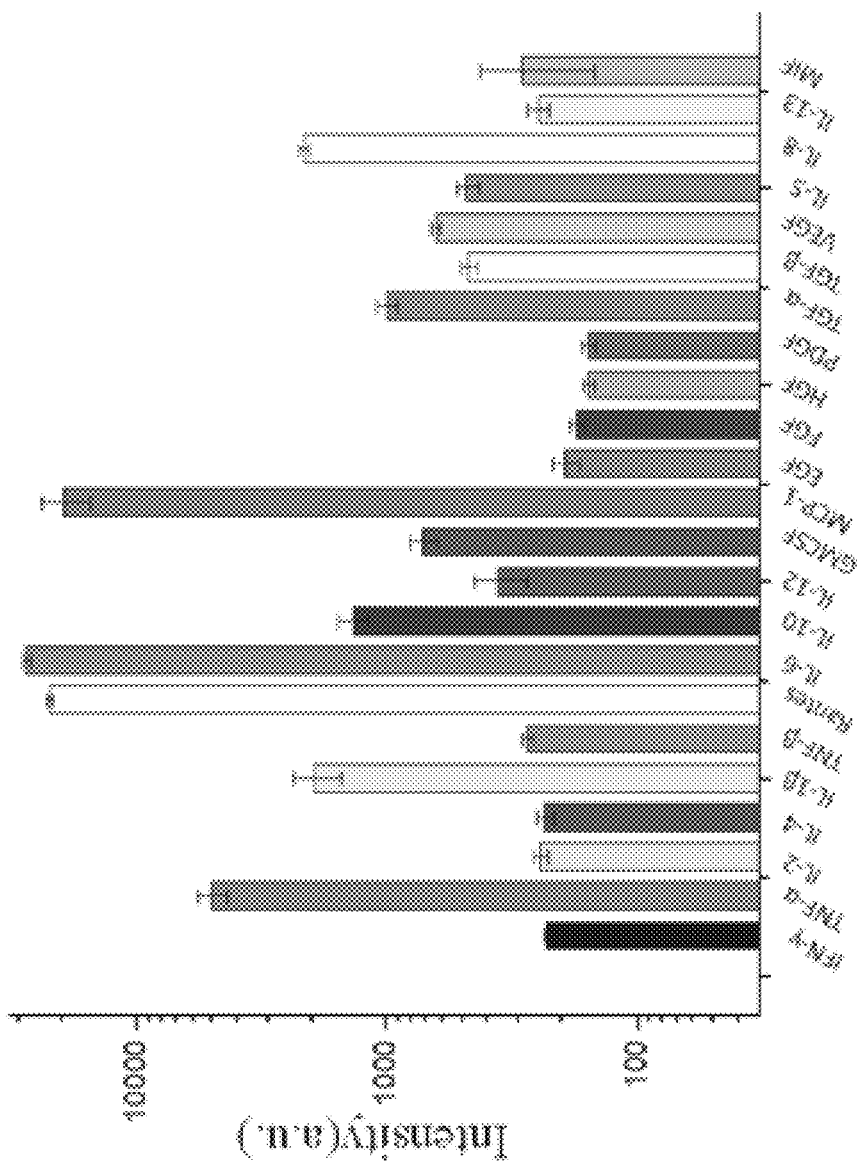
Figure 14:
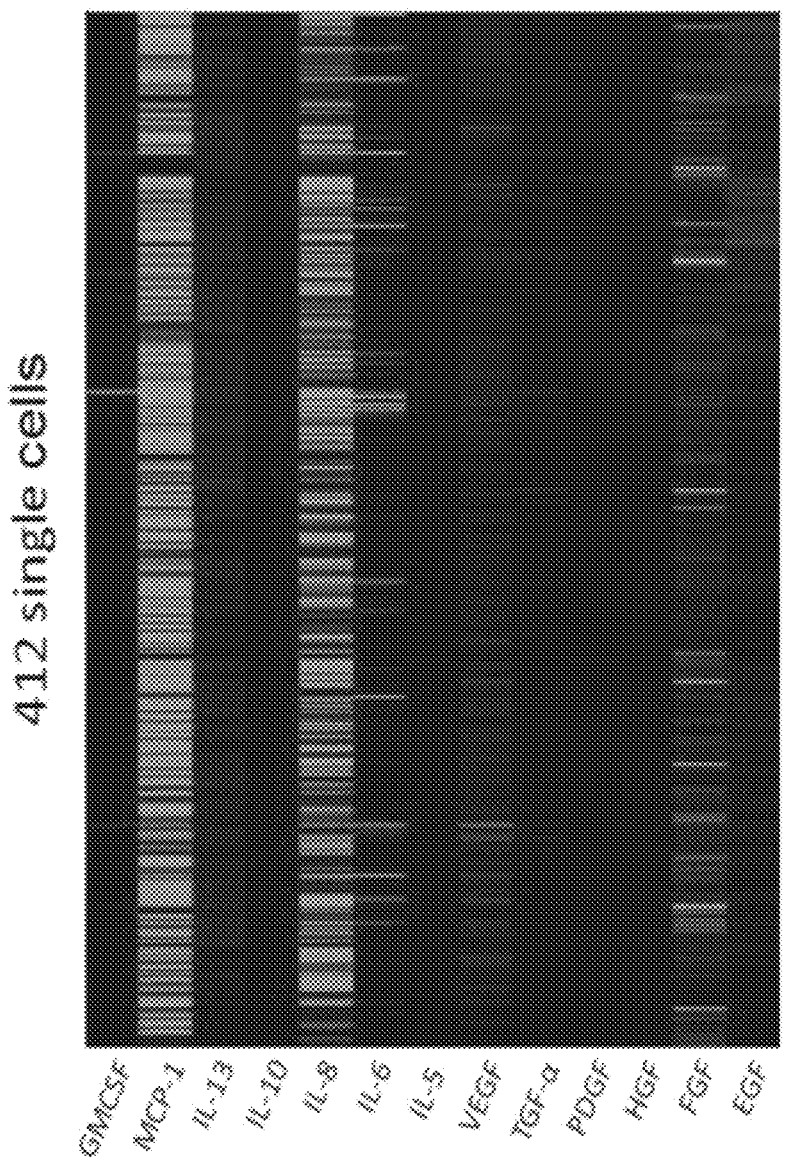
FIG. 14 is a heat map showing protein secretion profiles of single A549 cells at their basal level without stimulations.
Figure 15:
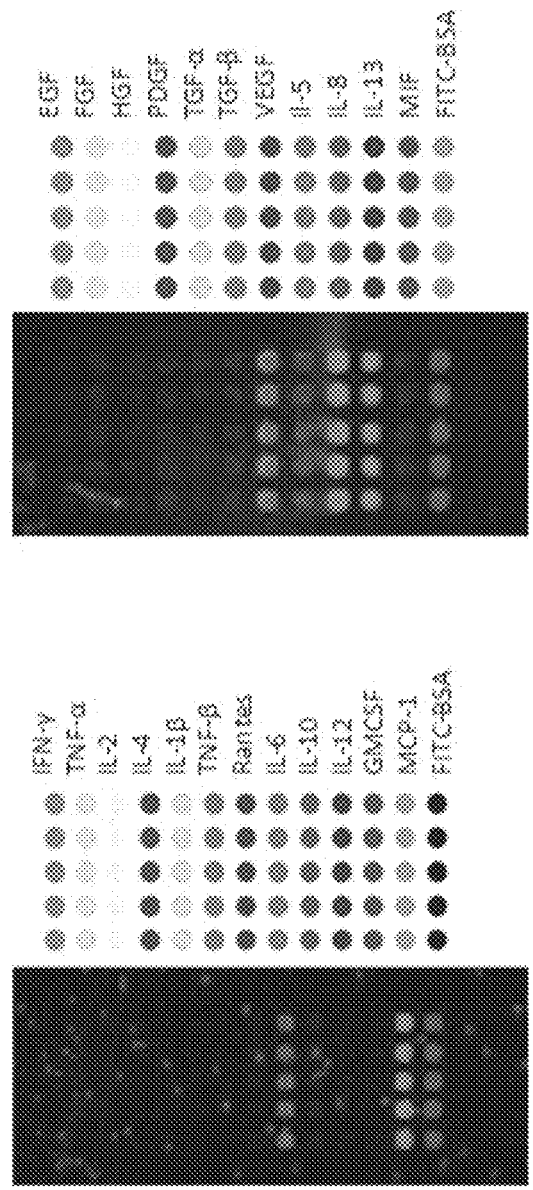
FIG. 15 is a set of images depicting the results of a control experiment measuring A549 population secretion. Proteins secreted from a large population of A549 cells were measured by a conventional antibody microarray (upper panels). Quantification results of all 23 proteins are shown in the lower panel.
Figure 15:
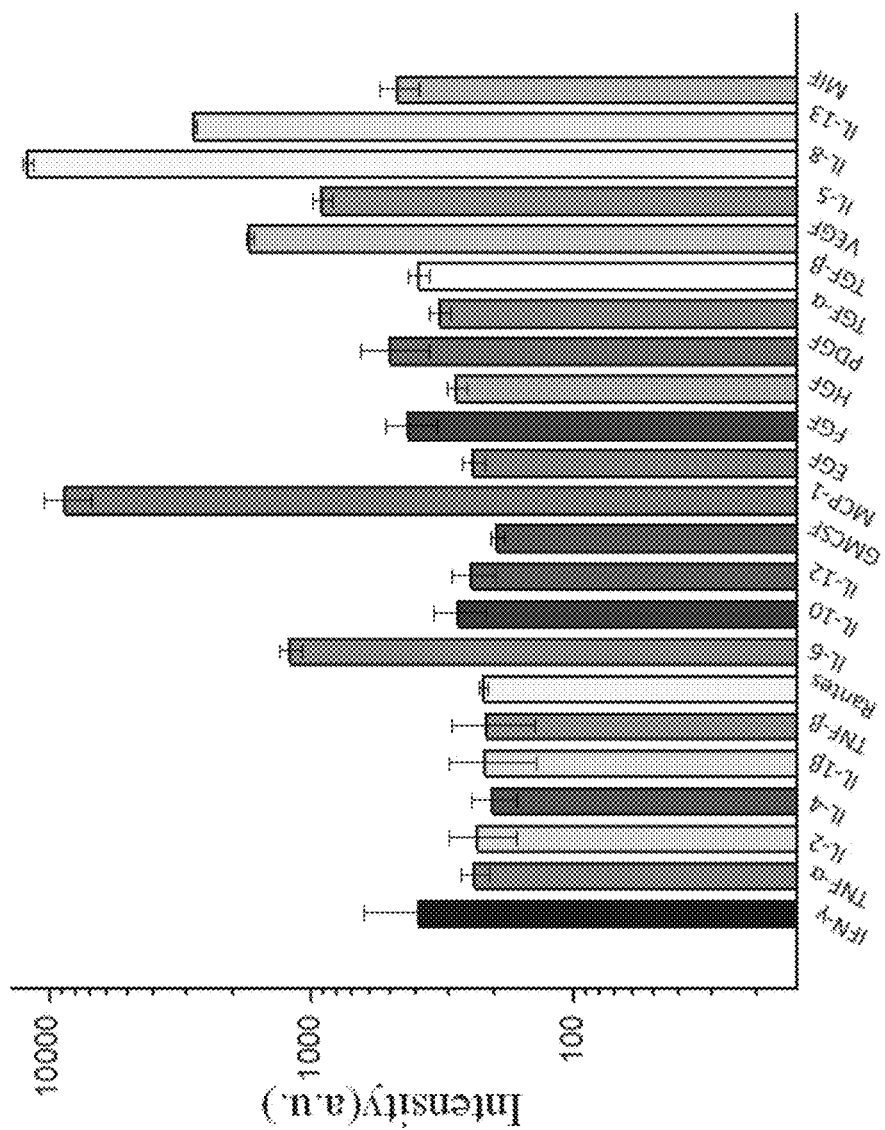

The single cell secretomic analysis chip was also used to measure two additional cell lines in order to assess the broad applicability of this platform. The first is an immune cell line (U937). The cells are human monocytes, which can be stimulated with phorbol myristate acetate (PMA) to differentiate into functional macrophage cells and then challenged by cytotoxin lipopolysaccharide (LPS) to stimulate cytokine production. This process emulates the inflammatory immune response of human macrophages to Gram-negative bacteria (Aderem and Ulevitch, 2000, Nature 406(6797):782-7). The major proteins observed are RANTES, TNF-α, MCP-1, IL-6, and IL-8 (FIG. 9B). While the majority of cells produce RANTES, IL-8, and TNF-α, the level of these proteins varies among individual cells and the secretion of other lower abundance proteins such as MCP-1 and IL-6 exhibit heterogeneous signatures. A bulk population secretion measurement was performed in parallel on the supernatant collected from the same cells to verify the single cell experiments (FIG. 13). The result also reveals RANTES, IL-8, MCP-1, IL-6, and TNF-α as the top five proteins, consistent with the single cell analysis. IL-8 and RANTES secretion increases with an increasing number of cells in a microchamber, and the amount of MCP-1 or TNF-α increases does not change significantly when cell number exceeds 4 (FIG. 9C). The second is a lung carcinoma cell line (A549) that constitutively produces cytokines or growth factors. Therefore, the basal level secretion from these cells was measured with no stimulation. The major proteins observed are MCP-1, IL-6, IL-8, VEGF, and FGF (FIG. 14) that were also validated by the bulk population assay using standard pin-spotted antibody microarray assays (FIG. 15). The proteins secreted from A549 cells include both pro-inflammatory cytokines and growth factors, in agreement with the role of lung tumor cells in both maintaining tumor growth and promoting an inflammatory microenvironment. Altogether, the cell line studies demonstrated that the platform is capable of rapid, quantitative, and high throughput analysis of protein secretion profiles in single cells compared to current conventional methods such as ELISpot. Validating the platform with cell lines allow the expansion of the sample repertoire to include more complex samples such as tissue specimens from patients.

Correlation Between Secretomic Signature and Migratory Property

Figure 16:
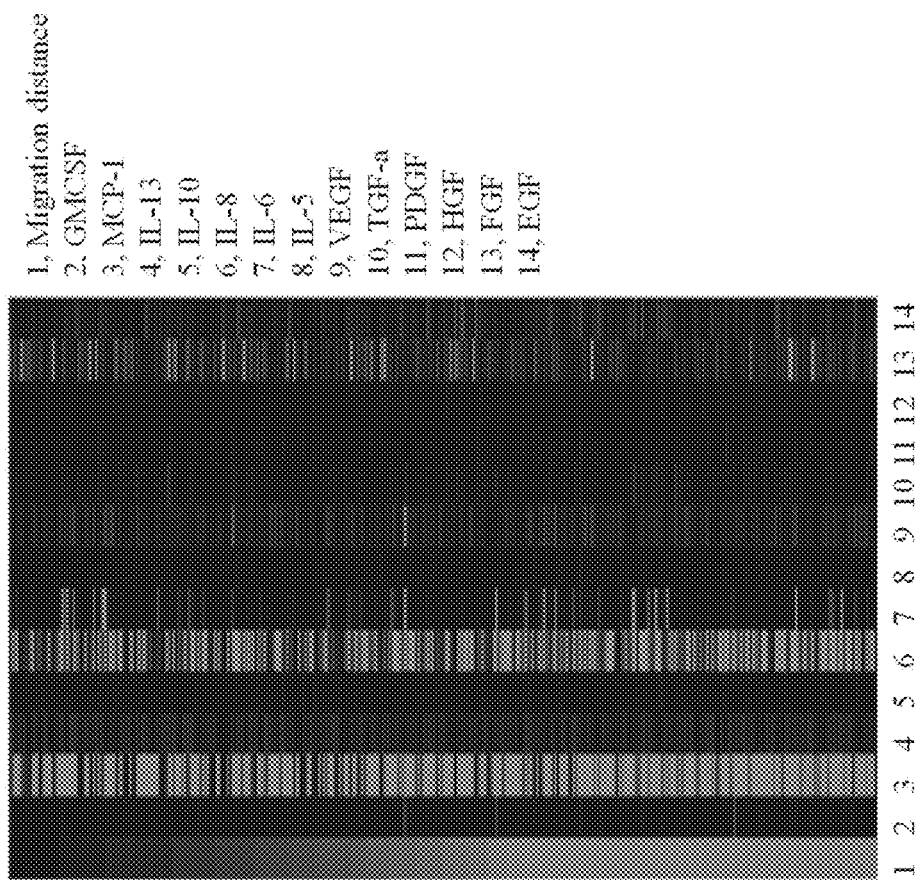
FIG. 16 is a heat map showing the correlation between A549 single cell migration distance and its corresponding protein secretion signals.

Although flow cytometry-based single cell analysis allows for multiplexed protein measure, the measured protein profile cannot be directly correlated to the cell's behavior and activity such as migratory property. The platform described herein utilizes live cell imaging to count captured cells, thus permitting simultaneous measurement of cellular behavior and subsequent correlation to the corresponding protein profile of the same cell. Herein the migration of lung cancer cells (A549) loaded in the single cell secretomic analysis chip was measured by measuring the distance of movement before incubation and after 24 h of incubation (FIG. 4A). These cells were seen to adhere to the channel wall and migrate at varying speeds. The results are summarized in a heatmap showing single-cell secretomic profiles sorted by increasing cell migration distance (FIG. 16). P-value analysis of cytokine levels was performed in high motility (top 20% over the observed range) vs low motility (bottom 20% of the same range) cells. While the majority of the cells do not migrate, the highly migratory cells are statistically associated with high expression of IL-8 ($P<0.01$) (FIG. 4B). The correlation between the secretion of MCP-1 and cell migration was less significant (FIG. 4c,d). IL-6 appears to be negatively associated with cell motility in the scatter plots but does not show statistical correlation using the aforementioned test. These proteins have been linked to the increase of motility and metastatic potential in different cancers (Singh et al., 1994, Cancer Res 54(12): 3242-7; Li et al., 2003, J Immunol 170(6):3369-76; Waugh and Wilson, 2008, Clin Cancer Res 14(21):6735-41), and through the investigation of single cell IL-8 secretion, it may be possible to study the secretomic signatures of individual cells linked to metastasis. In brief, the platform for the first time shows simultaneous measurement of protein secretomic signature and phenotypic properties (e.g., migration) of single live cells that can lead to improved understanding of cellular functions and the underlying molecular mechanisms.

Secretomic Profiling of Single Tumor Cells from Clinical Patient Specimens

Figures 5A, 5B:
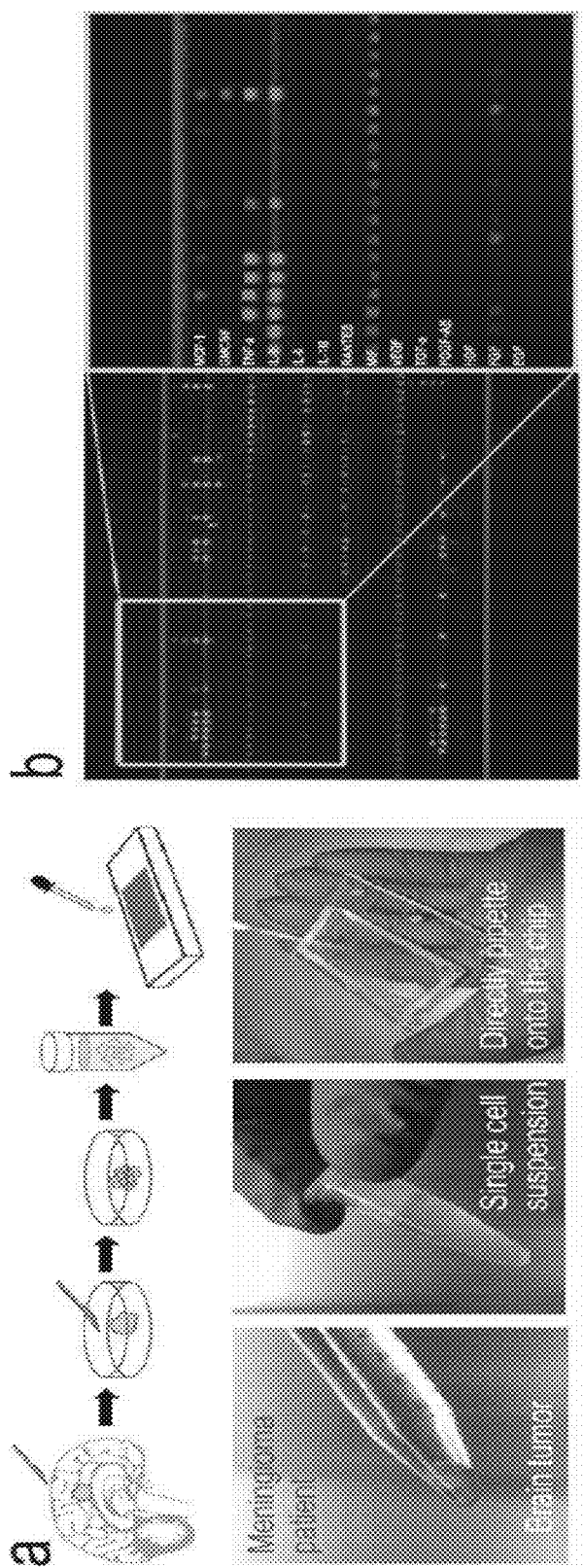
FIGS. 5A-5E show a set of images depicting the single-cell secretomic analysis of primary tumor cells from patients.
Figures 5C, 5D, 5E:
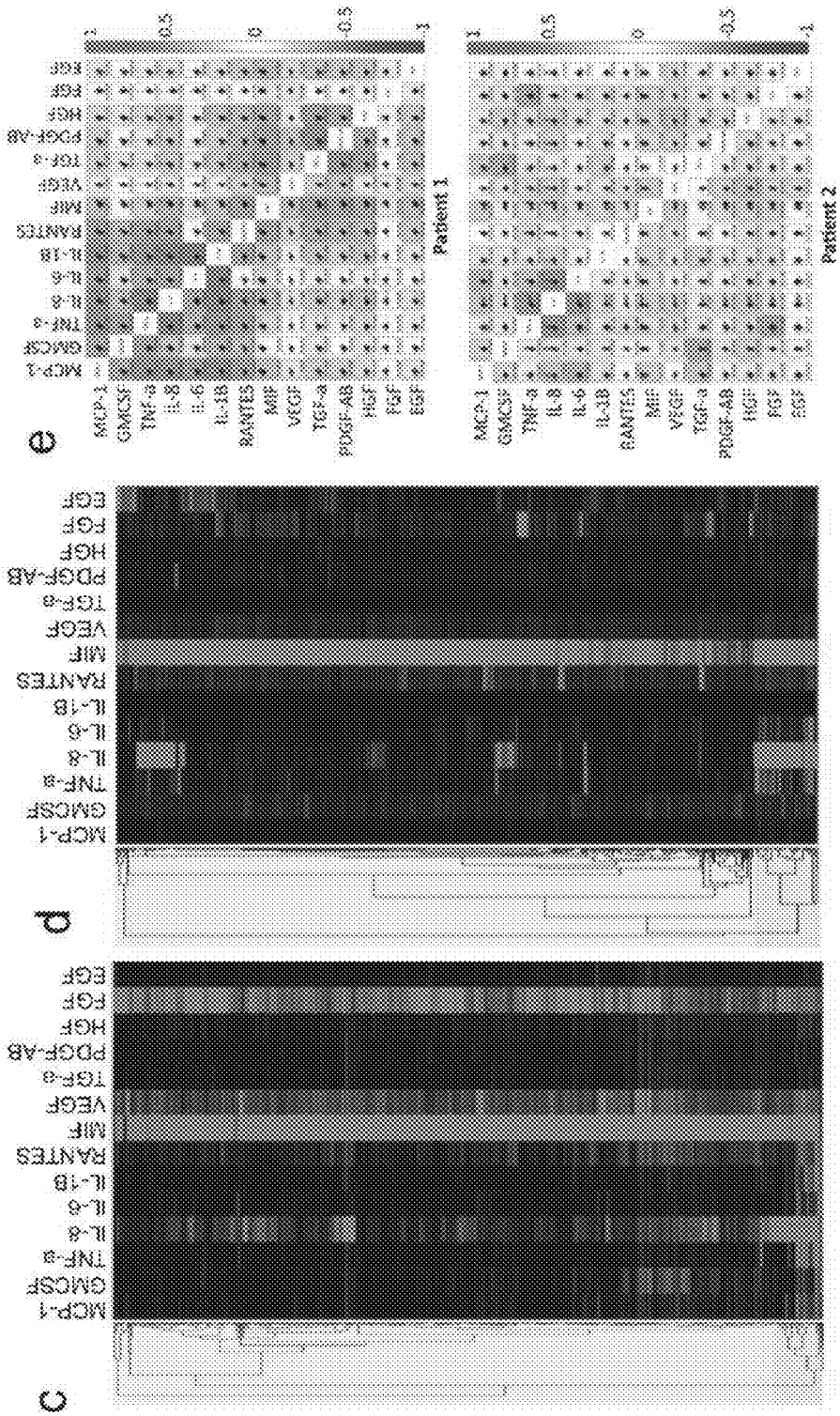
Figure 17:
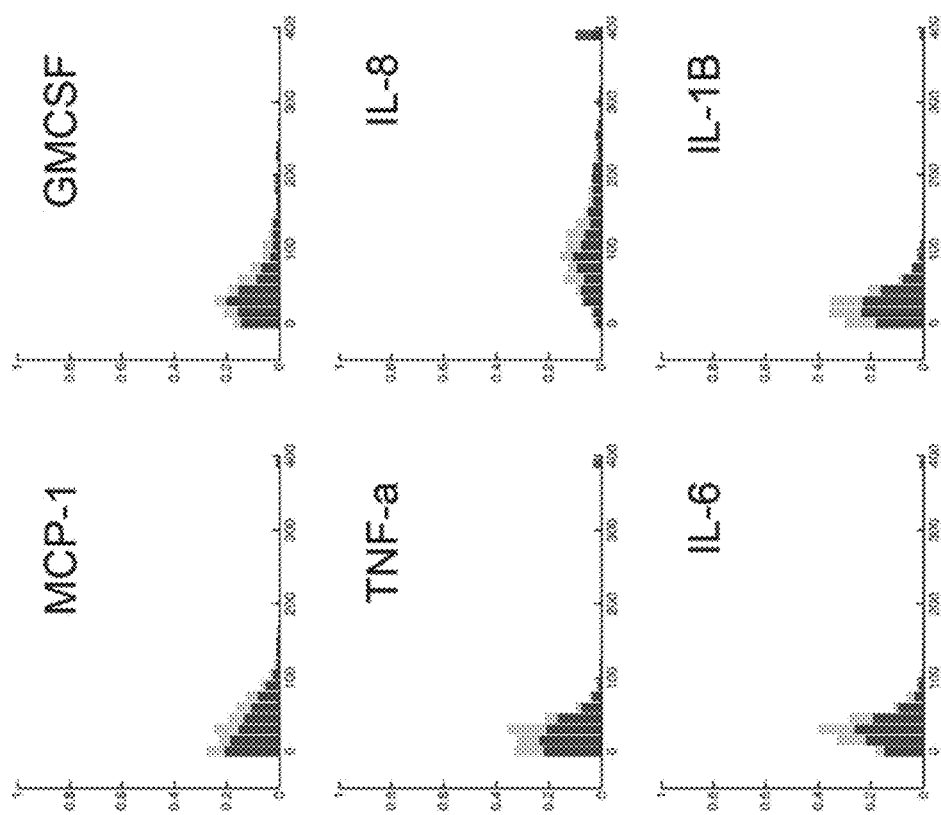
FIG. 17 is a set of histogram plots of individual proteins measured on the sample from Patient 1. (light gray=zero cells, dark gray=single cells)
Figure 17:
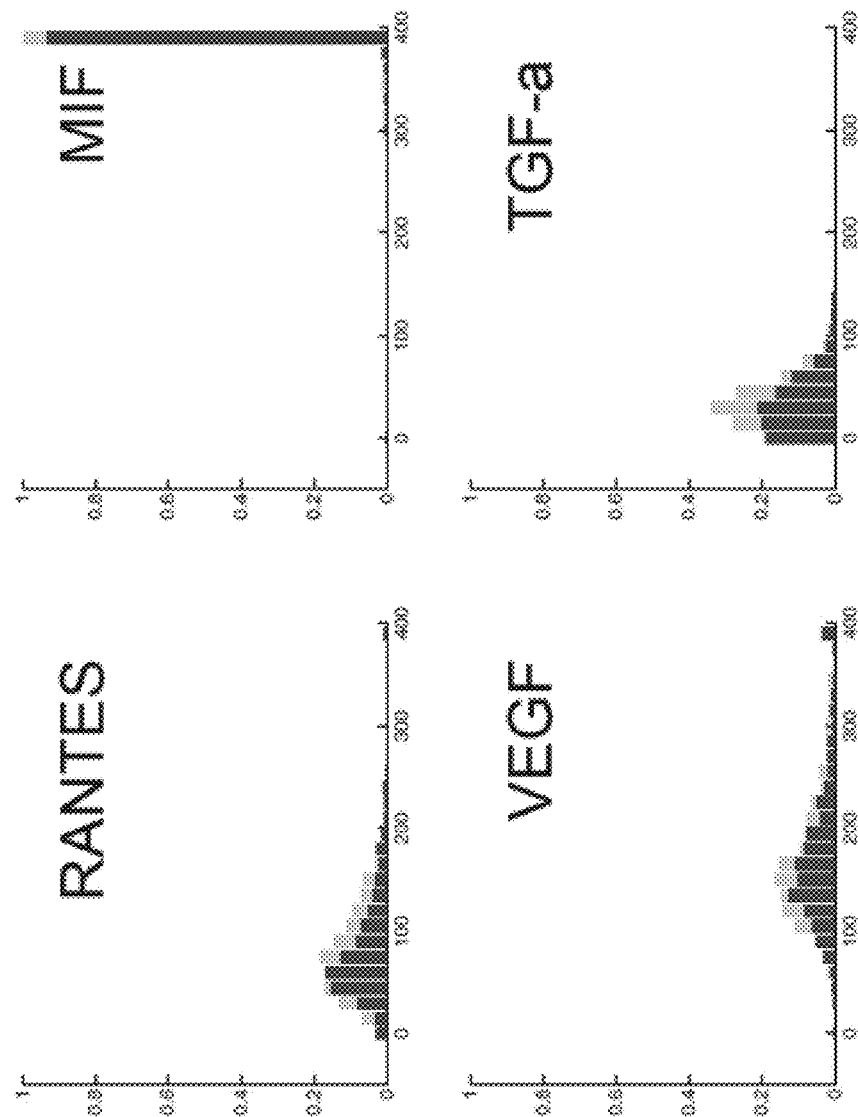
Figure 17:
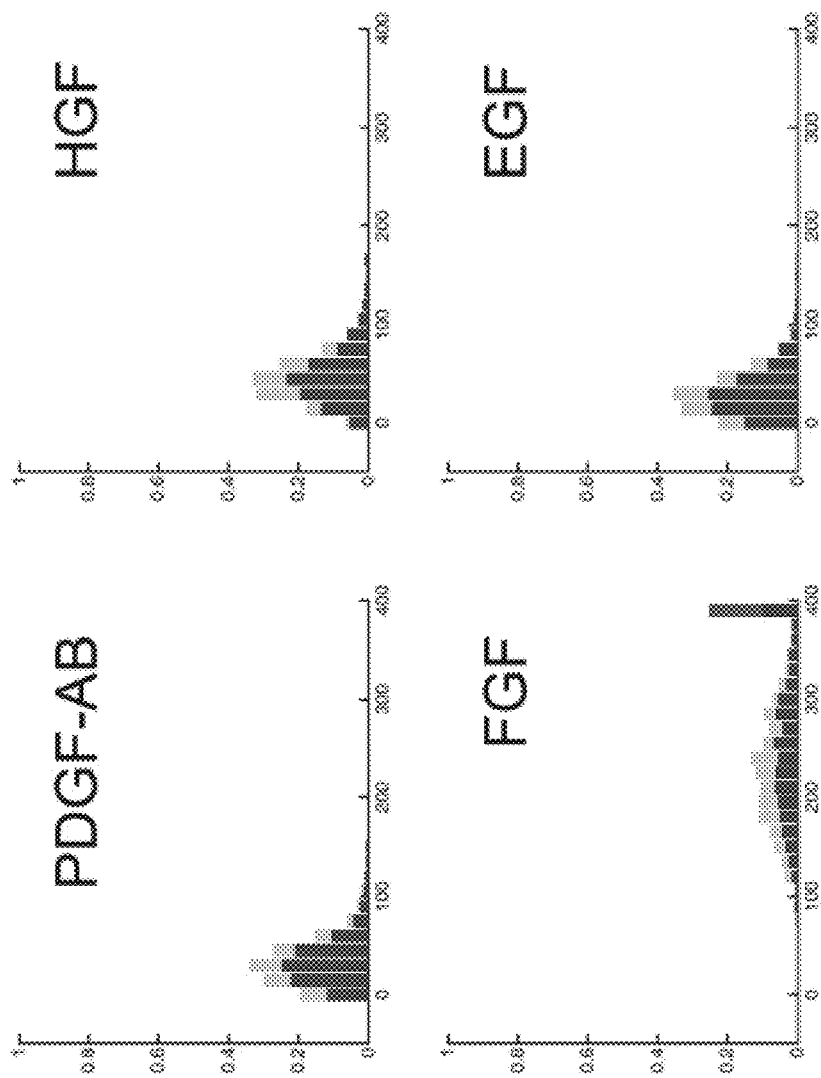
Figure 18:
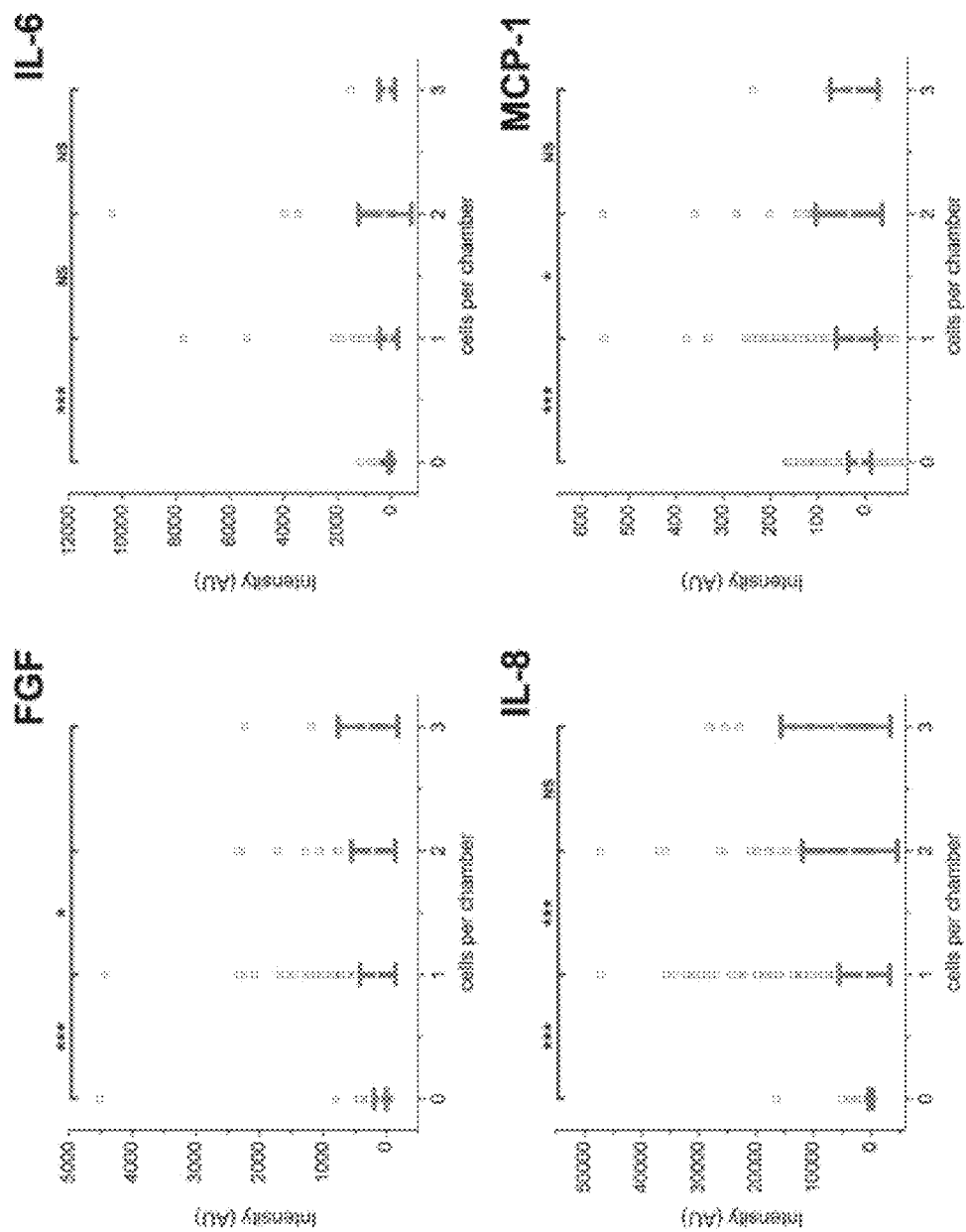
FIG. 18 is a set of scatter plots showing fluorescence intensity measured for eight selected proteins from Patient 2. (FGF, IL-6, IL-8, MCP-1, MIF, PDGF, RANTES, TNF-a)
Figure 18:
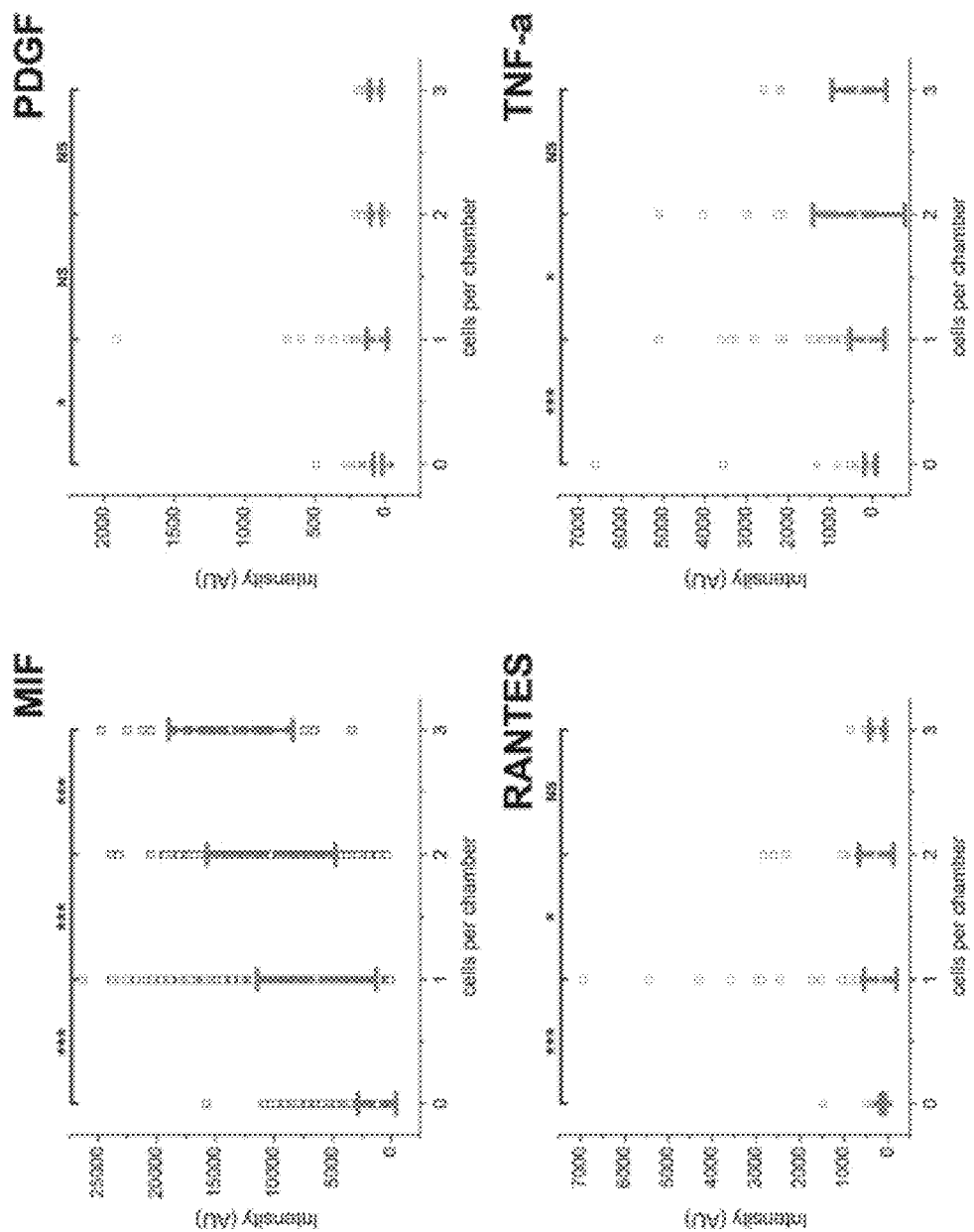

To expand the utility of the platform to measuring multiplexed secretion in cells derived from complex biospecimens, our device was also applied to the measurement of fresh primary tumor tissue from three patients (Table 2) with a malignant brain tumor, glioblastoma multiforme (patients 1 and 2), or meningioma (patient 3). A portion (<0.2 g) of the surgically resected tumor tissue is washed with ice cold phosphate-buffered saline, minced into smaller fractions and then dissociated into a single cell suspension using collagenase (FIG. 5A). The cells were spun down and resuspended in medium at a density of ~$10^6$ cells/mL. Within 1 h of tissue procurement, the single cell suspension is loaded onto the single-cell secretomic analysis device via pipette. After allowing the cells to secrete cytokines for 12 h, the pattern on the array is developed with detection antibodies and scanned. A raw fluorescent image (FIG. 5B, patient 1) shows excellent protein signals and similar background compared to the scanned image from cell lines. The antibody array includes 14 proteins as shown in FIG. 5b. In this experiment, between 0 and 22 cells were captured within a microchamber, with 1058 of the microchambers capturing single cells. The fluorescence intensities of each secreted cytokine from each individual channel was quantified and a heat map of the single cell secretion profiles was then generated (FIG. 5C). Unsupervised hierarchical clustering of the single cell secretion profiles resolved three separate populations of cells with varying activity. One cluster of cells (FIG. 5C, blue cluster) was generally more active, secreting a wider range of proteins presumably corresponding to a more aggressive phenotype, while the cells indicated by green exhibit the lowest level of cytokine production and may represent more quiescent phenotypes such as tumor stem/progenitor cells (Wicha et al., 2006, Cancer Res 66(4):1883-90). The large fraction indicated by orange are a variety of functional phenotypes. The result from the patient 2 (FIG. 5D) shows similarities to the results from patient 1, such as MIF and IL-8 as major proteins but a different pattern in that it has a much reduced production of inflammatory cytokines and a higher level of EGF. The second tier proteins all show distinct cellular heterogeneity. FIG. 17 and FIG. 18 present histograms and scatter plots of individual proteins, which show both the relative levels of proteins and the distributions among the cell population.

TABLE 2

Summary of the patient medical records

| Patient | Sample code | Gender | Age | Tumor type | Grade | Location |
|---|---|---|---|---|---|---|
| 1 | RFa 10-28-11 | Female | 64 | Glioblastoma | 4 | Left frontal |
| 2 | RFa 06-11-12 | Female | 66 | Glioblastoma | 4 | Right side not specified |
| 3 | RFa 04-02-12 | Female | 47 | Transitional Meningioma | 1 | Right side |

Figure 19:
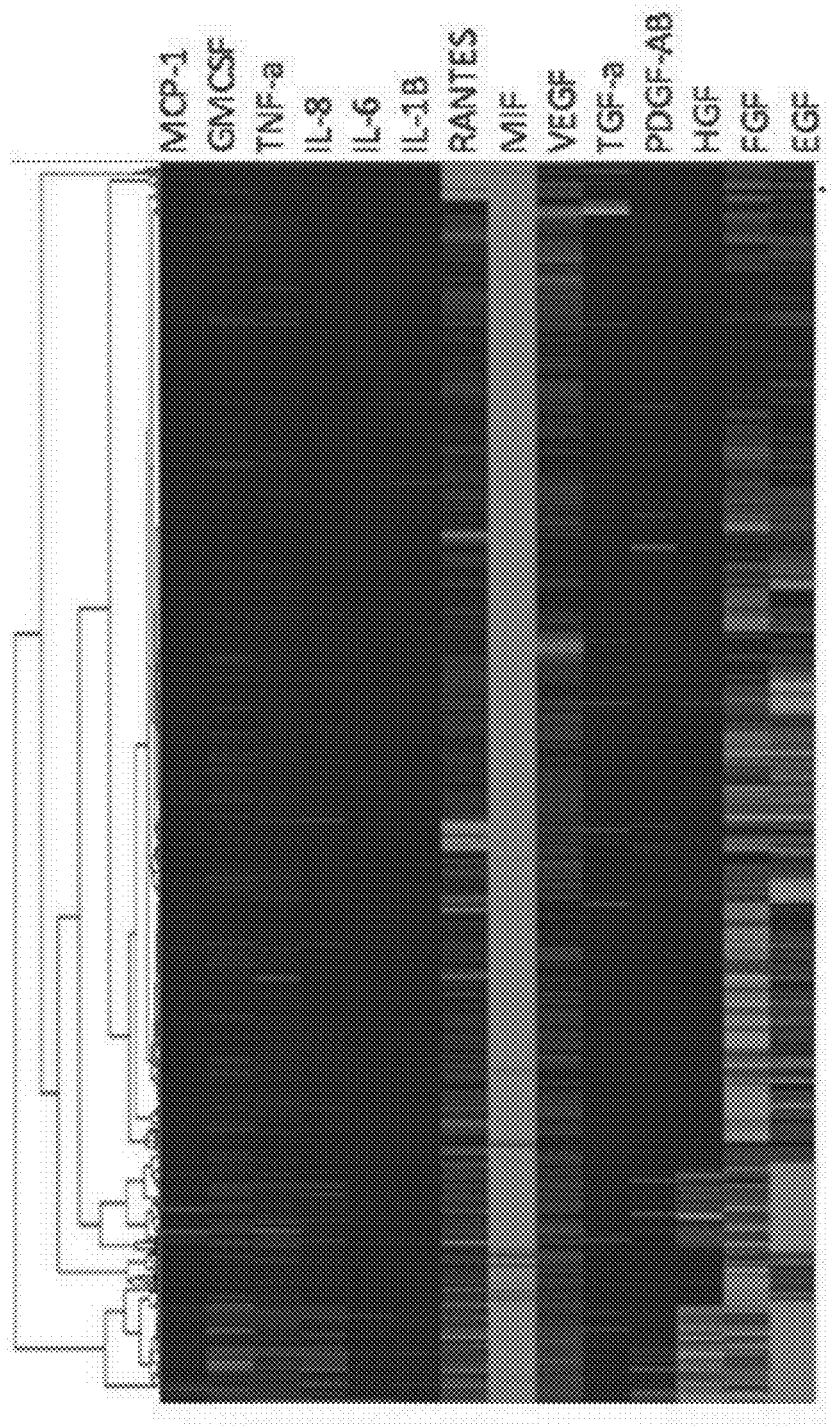
FIG. 19 is a heat map depicting single cell protein secretion profiling on the sample from Patient #3, a transitional meningioma patient.
Figure 20:
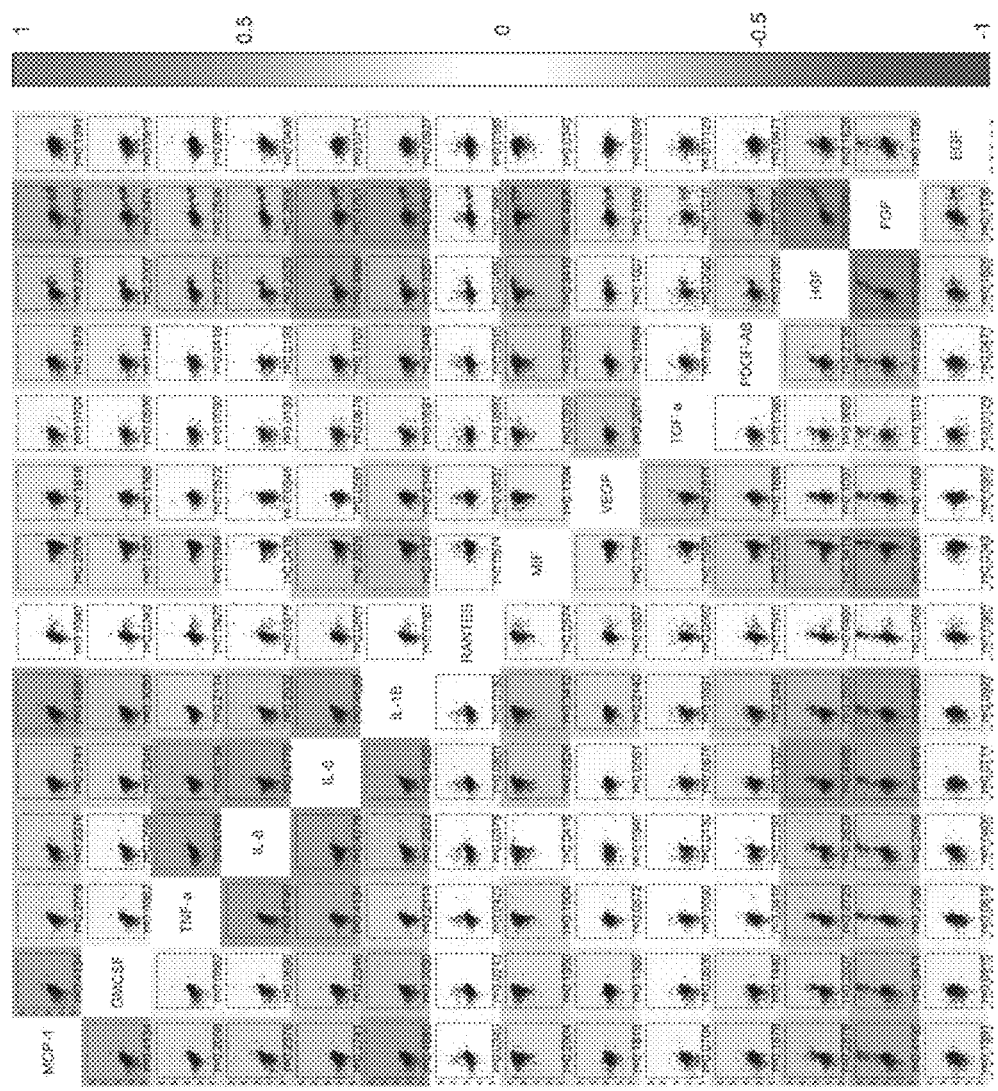
FIG. 20 is a set of scatter plots and protein correlation analysis of the single cell secretion data obtained from Patient 3.

Pseudo-three-dimensional scatter plots of the single cell cytokine measurements for the patient primary tumors in the format of flow cytometric plots were compiled and a 14×14 mosaic matrix was formed (FIG. 5E). The proteins are shown at the diagonal line, and each panel is a pairwise correlation plot, for each of which we performed a linear regression analysis to yield the R value. Then the whole matrix is color-coded by red (positive correlation) and blue (negative correlation), and the color intensity is proportional to R. In the patient 1 matrix, all the inflammatory cytokines are apparently associated within one cluster and several growth factors are grouped in a separate cluster, reflecting their functional difference. In the result for patient 2, the pro-inflammatory cytokines, although generally expressed at low levels, also show intercorrelation. Interesting, the secretion of EGF is negatively correlated to proinflammatory and chemoattractant proteins (MCP-1, GMCSF, and IL-8). A third sample from a patient (patient 3) with transitional meningioma was also analyzed, which is considered a more homogeneous and less inflammatory tumor. Indeed the results for patient 3 (FIG. 19 and FIG. 20) show reduced pro-inflammatory cytokine signals. These studies imply the relevance of the results to these cells' physiological functions or pathological condition. Currently surgical treatment remains the most effective therapy of human glioblastoma. Afterward, chemotherapy might be carried out systemically or by putting drug-containing wafers into the surgical cavity to further eradicate invasive tumor cells that have diffused to normal brain tissue (Lesniak and Brem, 2004 Nat Rev Drug Discovery 3(6):499-508). The platform potentially can distinguish and quantitate invasive cell phenotypes as they generally produce more cytokines as well as different profile of cytokines, which has the clinical value to determine tumor invasiveness and tailor the chemotherapeutic strategy for individual patients. In addition, these proteins that act as the soluble signals to mediate cell-cell communication in tumor microenvironment may be identified as new therapeutic targets for personalized treatment (Dvorak 2002, J Clin Oncol 20(21):4368-80; Rich and Bigner, 2004, Nat Rev Drug Discovery 3(5):430-46; Reardon and Wen, 2006, Oncologist 11(2):152-64).

Single Cell Proteomics

Single cell proteomic analysis has generally been much more challenging than genetic analysis from single cells, due to the lack of equivalent amplification methods for proteins such as polymerase chain reaction (PCR) for nucleic acids. Recent advance in flow cytometric analysis allows for 34-plexed measurement of protein markers from single cells, but most proteins are either surface receptors or cytoplasmic proteins (Bendall et al., 2011, Science 332 (6030):687-96). Intracellular cytokine staining (ICS) enables indirect assessment of "secreted" proteins, but currently the number of cytokines that can be measured is practically limited to below 10, presumably due to increased nonspecific binding from a large number of antibodies in the limited volume of a single cell. Further, increasing the number of compounds detected using ICS is correlated with decreased accuracy and increased noise due to spectral overlap between individual labels. Moreover, unlike protein secretion, it is not a direct measurement of cell function. Thus, multiplexed protein secretion measurement is a missing piece of functional characterization of single cells. It has become increasingly evident that even genetically homogeneous cells can be extremely heterogeneous, leading to many unanswered questions in studying their biology (Bendall et al., 2011, Science 332(6030):687-96). Studying the secretion profile of single cells can reveal much more about tumor heterogeneity than studying the signaling patterns of cells in a population wherein the signals become averaged out and all defining information is lost, emphasizing the need for studying single cell secretion (Bendall and Nolan, 2012, Nat Biotechnol 30(7):639-47; Michor and Polyak, 2010, Cancer Prev Res 3(11):1361-4).

Described herein is a sub-nanoliter multiplexed immunoassay chip that enables high throughput, simultaneous detection of a panel of 14 cytokines secreted from over a thousand single cells in parallel. This platform provides significant advantages specific to the detection of secreted proteins and offers information complementary to that obtained through flow cytometry. An example scenario where this device would offer unique advantages is that when a cell separation tool is used to sort out a phenotypically identical cell population using specific surface markers, these cells can then be placed in the present device to further reveal cellular heterogeneity at the functional level. For instance, human T cell lineages often display a number of functions, and the complex combinations of multiple functions in a single T cells dictates the "quality" of this cell in response to a specific antigen. Recent studies showed that multifunctional T cells often exhibit greater potency and durability (Seder et al., 2008, Nat Rev Immunol 8(4):247-58). The latest HIV vaccine trials employed the ELISpot technique to count interferon-γ (IFN-γ)-secreting T cells as a means to assess the efficacy of vaccination, but it turns out that most IFN-γ-secreting cells are terminally differentiated effector T cells and have minimal protective effect against viral infection. This platform represents a promising tool to perform polyfunctional analysis on the cells isolated from a flow cytometer or other separation techniques, e.g., magnetically assisted cell sorting (Adams et al., 2008, Proc Natl Acad Sci USA 105(47):18165-70), to bring single-cell protein assay to another level of functional analysis. A potential concern of the platform is that cells are isolated in the sealed microchamber and may experience a condition that affects the normal functioning of primary cells ex vivo. As a bioanalytical tool, the microchip was not intended to perform long-term culture of cells and the typical assay time is a few hours to 1 day. It has been reported that ex vivo assay of primary cells in a sealed and isolated environment do produce proteins over a long time as anticipated for their intrinsic physiological activity (Ma et al., 2011, Nat Med 17(6):738-43); Han et al., 2012, Proc Natl Acad Sci USA 109(5):1607-12) and interestingly the cells could gain greater viability in a sealed nanoliter-chamber because it recapitulates the in vivo crowdedness in primary tissue and retains sufficient concentrations of cytokines for more effective autocrine signaling. Thus, the microchip is a promising platform for high-throughput analysis of protein secretion profiles from single primary cells and may assist in differential diagnosis and monitoring of cellular functions in patients.

Example 2: Spatial and Spectral Encoded 45-Plex Assay

Described herein is the development of one embodiment of the device of the invention which uses the spatial position and color of detectable labels to assay for the presence of up to 45 different compounds of interest. The use of differently labeled secondary antibodies allows for the ability to vastly increase the number of compounds of interest that can be simultaneously detected.

Figure 27:
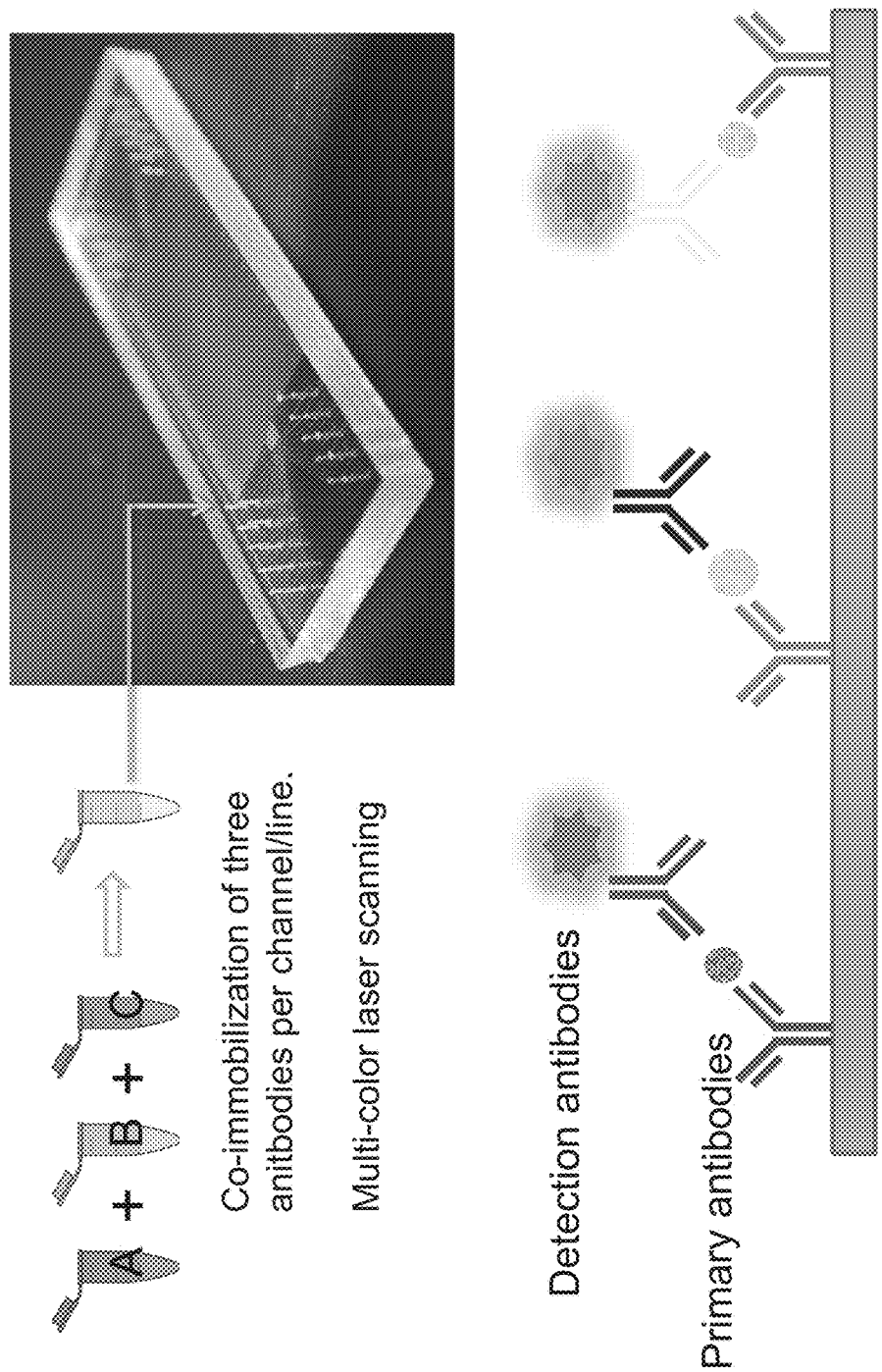
FIG. 27 is a diagram depicting the use of three different primary antibodies, and three different detection antibodies, each labeled with a different fluorescent label, to provide a spatial and spectral (i.e. fluorescent colorimetric) encoding of capture of single cell compounds single-cell assay of the invention.

FIG. 27 is a diagram depicting how the assay functions. Each spatial line (or other isolated feature) has three different primary antibodies, each specific for the detection of three different compounds of interest. The detection antibodies (secondary antibodies) used to provide a detectable label at the site of compound binding, are each labeled with a differently colored fluorescent label. Analysis of the assay thus comprises using a multi-color laser scanning method to observe the spatial location of each detectable label throughout the device.

Figure 28:
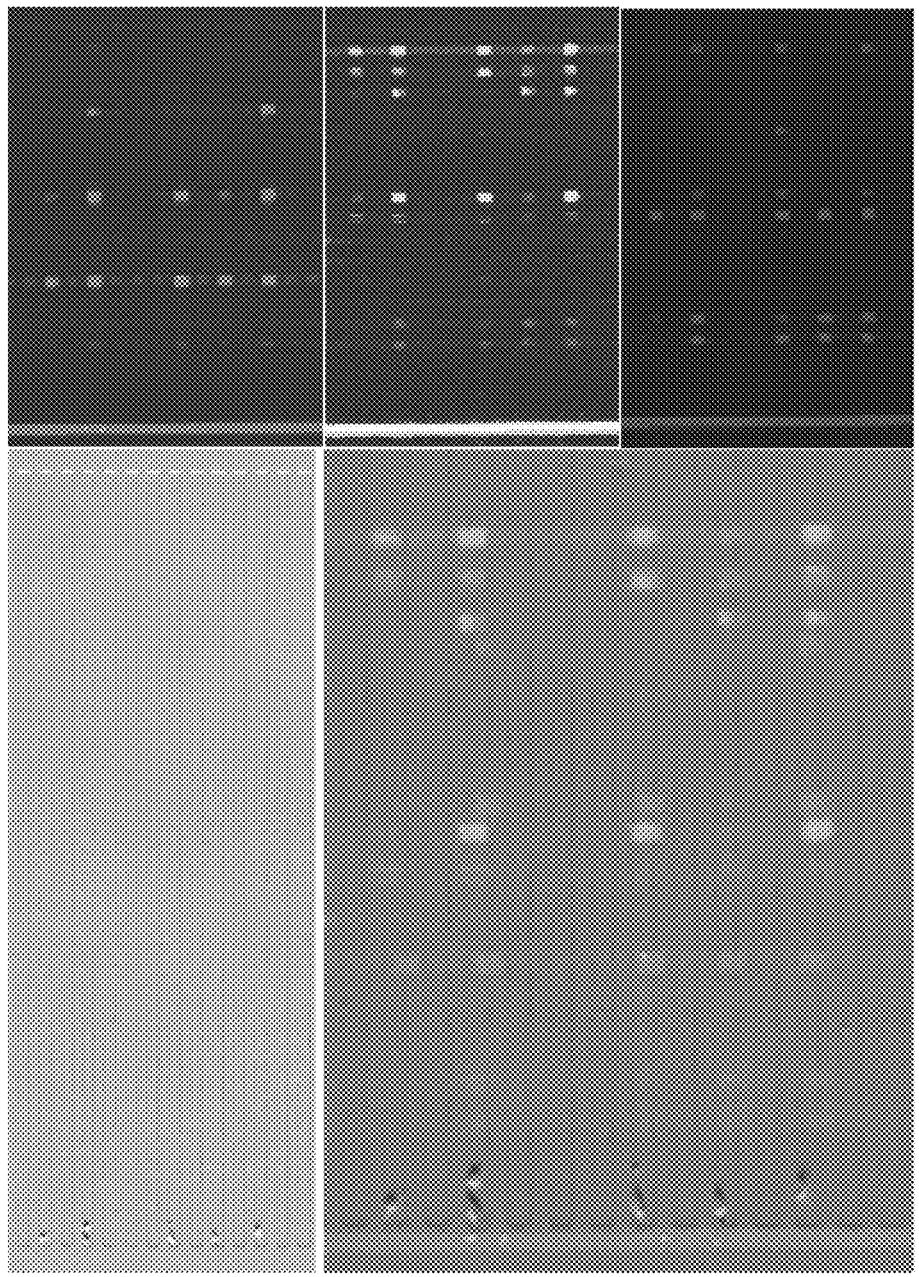
FIG. 28 is a set of images depicting the imaging of three different detectable labels on the same view of the antibody array, demonstrating the spectral encoding of the array and the ability for the multiplexed detection of a large number of compounds.
Figure 29:
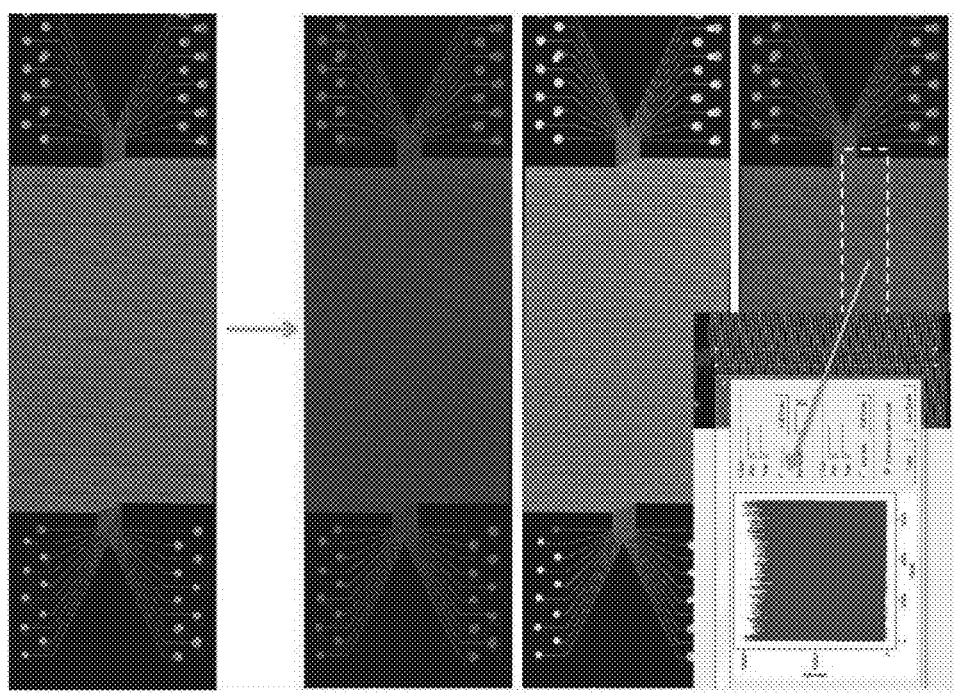
FIG. 29 is a set of images depicting the uniformity in imaging of the device using a multitude of different detectable labels. Scanned fluorescence images (mixed and separate) showing the result of multiple antibody co-immobilization on poly-1-lysine glass slide. The inset figure shows high uniformity of protein coating across the entire capture agent slide (C.V.<5% in 1 in.×2 in area). Fluorescently labeled bovine serum albumin (488-BSA, 532-BSA, 647-BSA respectively) were used in this test.

FIGS. 28 and 29 demonstrate the ability to detect 3 different colors from the device. FIG. 28 shows an overlay of the microwells with the antibody array. On the right, the same field of view is imaged for the three different wavelengths. The detection at a specific location of a specific wavelength thus determines the presence of a particular compound of interest. FIG. 29 demonstrates that a number of different wavelengths can be used and shows the uniformity of wavelength detection. Further, as shown in FIG. 29, the device provides uniform protein coding across the slide.

An exemplary panel is shown in FIG. 30, which demonstrates that 14 different lines are used, each with 3 differently colored labels to detect 42 compounds of interest. Also included is a fifteenth line used as a control. The antibodies used in this assay are given below in Table 3.

TABLE 3

Antibodies used in 45-plex spatial and spectral assay

| Protein | Capture antibody Isotope/clone/vendor/catalog | Detection antibody Isotope/clone/vendor/catalog |
| --- | --- | --- |
| IL-1a | Mouse IgG2A/4414/RD/MAB200 | Mouse IgG1, κ/364-3B3-14/Biolegend/500104 |
| IL-1b | Mouse IgG1/JK1B-1/Biolegend/508202 | Mouse IgG2b, κ/JK1B-2/Biolegend/508304 |
| IL-3 | Mouse IgG1/653A10B1/Invitrogen/AHC0832 | Rat IgG1, κ/BVD8-3G11/Biolegend/500502 |
| IL-4 | Mouse IgG1, κ/8D4-8/Biolegend/500702 | Rat IgG1, κ/MP4-25D2/Biolegend/500802 |
| IL-5 | Rat IgG2a, κ/JES1-39D10/Biolegend/500902 | Rat IgG2a, κ/JES1-5A10/Biolegend/501006 |
| IL-6 | Rat IgG2a, κ/MQ2-39C3/Biolegend/501204 | Rat IgG1, κ/MQ2-13A5/Biolegend/501102 |
| IL-7 | Rat IgG2a, κ/BVD10-11C10/Biolegend/506604 | Rat IgG1, κ/BVD10-40F6/Biolegend/501302 |
| IL-8 | Mouse IgG1, κ/H8A5/Biolegend/511502 | Mouse IgG1, κ/E8N1/Biolegend/511402 |
| IL-10 | Rat IgG2a, κ/JES3-12G8/Biolegend/501504 | Rat IgG1, κ/JES3-9D7/Biolegend/501402 |
| IL-12(p70) | Mouse IgG1/24945/RD/MAB611 | Rat IgG1, κ/7B12/Biolegend/511002 |
| IL-13 | Mouse IgG1/32116/RD/MAB213 | Rat IgG1, κ/JES10-5A2/Biolegend/501902 |
| IL-15 | Mouse IgG/RD duoset capture antibody/DY247 | Mouse IgG1/AM00959PU-N/Acris/AM00959PU-N |
| IL-1RA | Mouse IgG1/JK1RA-1/Biolegend/509902 | Mouse IgG/RD duoset Capture antibody/DY280 |
| MIF | Mouse IgG1 Kappa/2A10-4D3/Abnova/H00004282-M01 | Mouse IgG1 Kappa/2A10-4D3/Abnova/H00004282-M01 |
| IL-17A | Mouse IgG2a, κ/BL127/Biolegend/512603 | Mouse IgG1, κ/BL23/Biolegend/512702 |
| MCP-1 | Mouse IgG1, κ/5D3-F7/Biolegend/502607 | Armenian Hamster IgG/2H5/Biolegend/505902 |
| Rantes | Mouse IgG2b kappa/VL1/Invitrogen/AHC1052 | Mouse IgG1/21418/RD/MAB678 |
| TNF-a | Mouse IgG1, κ/Mab11/Biolegend/502902 | Mouse IgG1, κ/MAb1/Biolegend/502802 |
| TNF-b | Mouse IgG2A/5807/RD/MAB621 | Mouse IgG1, κ/359-238-8/Biolegend/503002 |
| IL-22 | Rat IgG2a, kappaIL22JOP/Ebioscience/16-7222-85 | Mouse IgG1/142928/RD/MAB7821 |
| MIP-1b | Mouse IgG1 kappa/A174E 18A7/Invitrogen/AHC6114 | Mouse IgG2B/24006/RD/MAB271 |
| SCF | Mouse IgG1/J231/Peprotech/500-M44 | Mouse IgG1/13302/RD/MAB655 |
| M-CSF | Mouse IgG2b/AM09180PU-N/Acris/AM09180PU-N | Mouse IgG2A/21113/RD/MAB616 |
| EGF | Mouse IgG1/AM09146PU-N/Acris/AM09146PU-N | Mouse IgG1/10827/RD/MAB636 |
| HGF | Mouse IgG1/SBF5 C1.7/Novus/NB100-2696 | Mouse IgG1/24516/RD/MAB694 |
| NGF-b | Mouse IgG1, κ/JKhNGF-1/biolegend/509602 | Mouse IgG1, κ/JKmNGF-1/Biolegend/509702 |
| PDGF | Rabbit IgG/polyclonal/Acris/PP1061P2 | Mouse IgG1, κ/108128/RD/MAB1739 |
| VEGF | Mouse IgG1/A183C/Invitrogen/AHG0114 | Mouse IgG2B/26503/RD/MAB293 |
| IL-2 | Mouse IgG2A/5355/RD/MAB602 | Goat IgG/RD duoset detection antibody/DY202 |
| MIP-1a | Mouse IgG1/14D7 1G7/Invitrogen/AHC6034 | Goat IgG/RD duoset detection antibody/DY270 |
| TGF-a | Goat IgG/RD duoset capture antibody/DY239 | Goat IgG/RD duoset detection antibody/DY239 |
| TGF-b | BD 559119 | BD 559119 |
| G-CSF | Mouse IgG1/3316/RD/MAB214 | Goat IgG/polyclonal/RD/BAF214 |
| IFN-g | Mouse IgG1, κ/MD-1/Biolegend/507502 | Mouse IgG1, kappa/4S.B3/ebioscience/13-7319-85 |
| GMCSF | Rat IgG2a, κ/BVD2-23B6/Biolegend/502202 | Rat IgG2a, κ/BVD2-21C11/Biolegend/502304 |
| IL-9 | Ebioscience Ready sets go | Ebioscience Ready sets go |
| IL-23 | Ebioscience Ready sets go | Ebioscience Ready sets go |

TABLE 3-continued

Antibodies used in 45-plex spatial and spectral assay

| Protein | Capture antibody Isotope/clone/vendor/catalog | Detection antibody Isotope/clone/vendor/catalog |
|---|---|---|
| MMP-2 | Mouse IgG/RD duoset capture antibody/DY902 | Mouse IgG/RD duoset detection antibody/DY902 |
| MMP-9 | Mouse IgG1/36020/RD/MAB936 | Goat IgG/polyclonal/RD/BAF911 |
| IL-27 | Ebioscience Ready sets go | Ebioscience Ready sets go |
| IL-29 | Ebioscience Ready sets go | Ebioscience Ready sets go |
| TSLP | Ebioscience Ready sets go | Ebioscience Ready sets go |
| BSA-488 conjugated | 488 conjugated BSA | |
| BSA-532 conjugated | 532 conjugated BSA | |
| BSA-635 conjugated | 635 conjugated BSA | |

Figure 31:
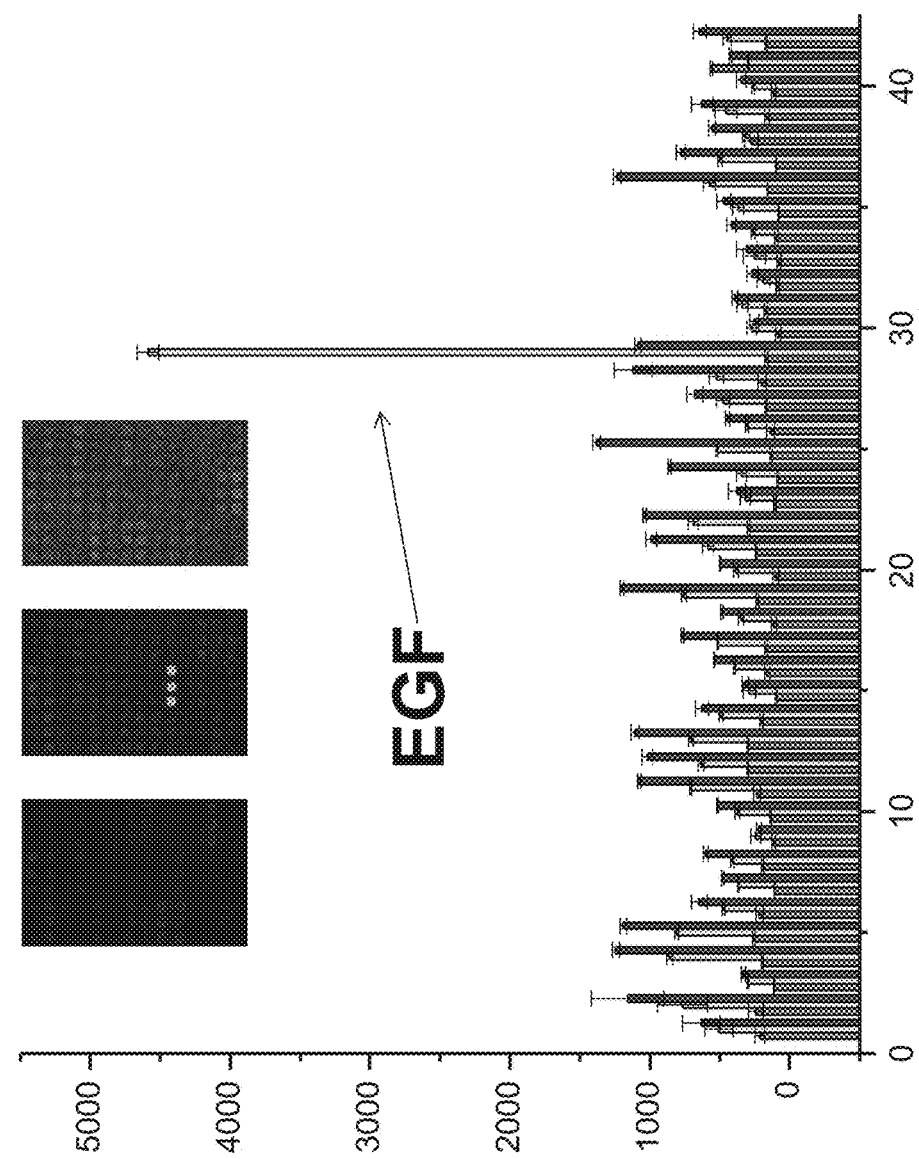
FIG. 31 depicts the results of an experiment demonstrating the specificity of the assay via the shown non-crossreactivity of the capture agents, where a sample containing only EGF results in the presence of fluorescence in only the location/wavelength combination corresponding to EGF.

Experiments were run to ensure that the antibodies on the same spatial line are all below threshold in cross-reactivity. In these experiments, the antibody array was subjected to a solution containing only EGF. As shown in FIG. 31, using the spatial and spectral detection scheme described, EGF is the only species detected. It was observed that the location and color corresponding to EGF lights up significantly above the 1000 intensity threshold that is used as background. This ensures that any observed responses are only caused by the particular cytokine binding event of interest. This data proves that, based on spectral data, that the triple spatial encoding in the spectral assay is viable and will not produce significant error in terms of quantification of the secretomic cytokines.

Figure 32A:
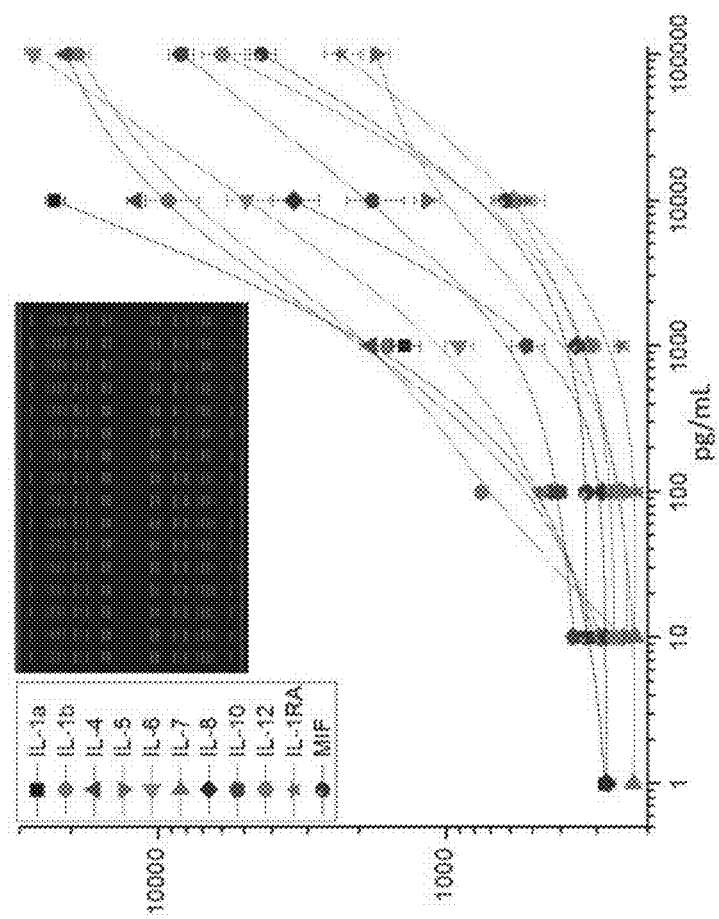
FIGS. 32A-32C show a set of calibration curves obtained with recombinant proteins for groups for the compounds in the 488 group (FIG. 32A), the 532 group (FIG. 32B) and the 635 group (FIG. 32C). These curves can be used to quantify the concentration of each cytokine in a sample, based on a detected intensity.
Figure 32B:
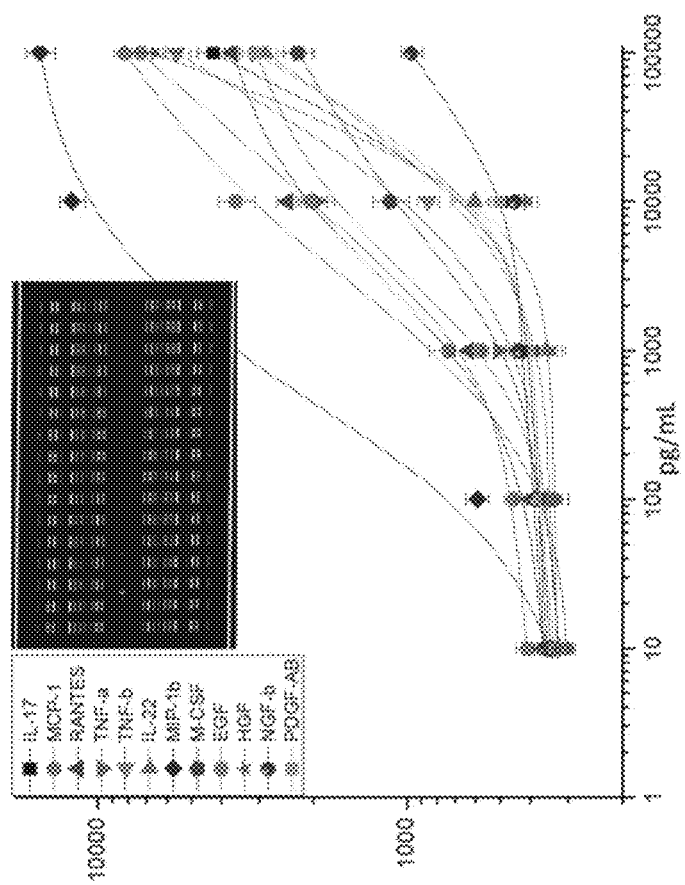
Figure 32C:
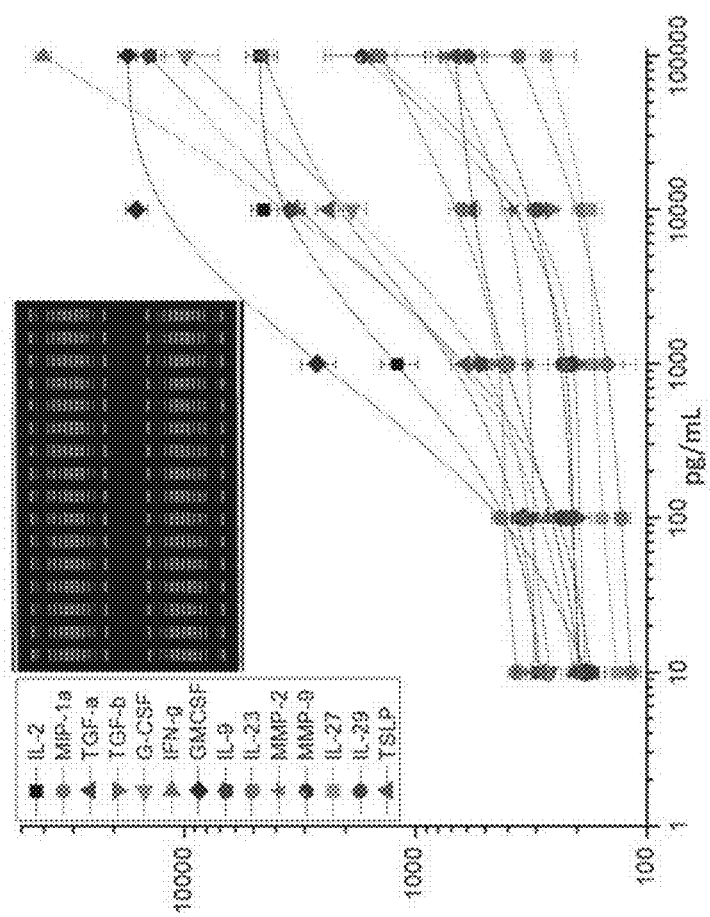

For calibration, titration curves (FIG. 32A-C) were determined for each of the compounds of interest, in order to properly quantitatively correlate a detected intensity signal to the concentration of the compound of interest in the sample.

Figure 33:
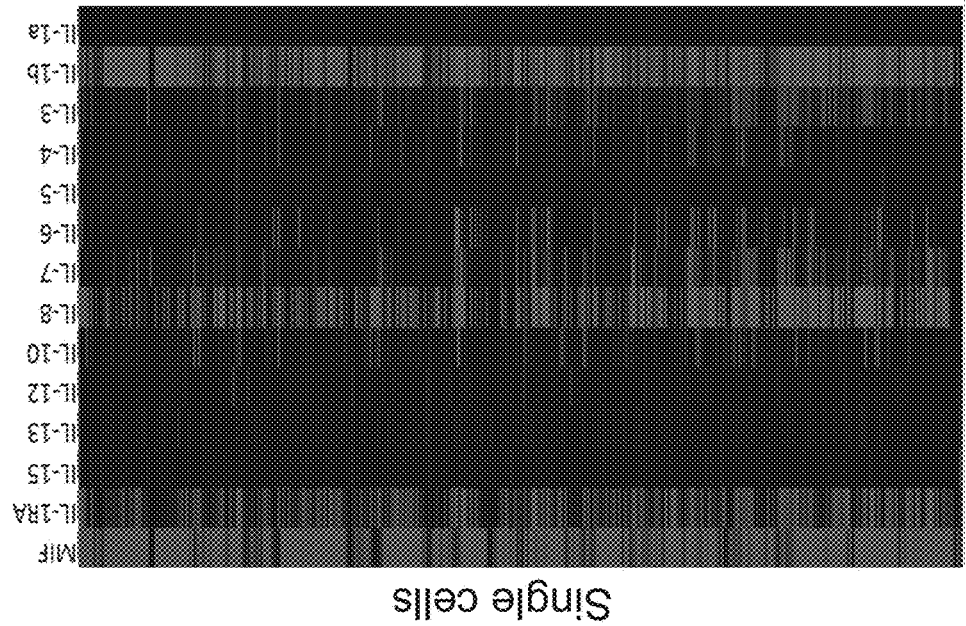
FIG. 33 depicts the raw data from the 488 nm imaged wavelength using the spectral assay of the invention.
Figure 33:
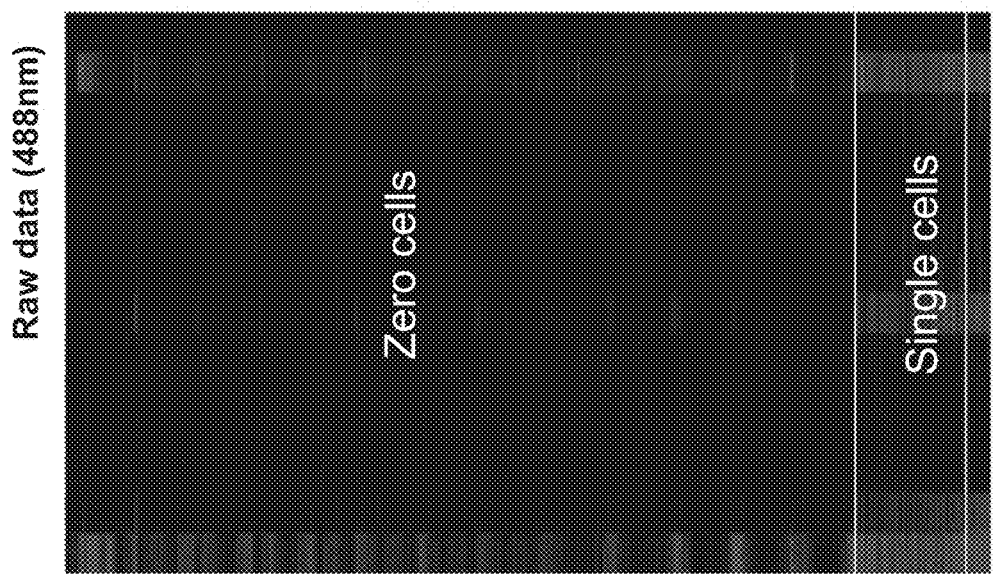
Figure 34:
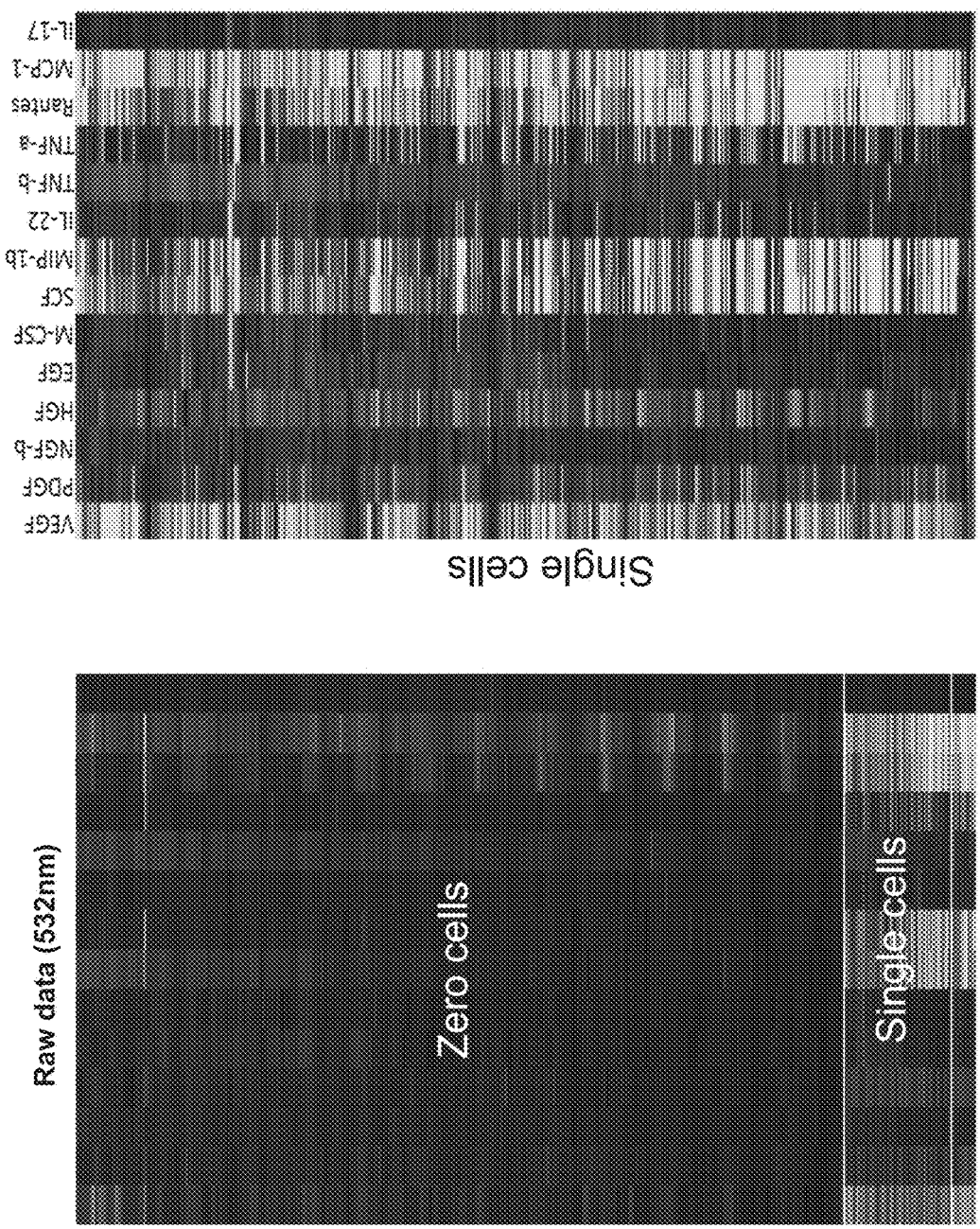
FIG. 34 depicts the raw data from the 532 nm imaged wavelength using the spectral assay of the invention.
Figure 35:
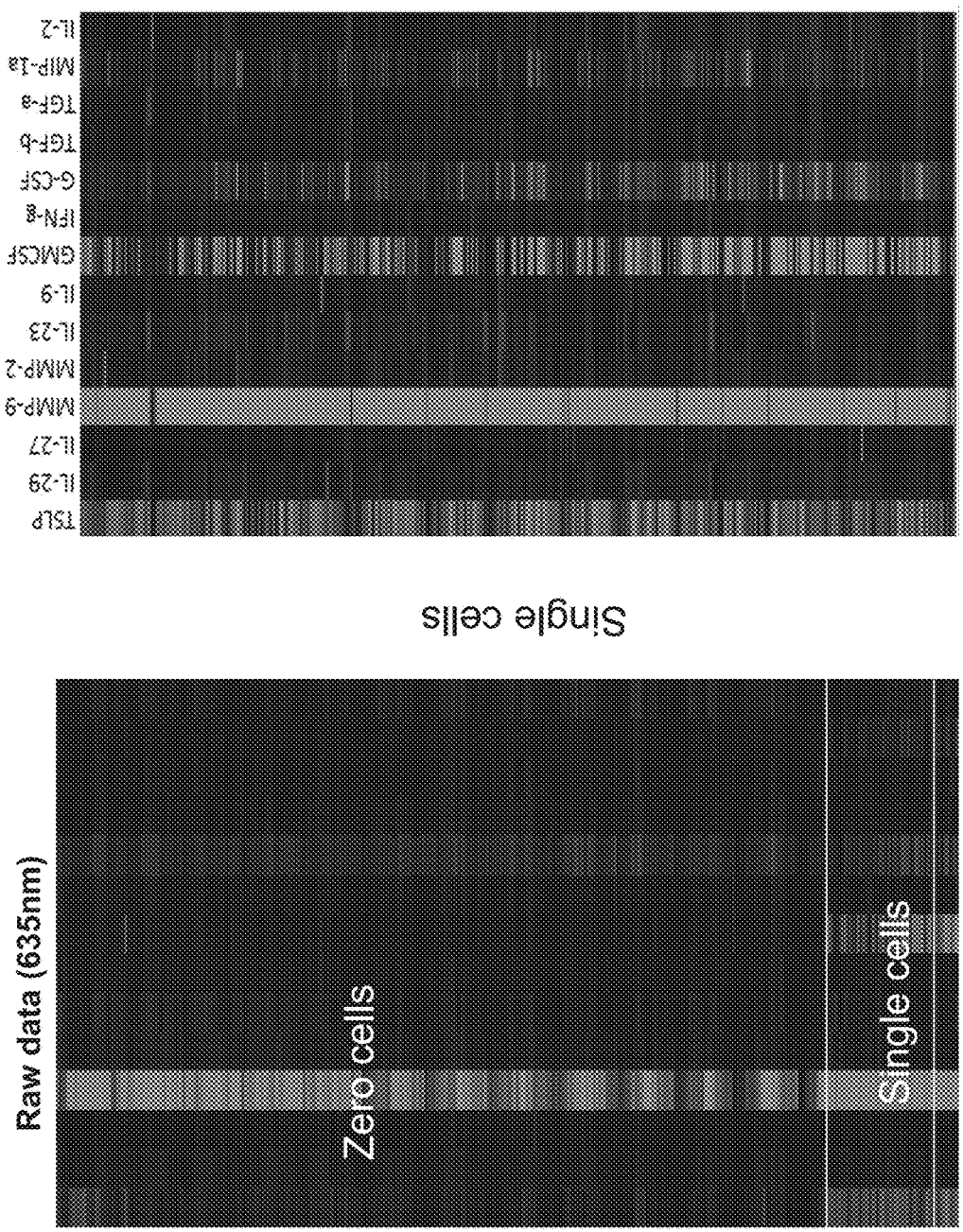
FIG. 35 depicts the raw data from the 635 nm imaged wavelength using the spectral assay of the invention.
Figure 36:
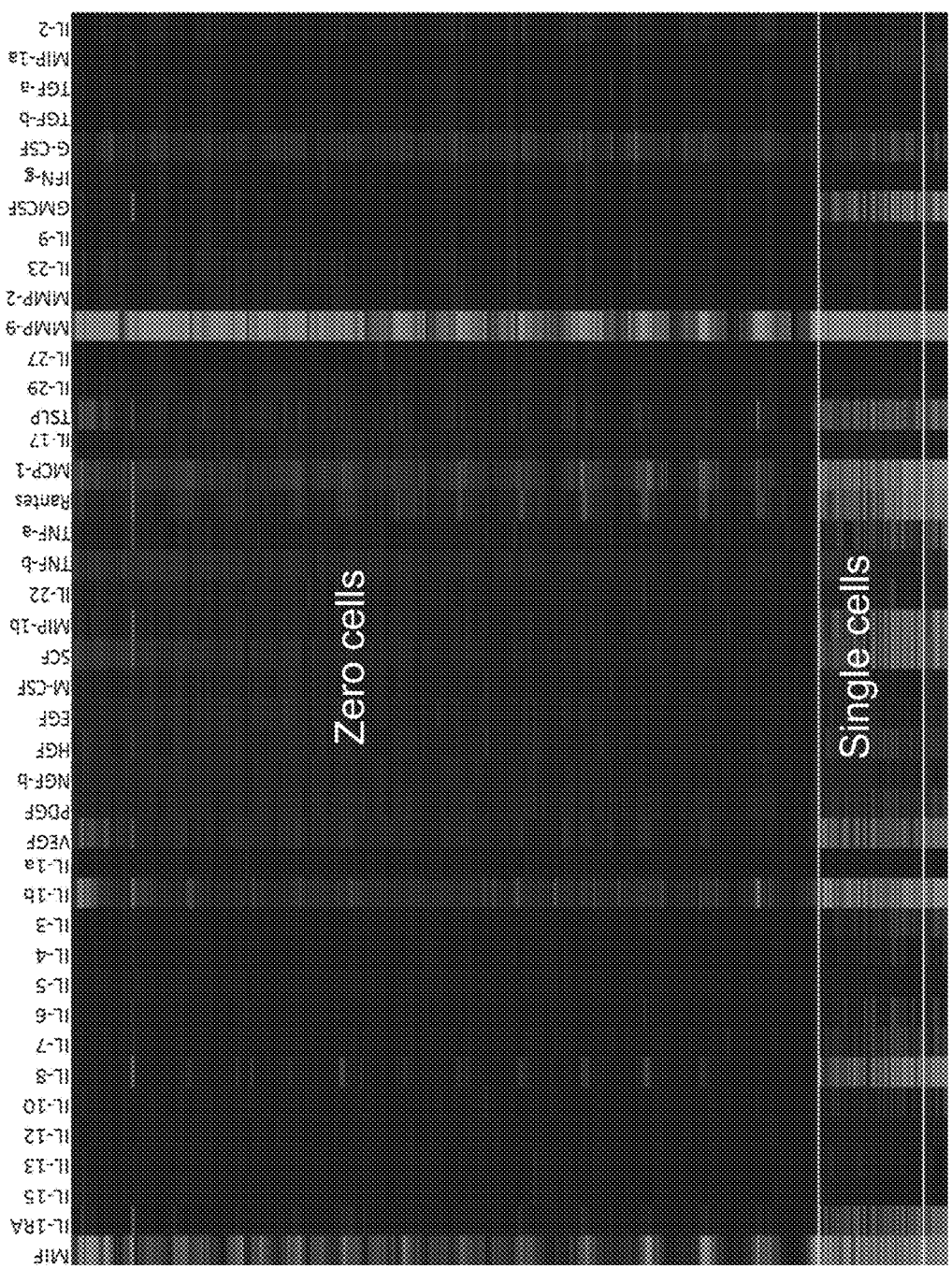
FIG. 36 depicts the combined raw data from the 488 nm, 532 nm, and 635 nm imaged wavelengths using the spectral assay of the invention.
Figure 37:
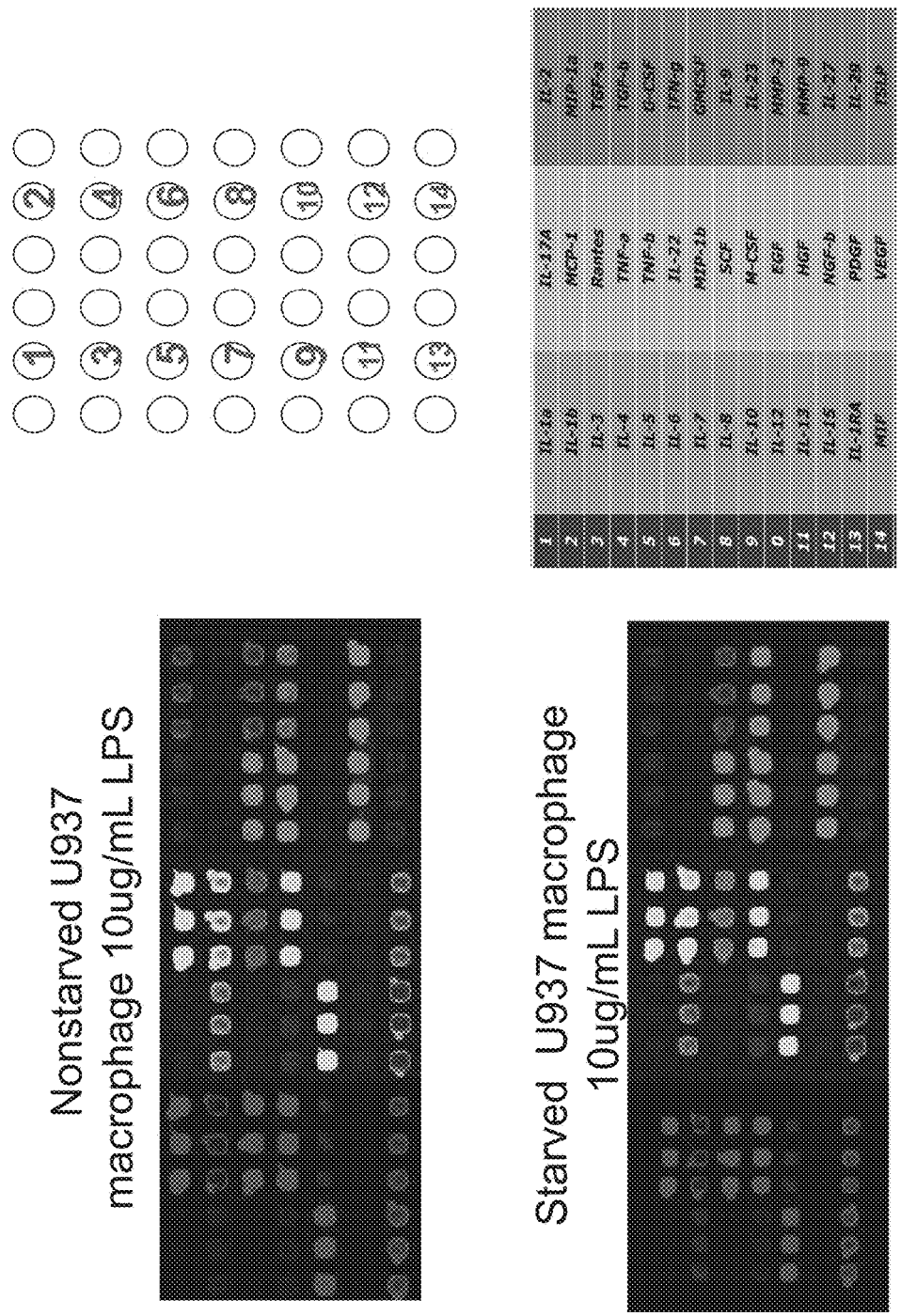
FIG. 37 depicts raw data of cytokine detection using the population based micro-ELISA.

Experiments were conducted using human macrophage cells derived from U937 cell lines through the differentiation by 50 ng/mL PMA for 48 hours. Experiments compared cells that were starved with FBS free medium to cells that were fed with 10% FBS. Starved and non-starved cells were either left non-stimulated or alternatively, were stimulated with 10 μg/mL LPS, a common pathogenic molecule in gram-negative bacteria. Responses detected by the spatial/spectral assay described herein were compared to micro-ELISA. Detection of compound binding was conducted as described elsewhere herein, but was repeated for the 3 wavelengths used. FIG. 33 depicts the raw data for the 488 nm wavelength, FIG. 34 depicts the raw data for the 532 nm wavelength, and FIG. 35 depicts the raw data for the 635 nm wavelength. For ease of analysis, the detection of the 3 wavelengths were "extended" as shown in FIG. 36, which shows the detection of all the species of interest (i.e. combined species detected in the 488 nm, 532 nm and 635 nm raw data). As shown, the data was artificially pseudo-colored to a single color (in this case red), for ease of subsequent analysis. The single cell analysis using the spatial/spectral assay was compared to population-based micro-ELISA assay, the data of which is shown in FIG. 37.

Figure 38:
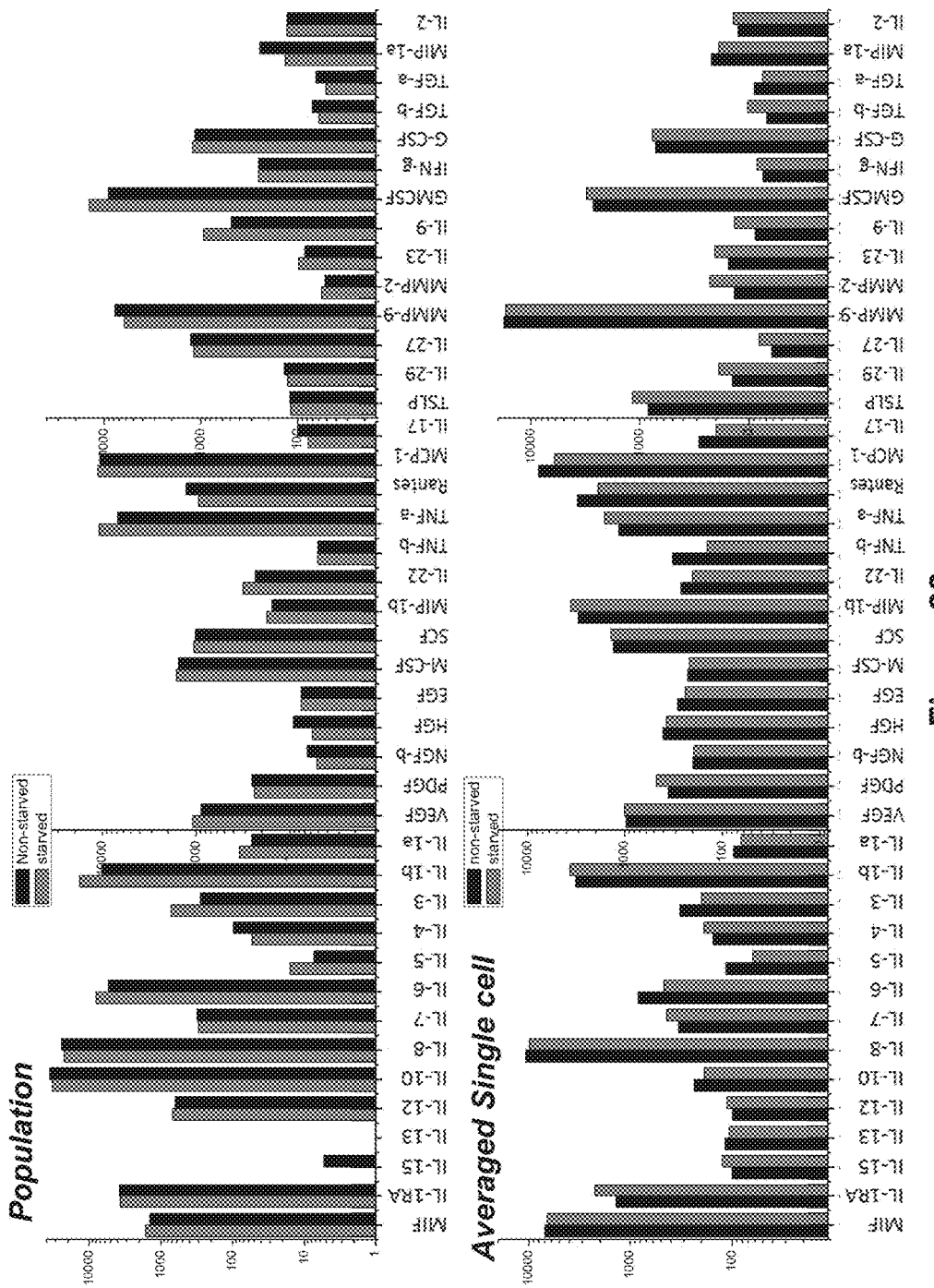
FIG. 38 is a graph depicting the comparison of population-based micro-ELISA and the single-cell assay of the invention.

Comparing the average single-cell data from the spatial/spectral assay to the population-based micro-ELISA data revealed important differences in these analyses (FIG. 38). In certain instances, there was a greater than 10× difference in the predicted 'phenotype' or 'secretome'. For example, IL12 and IL10 are predicted to be much higher (~10×) in their secretions when looking at the whole population data compared to the averaged single cell data. This indicates that micro-ELISA does not accurately evaluate the single-cell response. These large differences may be due to sub-populations with distinct polyfunctionality that cannot be shown on the population level, or population based sensing differences (i.e. cell to cell communication), or different cytokine secretion patterns based on time stamp of analysis.

The difference between starved and non-starved is validated against the micro-ELISA technique within high agreement for most cytokines. In particular IL-8, MIP-1b, MCP-1, IL-1RA, GMCSF, GCSF, MIP-1a, IL-1b, IFN-g: correlate well (statistically significant); MIF, MMP-9, TSLP, Rantes: Show significant population decrease in averaged single cell; IL-6, IL-10, TNF-a: doesn't correlate well due to perhaps differences in evaluation discussed above.

Figure 39:
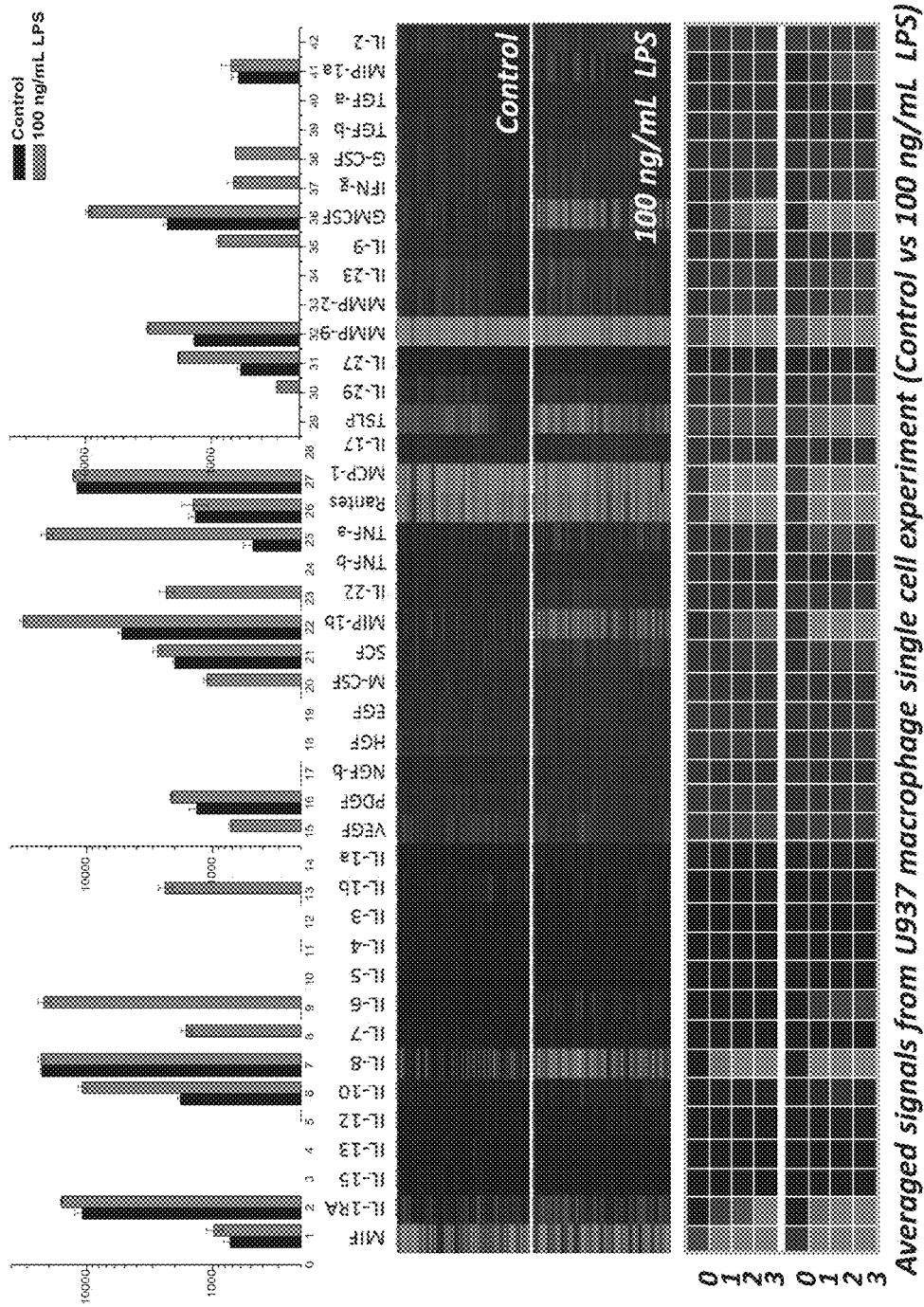
FIG. 39 depicts the results of the experiments of using the 45-plexed single cell assay comparing single-cell secretions of non-stimulated versus LPS (100 ng/mL) stimulated cells. Data is presented as a histogram (top), heat maps (middle) and 2-d bar graph of the averaged signals (bottom).

FIG. 39 depicts the results of the experiments of using the 45-plexed single cell assay comparing single-cell secretions of non-stimulated versus LPS (100 ng/mL) stimulated cells. Data is presented as a histogram (top), heat maps (middle) and 2-d bar graph of the averaged signals (bottom).

Figure 41:
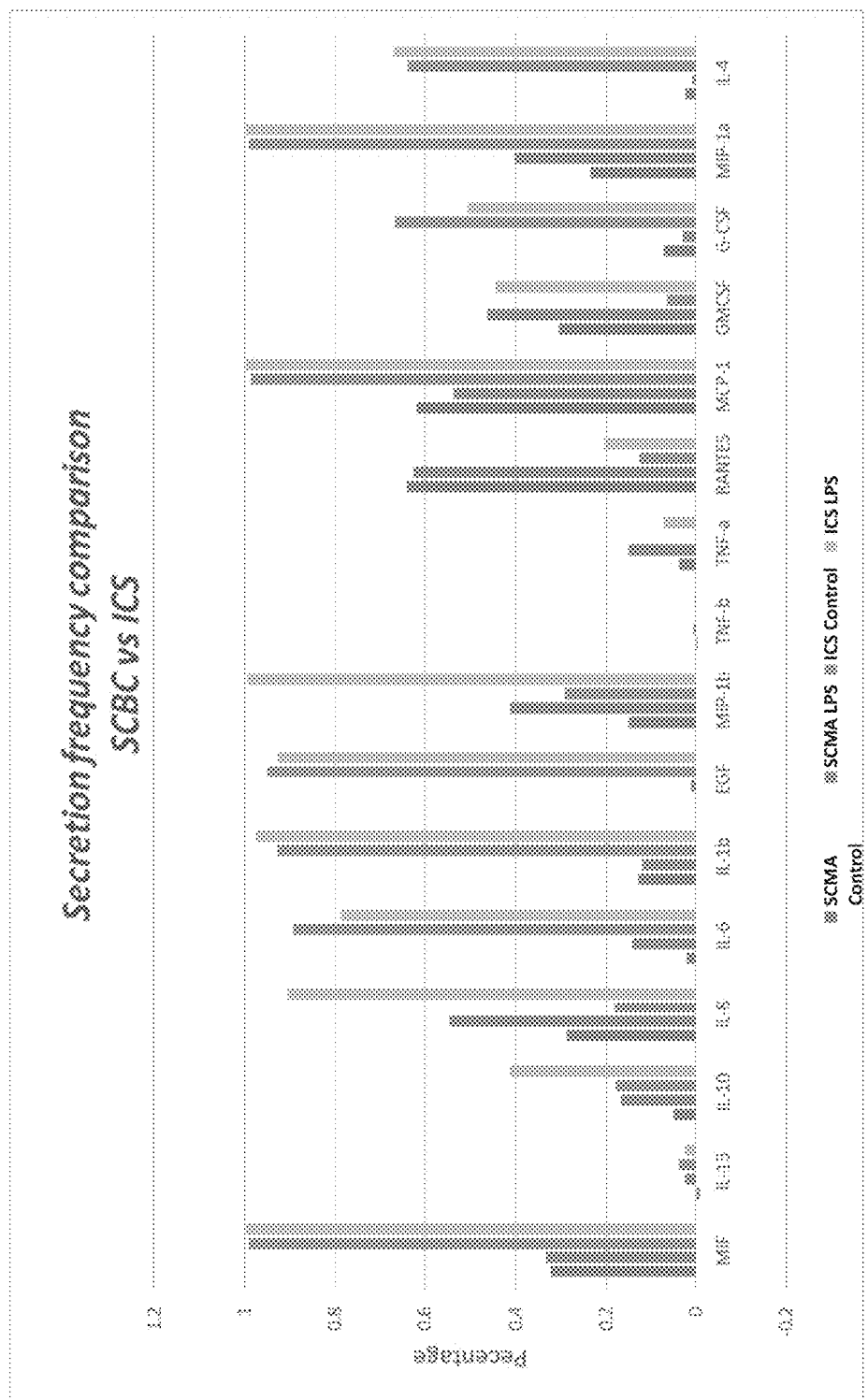
FIG. 41 is a graph comparing the single-cell assay of the invention (SCMA) with intracellular cytokine staining (ICS) in detection of cytokines in nonstimulated (control) and LPS stimulated cells.

The single cell multiplexing array assay (SCMA) was also validated against intracellular cytokine staining (ICS) (FIG. 40 and FIG. 41). It was seen that the "secretions" as detected by ICS was increased compared to the single cell secretion assay described herein. Without wishing to be bound by any particular theory, these increases in ICS may be due to the fact that this detection are predicted rather than actually secreted proteins.

Figure 42:
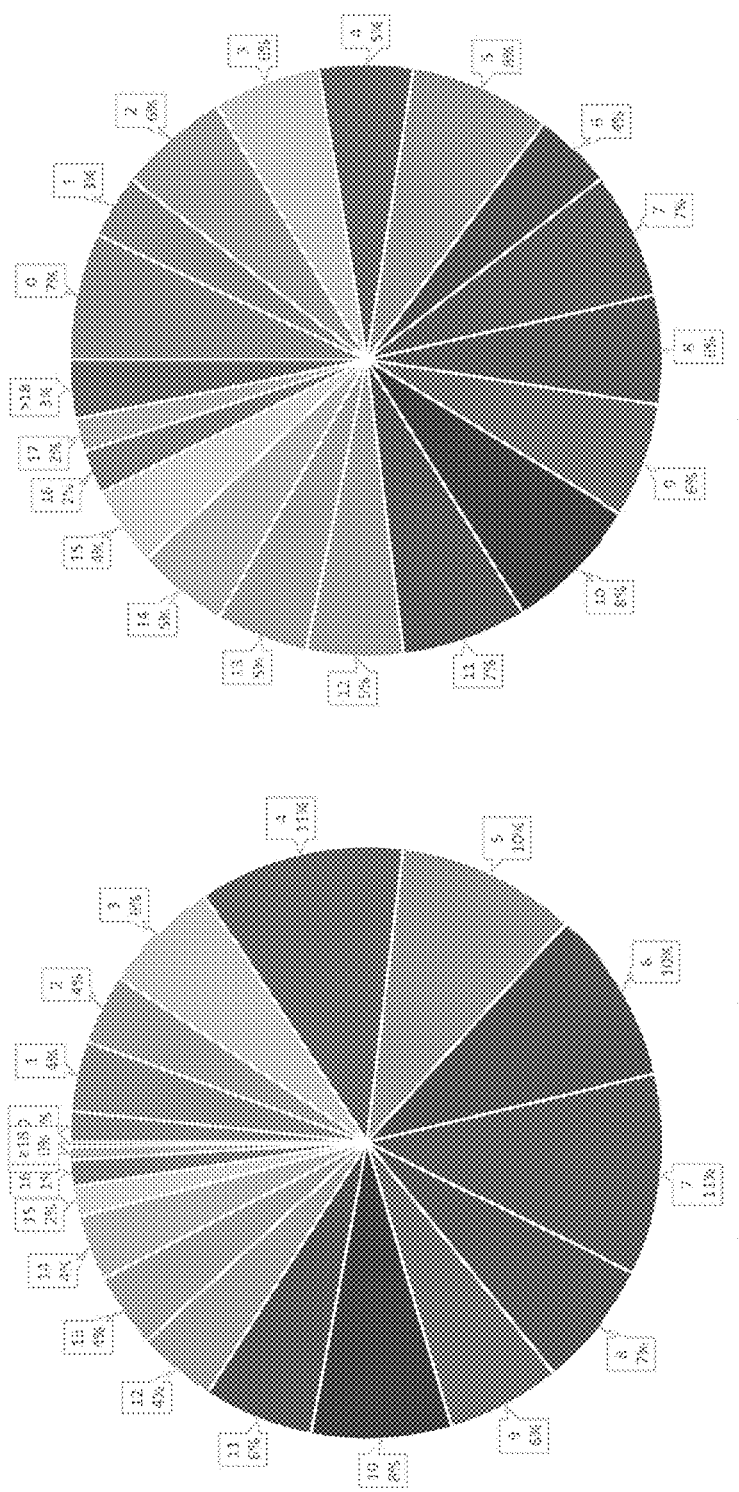
FIG. 42 is a set of graphs depicting the polyfunctionality of cells by illustrating the number of secreted cytokines per cell, as measured by the single-cell assay of the invention, for control and stimulated cells.

FIG. 42 depicts a type of data output that describes the polyfunctionality of the cells (non-stimulated versus LPS stimulated). As depicted, the graphs demonstrate the number of cytokines detected per single cell.

Example 3: IsoPlexis: A 45-Plex Single-Cell Secretion Profiling Platform to Interrogate Functional Cellular Heterogeneity ELISpot including its variant FLUOROSpot is the only technology widely used to measure true secretion of immune effector proteins from single cells and thus remains the mainstay of pre-clinical and clinical tool to assess cellular immunity. However it can measure only one or two proteins and provides minimal biological information. Therefore it fails to reveal the immune cell quality and protective ability because it is not able to capture the complete picture of functional diversity or identify the most potent polyfunctional population. A technology that can measure an array of proteins from single cells is highly desired and will help address a host of important biological and medical questions ranging from immune diversity, intratumor heterogeneity, multifunctionality, to cell-cell communication network. Such technology needs to meet all the following requirements. (i) Single cell sensitivity: proteins can be isolated and sensitively measured from a single cell. (ii) High multiplicity: a large panel (35 or more) of proteins can be simultaneously measured. (iii) High content: thousands of single cells can be analyzed in parallel. Described herein is a new technology that combines spatial multiplexing and spectral multiplexing in a sub-nanoliter chamber-based single-cell protein secretion assay. It allows for simultaneous quantification of 45 secreted proteins in contrast to only 1-2 proteins using existing ELISpot assays, which is the highest recorded multiplexing capability in single-cell proteomic assay. This platform was applied to the study of human macrophage cells in response to pathogenic ligands, LPS, poly-IC and PAM3, that activate three toll-like receptors (TLRs), respectively. Single-cell, high-plex protein profiles reveal unexpectedly large cell-to-cell variability and a three-tiered response, which was further confirmed by a compressed clustering analysis using viSNE. viSNE is a recently developed analysis based on the t-Distributed Stochastic Neighbor Embedding (t-SNE) algorithm and is a powerful tool to enable visualization, cluster of high dimensional single cell data and uncover phenotypic heterogeneity between cells (Amir et al, 2013, Nature Biotechnology, 31: 545-552, which is incorporated herein by reference in its entirety). Three functional cell subsets were identified, and the response is strongly correlated to the initial state. The first population diminished or returned to the indolent state. The second population remains largely unchanged in terms of their effector functions. The third population is strongly correlated to the elevated production of cytokines and appears to be highly multifunctional. This three-tiered response prevails in both macrophage cell lines and primary monocyte-derived macrophages, and appears to be an intrinsic non-genetic heterogeneity that determines the quality (multifunctionality) and extent (fraction) of cellular immune response to pathogenic ligands. The study presented herein demonstrates the ability of single-cell, high-plex protein profiling to reveal deep functional phenotype and heterogeneous responses to perturbagens that cannot be probed by existing technologies. This platform has great potential in both preclinical and clinical studies to evaluate cellular heterogeneity, for example, in the immune system or tumor microenvironment.

The materials and methods employed in these experiments are now described.

Fabrication of Antibody Features

The mold for PDMS replica is a silicon master etched with deep reactive-ion etching (DRIE) method. It was pre-treated with chlorotrimethylsilane (Aldrich) vapor overnight to facilitate PDMS release. PDMS prepolymer and curing agent (RTV615, Momentive) was mixed completely (parts A and B in 10:1 ratio) and poured onto the silicon master. Air bubbles were removed via vacuum desiccator for 1 h, and the PDMS was cured in the oven at 80° C. for 2 hrs. After curing, the PDMS layer was peeled off the mold and holes for inlet and outlet ports were punched. The device was cleaned via sonication in ethanol and 2-propanol before bonding with a poly-L-lysine microarray slide (Erie Scientific). The assembly was then baked in the oven at 80° C. for 2 hrs to strengthen the bonding. The PDMS microchip for antibody flow patterning contains 20 separate microchannels which can pattern up to 20 different solutions respectively. The typical width and pitch of the set of features is 25 μm, 50 μm respectively in the PDMS flow patterning microchip.

For the flow patterning of the antibody features, 2 μL of different antibody mixtures (Table 3 and FIG. 30) were injected into microchannels separately and flowed through the microfluidic channels until dry. All the antibodies used in experiments are summarized in Table 3. Antibodies are immobilized on the poly-L-lysine glass slide to form the antibody patterned feature. After flow patterning, PDMS layer is released and the glass slide is blocked with 3% BSA (Sigma) and be stored in the refrigerator at 4° C. until use.

Fabrication of Microchamber Array Chips

The mold for the microchamber array is a silicon master etched with DRIE method. It was also pre-treated with chlorotrimethylsilane (Aldrich) vapor overnight to facilitate PDMS release. The microfluidic chamber array chips for single cell capture were fabricated out of PDMS (RTV615, Momentive, parts A and B in 10:1 ratio) using soft lithography techniques. Air bubbles were removed via vacuum desiccator for 1 h, and the PDMS was cured in the oven at 80° C. for 2 hrs.

Antibody Conjugation

The 488 nm group and 532 nm group detection antibodies were covalently conjugated with Alexa fluor 488 and Alexa fluor 532 dyes respectively following the protocol provided by the supplier. The 635 nm group detection antibodies are all tagged with biotin, which can be read out using a fluorophore APC or Cy5 conjugated streptavidin or avidin through the binding of streptavidin/avidin with biotin.

Cell Culture and Stimulation

Human U937 cell line was purchased from ATCC (American Type Culture Collection, ATCC) and cultured in RPMI 1640 medium (Gibco, Invitrogen) supplemented with 10% fetal bovine serum (FBS, ATCC). The U937 cells were differentiated with 50 ng/mL phorbol 12-myristate 13-acetate (Fisher) for 48 hrs. Media was then changed and replaced with normal medium for 36 hrs. The cells were harvested with trypsin for single cell experiment. The cells were challenged with 100 ng/mL lipopolysaccharide (Calbiochem) to activate Toll-like receptor 4 (TLR4) (or other activation reagents like PAM3, poly IC) signaling just before its suspension was pipetted onto PDMS microwell array.

Intracellular Cytokine Staining

Cells are harvested and seeded into tissue culture petri dish in $10^6$ density with both control and treated cells. After 2 hrs, the secretion inhibitor Brefeldin A (Biolegend) was added. The cells are then incubated for 22 hrs before harvested for intracellular flow cytometry. Cells were fixed and stained according to manufacturers' instructions.

Single Cell Trapping with PDMS Microwell Array

Before performing the single cell trapping experiment, the PDMS microwell array and antibody-containing glass slide were blocked with 3% BSA solution (Sigma) respectively for 2 hrs and then rinsed with fresh cell medium. Cells were suspended in fresh medium just before cell capture. The PDMS microwell array was placed facing upward and cell culture medium solution was removed until a thin layer was remained on the PDMS microwell array surface. Cell suspension was pipetted (50-200 μL) onto the microwell array and allowed to settle for 10 mins so that cells would fall into the microwells. The antibody glass slide was put on the top of PDMS microwell array with antibodies resting facing the cell capture chambers. Then the PDMS microwell array and glass slide were clamped tightly with screws. Single cells are thus trapped in the microwell array and the assembly was allowed to incubate to allow cells to secrete proteins. After the trapped cells were incubated for 24 hours, the screws were released to remove the antibody glass slide, and ELISA immunoassay procedures were performed and the results were detected and analyzed with Genepix scanner and software.

Population Micro Array

Cell population assay was performed on custom printed antibody microarray, which was spotted with a Spotbot 3 microarrayer (Arrayit) on poly-L-lysine glass slides. Twelve identical subgroups which had the same antibody pattern were printed on each glass slide. After printing, the antibody glass side was kept in a wet box (containing saturated NaCl solution at 75% relative humidity) for 5 hours. Before cell population assay, the glass side was bonded with a PDMS microwell slab and blocked with 3% BSA solution for 2 hours. Then cell culture supernatant was added into different microwells and allowed to incubate for 1 hour. Following incubation, ELISA immunoassay procedures are performed, and the results were detected and analyzed with Genepix scanner and software.

Immunoassay Procedures

ELISA procedures were followed to translate cytokines secreted by single cells into detectable signals. A mixture of biotinylated detection antibodies (Table 3) were pipetted onto the glass slide and incubated for 1 hr at room temperature to complete the sandwich immunoassay followed by washing with 3% BSA solution. APC dye-labeled streptavidin (eBioscience, 200 µL, 5 µg/mL) was added onto glass slide and incubated for another 30 min. Following, the glass slide was washed with 3% BSA again and blocked with 3% BSA for 0.5 hr. Following the BSA blocking, the glass slide was dipped in DPBS, DPBS, DI water, DI water sequentially and finally blown dry.

Fluorescence Detection and Analysis

Genepix 4200A scanners (Molecular Devices) were used to obtain scanned fluorescent images for FITC and APC channels. Three color channels 488 (blue), 532 (green) and 635 (red) were used to collect fluorescence signals. The image was analyzed with GenePix Pro software (Molecular Devices) by loading and aligning the microwells array template followed by extraction of fluorescence intensity values. Fluorescence results were extracted with the image analysis tool in GenePix Pro. The fluorescence results were then matched to each of the chambers of the sub-nanoliter microchamber array chips analyzed via optical imaging.

Automated Optical Image Analysis and Cell Counting

The assembly was imaged on Nikon Eclipse Ti microscope with an automatic microscope stage to acquire optical images (both darkfield and oblique view) recording the number and location of cells in each microwell. The darkfield image will be used to define the location and sequence of each microchamber and oblique image will be used to define the cell numbers and their locations. Both images can be processed in Nikon software (NIS-Elements Ar Microscope Imaging Software) by defining threshold on each image to realize automated cell counting. The cell counts will then be matched with the extracted fluorescent data to their respective cell chambers.

Data and Statistical Analyses

All fluorescent scanned slides were processed with Genepix software to extract average fluorescent signal for all features in each set. A home developed Matlab (MathWorks) code was created for automated extraction of fluorescent data and generation of scatterplots. Excel (Microsoft) and OriginPro 8 (OriginLab) was used to compile extracted data. Heatmaps and unsupervised clustering were generated from the extracted data using the software Cluster/Treeview (Eisen Laboratory). Statistical analysis was conducted in R (R Development Core Team).

The results of the experiments are now described.

Figure 43:
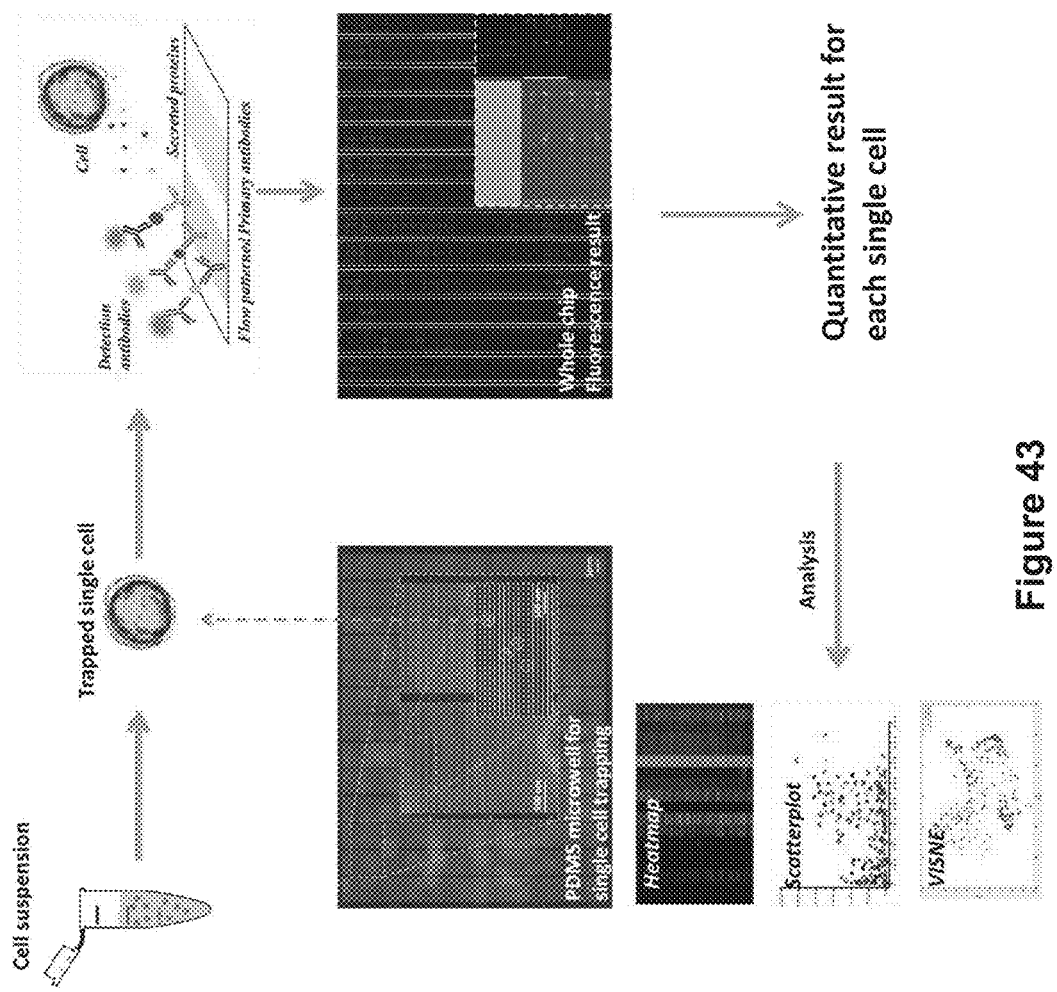
FIG. 43 depicts a workflow illustration of the 45-plexed single cell protein secretion profiling system.

Experiments were conducted using the 45-plexed single-cell protein secretion profiling platform, described herein (FIG. 43). A cell suspension is pipetted onto the surface of the PDMS microwell array chip, during which the cells fall into the microchambers by gravity. Then the flow patterned 45-plexed antibody immobilized glass slide is placed facing down on top of the microchambers to ensure antibody features are perpendicular to microchambers. Zero to dozens of cells are trapped in microchambers during this process. The captured cell number fits into Poisson distribution. Finally this assembly is clamped together by two transparent plastic plates with six screws. A motorized phase-contrast microscope is used to image the assembly to record the cell number and location in each microchamber. It is then placed in a tissue culture incubator for 24 hours for cells to secret proteins. Proteins secreted from individual cells during this period are captured by the antibodies, transformed into detectable signals by reacting with corresponding detection antibodies afterwards and read out by fluorescence scanner finally. The fluorescence signals are quantified, corresponded with each single cell and analyzed to be presented by heatmap, scatterplot or VISNE.

Figure 47A:
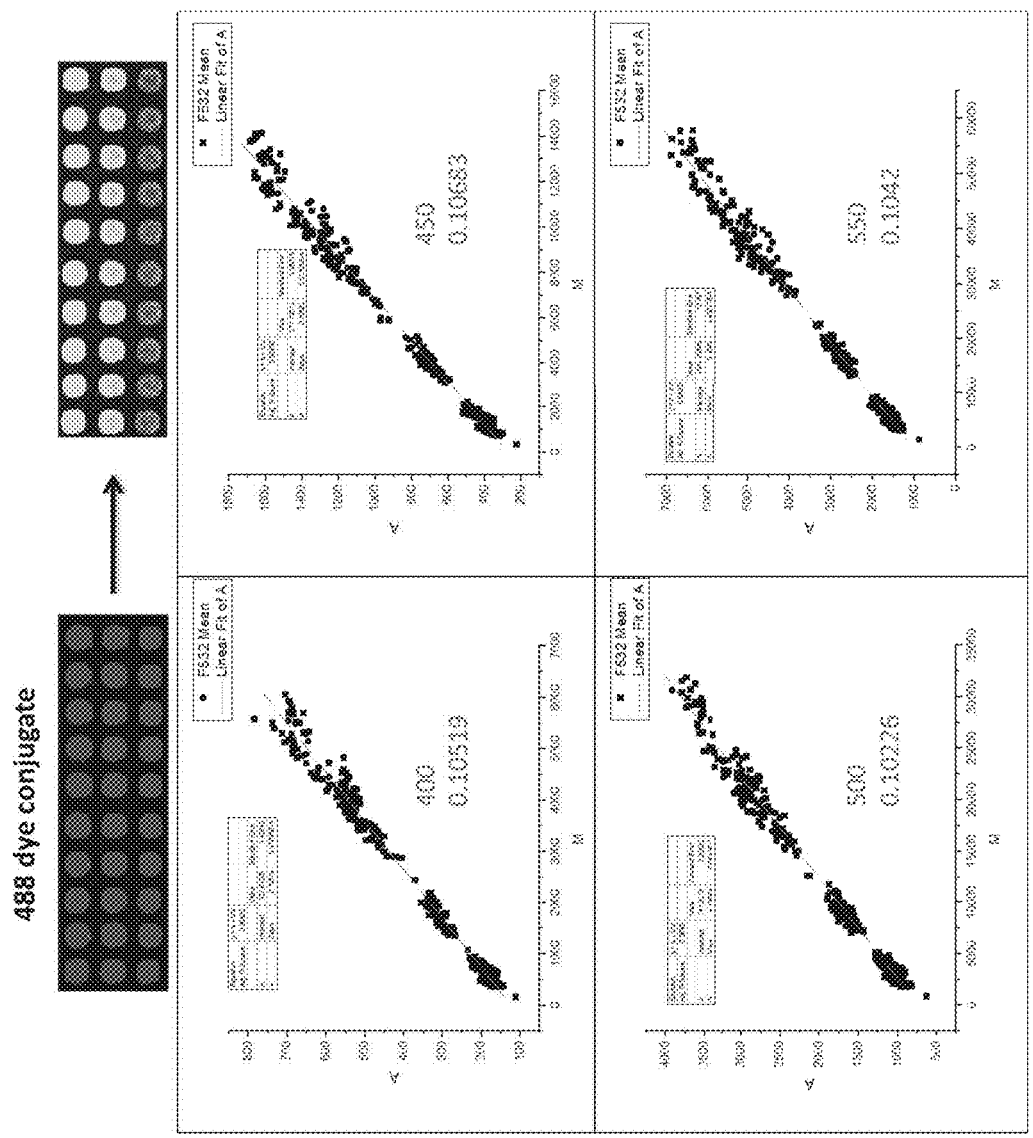
FIGS. 47A-47B depict the results from experiments investigating the compensation between Alexa fluor 488 and 532 conjugate.
Figure 47B:
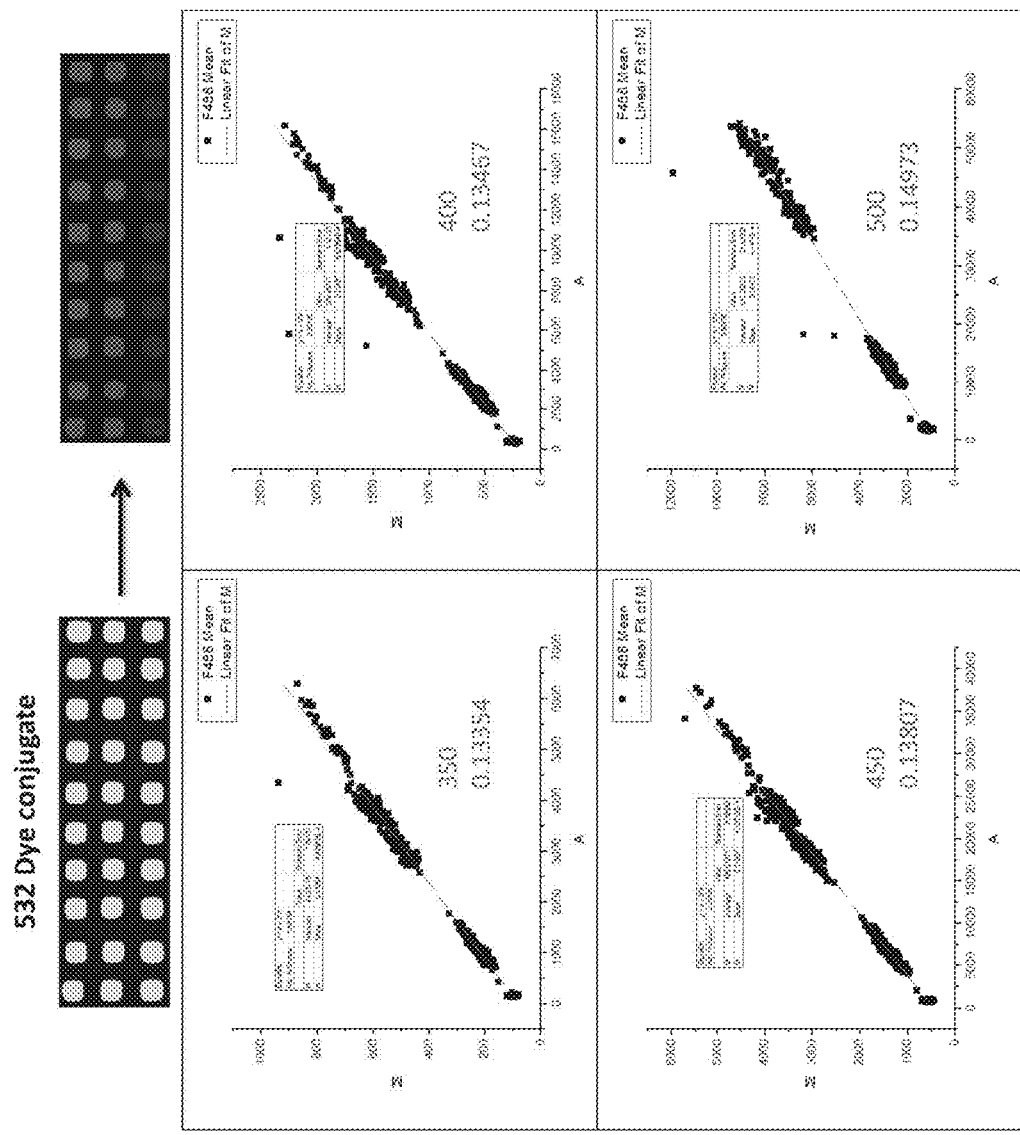

The cross-talk or spectral overlap between the 488 and 532 channels was accounted for. Due to spectral overlap between Alexa fluor 488 and 532 dyes, this glass slide will get fluorescence signal from both 488 channel (real signal) and 532 channel (crosstalk). The 488 channel signal and 532 channel signal showed good and stable correlation between each other ($R2 \approx 98\%$) and compensation equation can be extracted (FIG. 47A). Similar results were observed when observing a 532 channel real signal and 488 channel cross talk (FIG. 47B).

Figure 48:
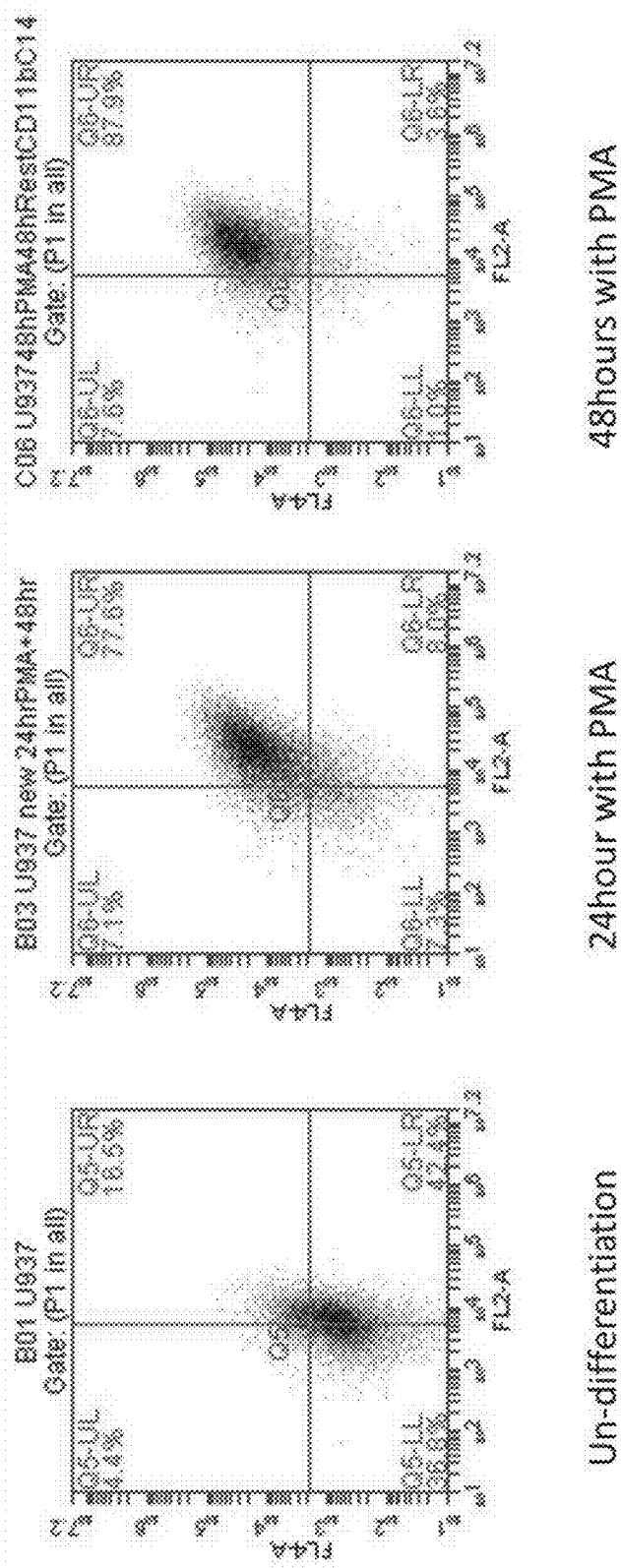
FIG. 48 is a set of graphs depicting the characterization of PMA (50 ng/mL) differentiation of U937 monocyte for 48 hrs with macrophage markers CD11b (FL4) and CD14 (FL2).

The differentiation of U937 monocytes with PMA was evaluated by detecting expression of macrophage markers CD11b(FL4) and Cd14 (FL2) (FIG. 48).

Figure 49:
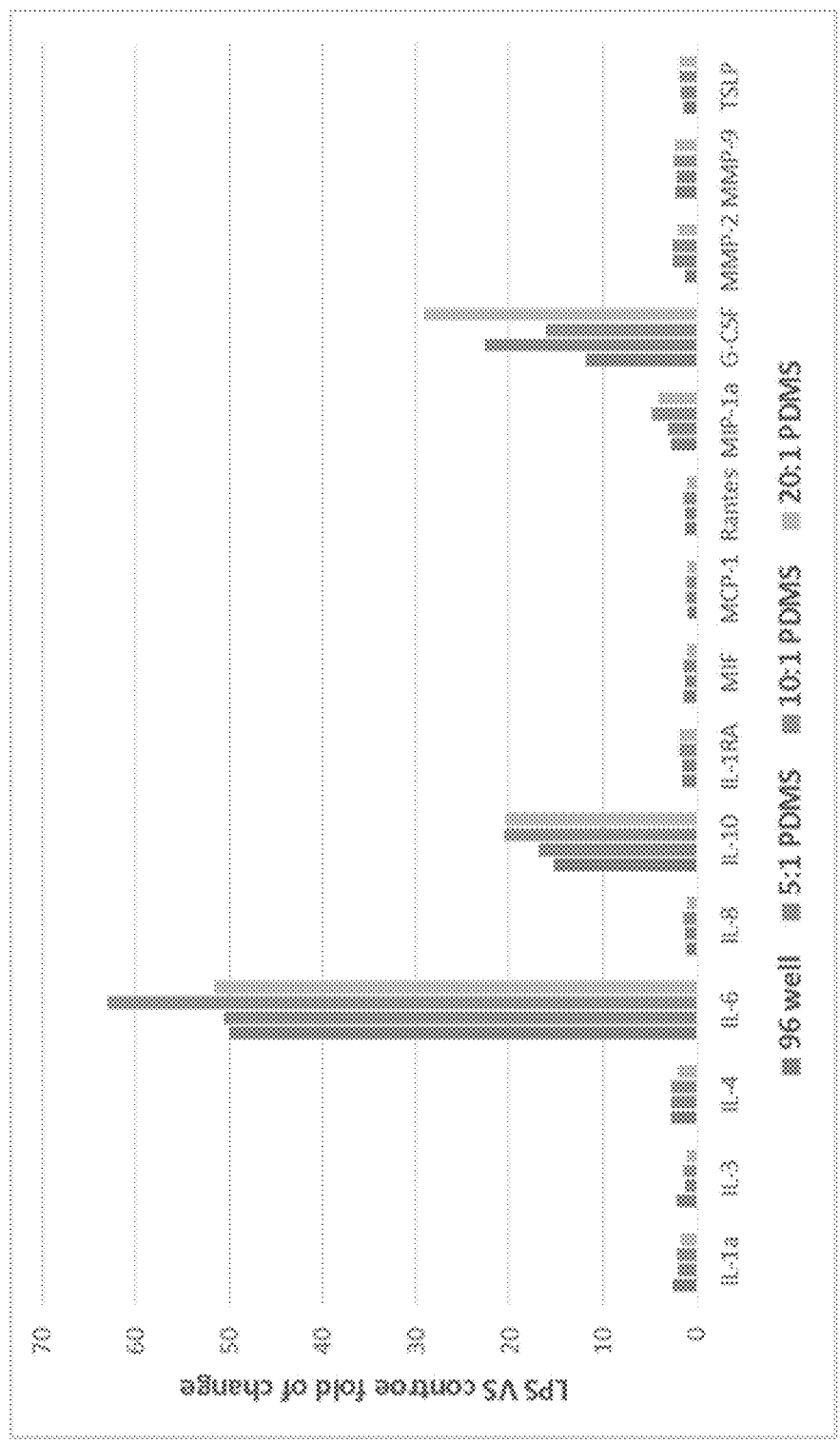
FIG. 49 is a graph depicting the results of experiments comparing U937 monocyte derived macrophage population cells protein secretion results from different substrates including 96 well plate, PDMS in 5:1, 10:1, 20:1 ratio respectively. The results shows similar fold of change in different substrates for both high level secretion proteins like IL-8, MCP-1, IL-6 and low level secretion proteins like IL-1a, IL-3, IL-4.

Experiments were conducted to examine U937 monocyte derived macrophage population cells protein secretion results from different substrates including 96 well plate, PDMS in 5:1, 10:1, 20:1 ratio respectively. The results shows similar fold of change in different substrates for both high level secretion proteins like IL-8, MCP-1, IL-6 and low level secretion proteins like IL-1a, IL-3, IL-4 (FIG. 49).

Figure 50:
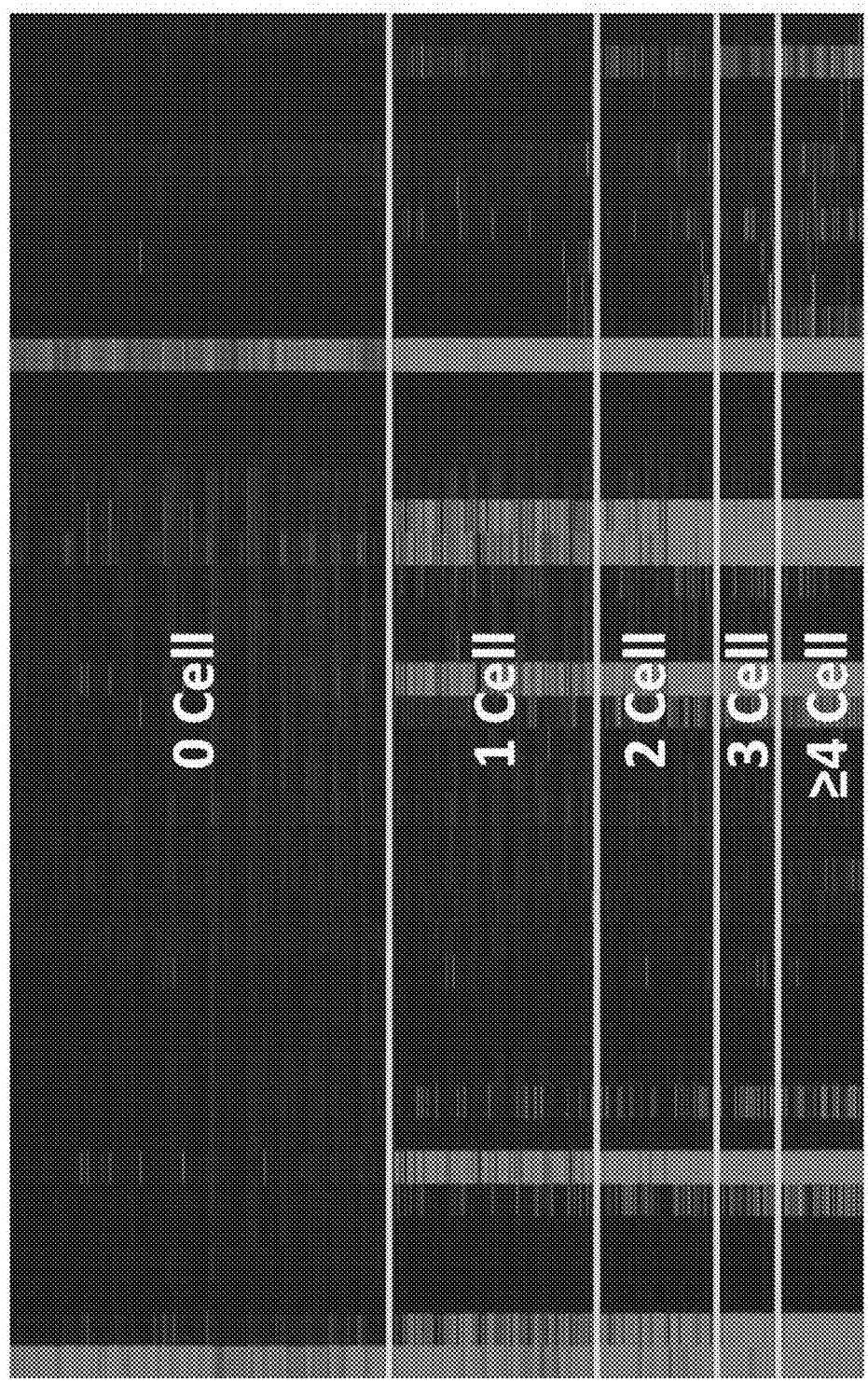
FIG. 50 is a representative whole microchip heat map (from one experiment) that shows the secretion results from different cell numbers including 0 cells, single cell, 2 cells and multiple cells ($\geq 3$). Each row is a single cell and each column corresponds to a protein of interest. The signal from 0 cell microchambers can be used as threshold (average signal plus two times standard deviation) for positive secretion.
Figures 51A, 51B:
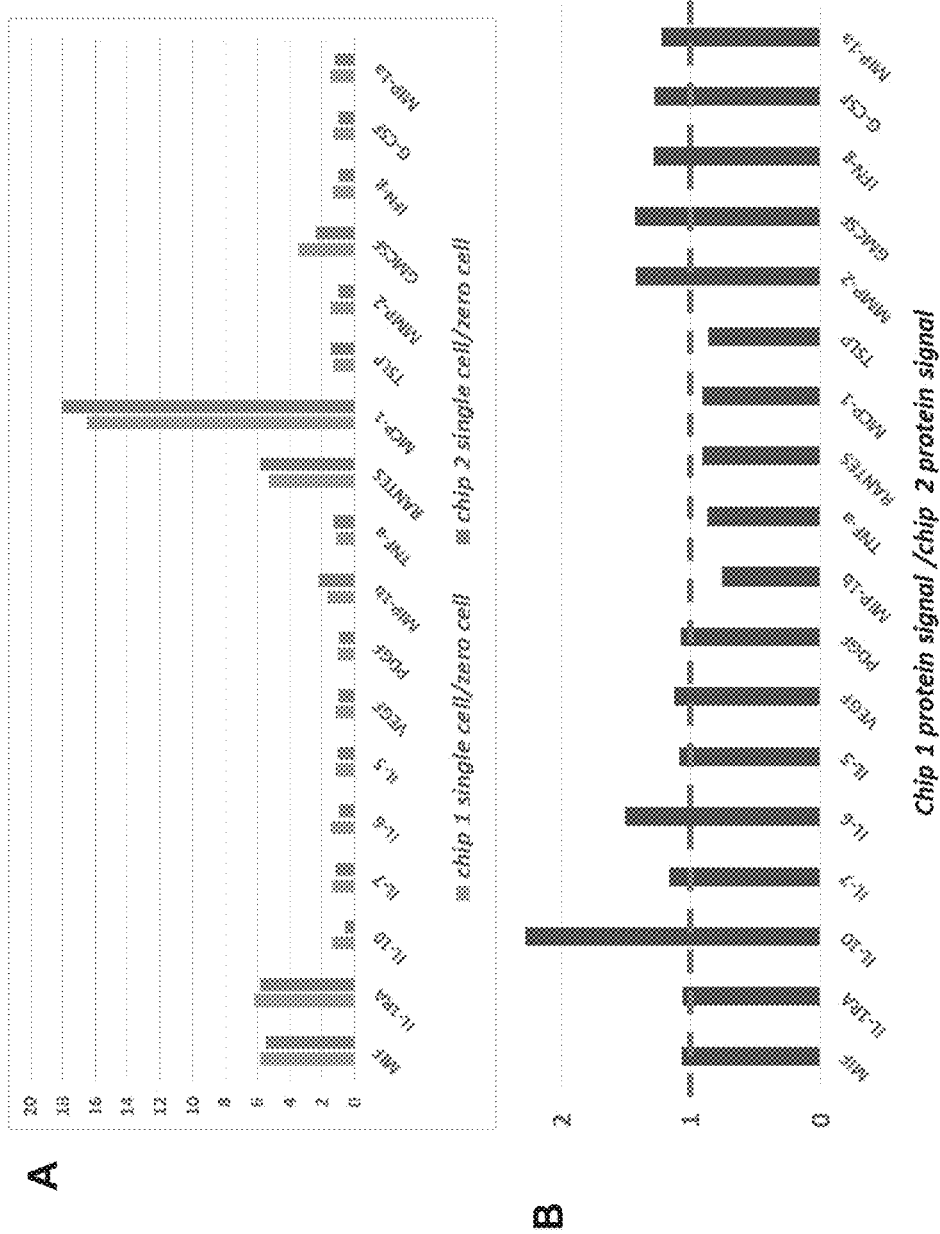
FIGS. 51A-51B show a set of graphs demonstrating the comparison of U937 monocyte derived macrophage single cell protein secretion results from parallel two chips.
Figure 52:
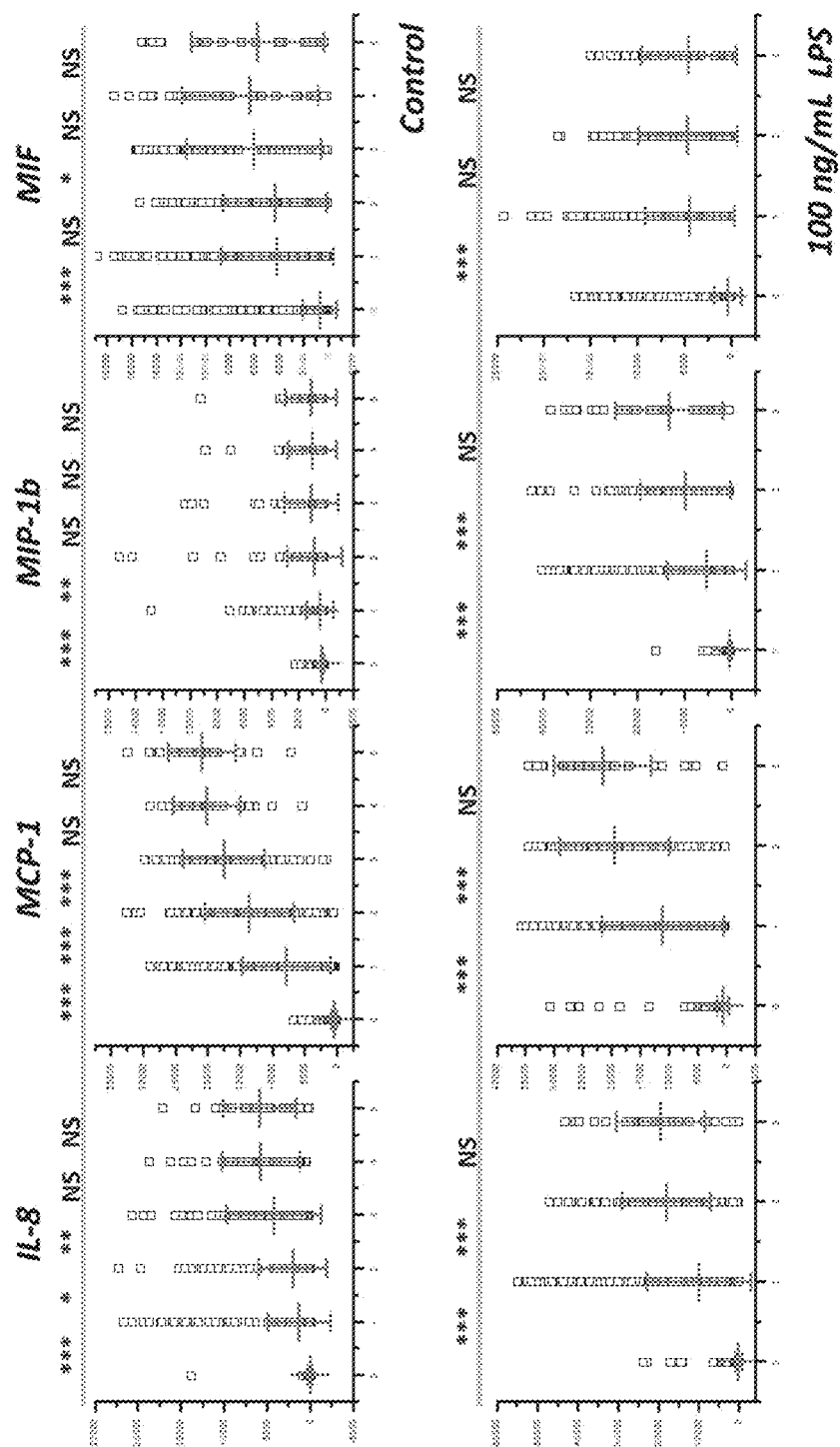
FIG. 52 is a set of graphs depicting the correlation between U937 macrophage protein secretion (IL-8, MCP-1, MIP-1b, MIF as examples) and cell numbers (0, 1, 2, 3 . . . ).

The heat map of secretion can be visualized as organized by the amount of cells contained with the chamber (FIG. 50). The signal from the 0 cell chambers can be used as a threshold (average signal plus two times standard deviation) for positive secretion. The data was analyzed to examine the correlation between secretion and cell number (FIG. 52). Experiments were also conducted to compare single cell secretion results between two different chips (FIG. 51), which demonstrates that the chips produce very similar results.

Figure 44A:
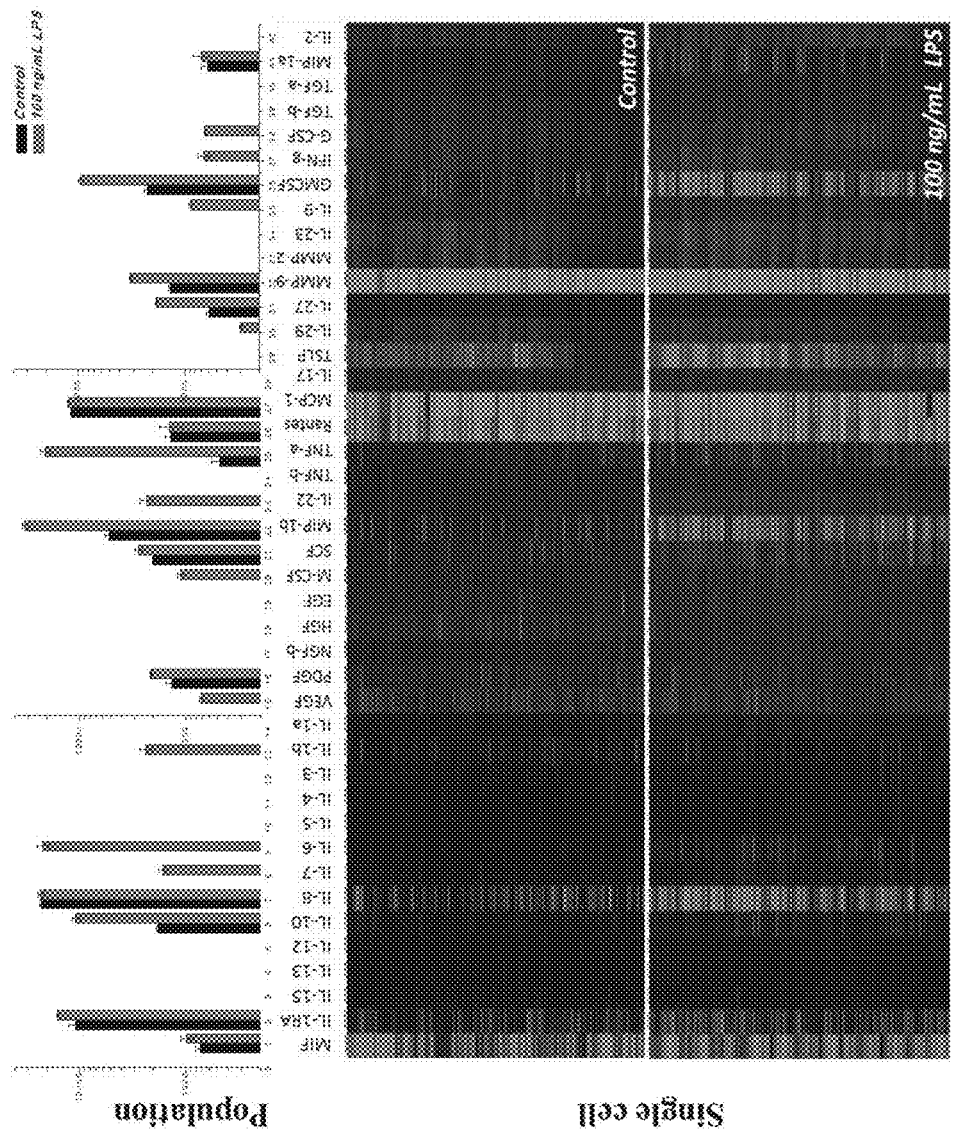
FIGS. 44A-44D depict the results of experiments demonstrating U937 macrophage single cell results on the 45-plexed protein secretion profiling platform.
Figure 44B:
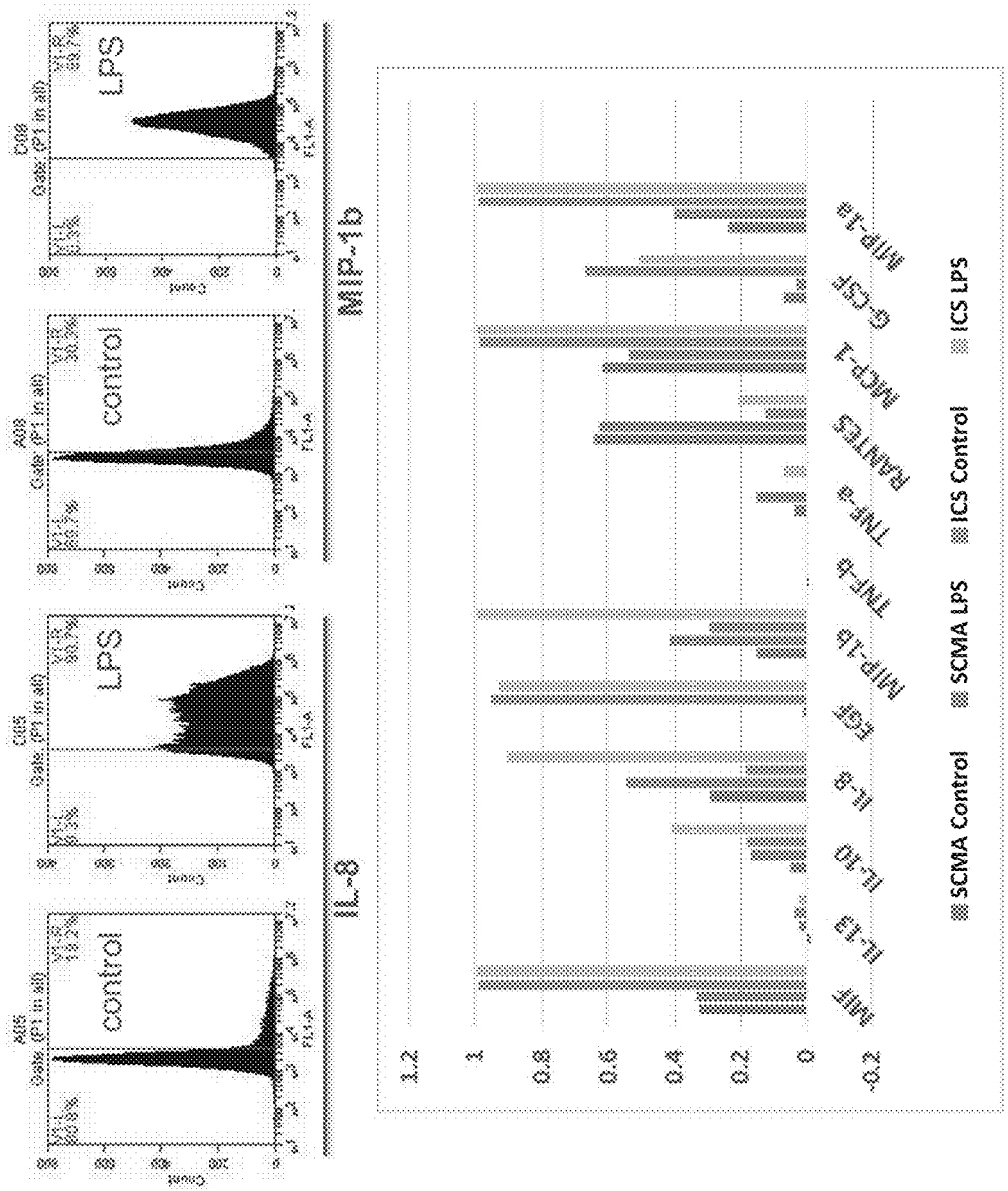

The device was used to analyze the secretion of proteins from U937 macrophages. The dynamics of protein secretion over the 48 hours incubation is demonstrated in FIG. 55, which shows that different proteins have different secretion dynamics. FIG. 44 demonstrates stimulated or unstimulated (control) protein secretion from U937 macrophages using various methods. For example, FIG. 44A depicts a comparison of U937 derived macrophage single cell protein secretion results with its population cells secretion results. Generally speaking, these two results showed good correlation with each other. Interestingly, several differences were also observed. For example, IL-8 intensity was observed to be very similar between control and stimulation cells in population result. However, the single cell results, observed using the described single-cell array demonstrated that LPS stimulated cells in fact have much higher secretion frequencies than control cells. This was also validated with intracellular cytokine staining (FIG. 44B). A comparison of protein secretion frequency obtained from single cell secretion platform and ICS (intracellular cytokine staining) is depicted in FIG. 44B.

Figure 44C:
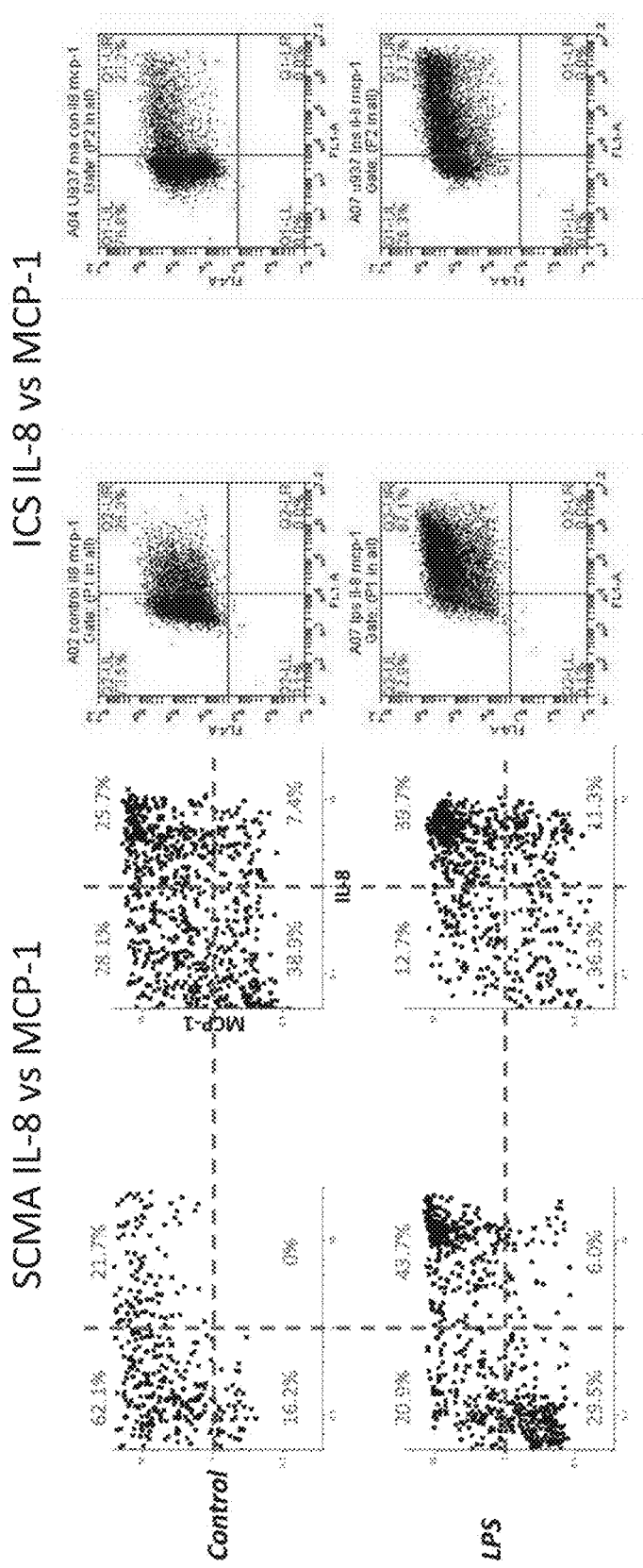
Figure 44D:
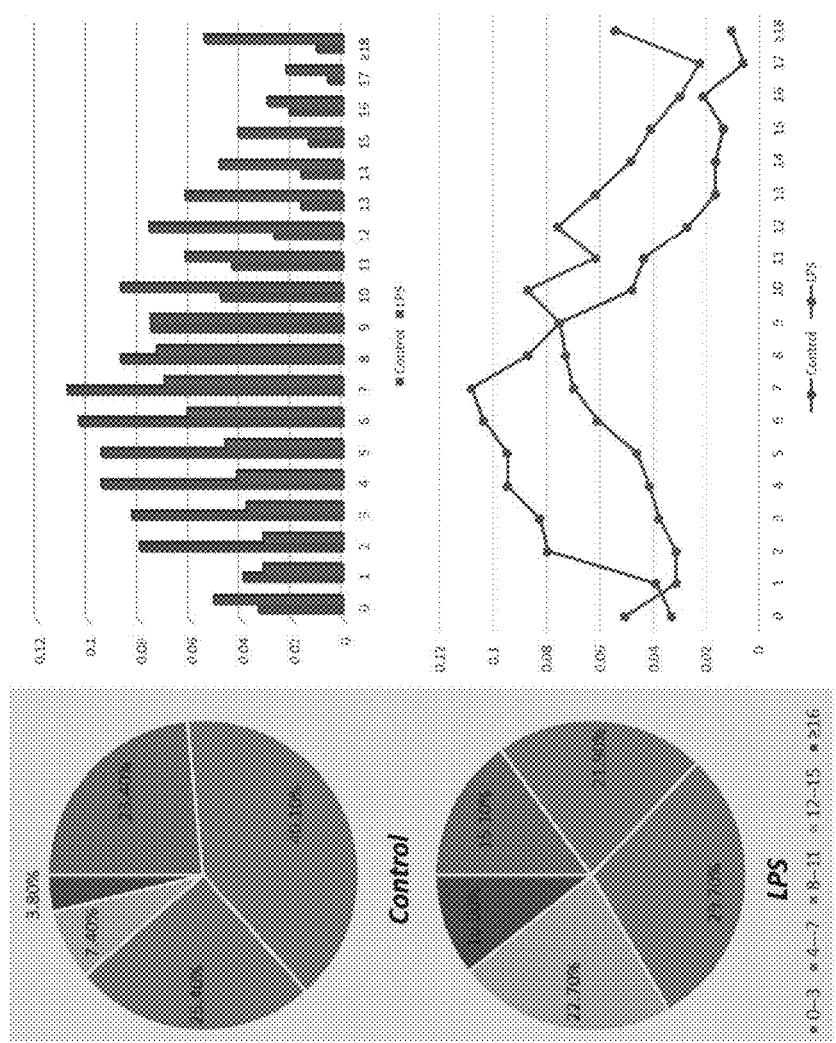

Similar cell subpopulation definitions defined by IL-8 and MCP-1 protein secretion results was observed both by SCMA and ICS (FIG. 44C). The single cell secretion platform was used to examine polyfunctionality of cells. U937 macrophage single cell polyfuncationality analysis based on their protein secretion results demonstrated that a wide variety of single cell polyfunctionality was observed and U937 derived macrophage cells showed more polyfunctionality upon the activation of TLR-4 via LPS stimulation (FIG. 44D).

Figure 53A:
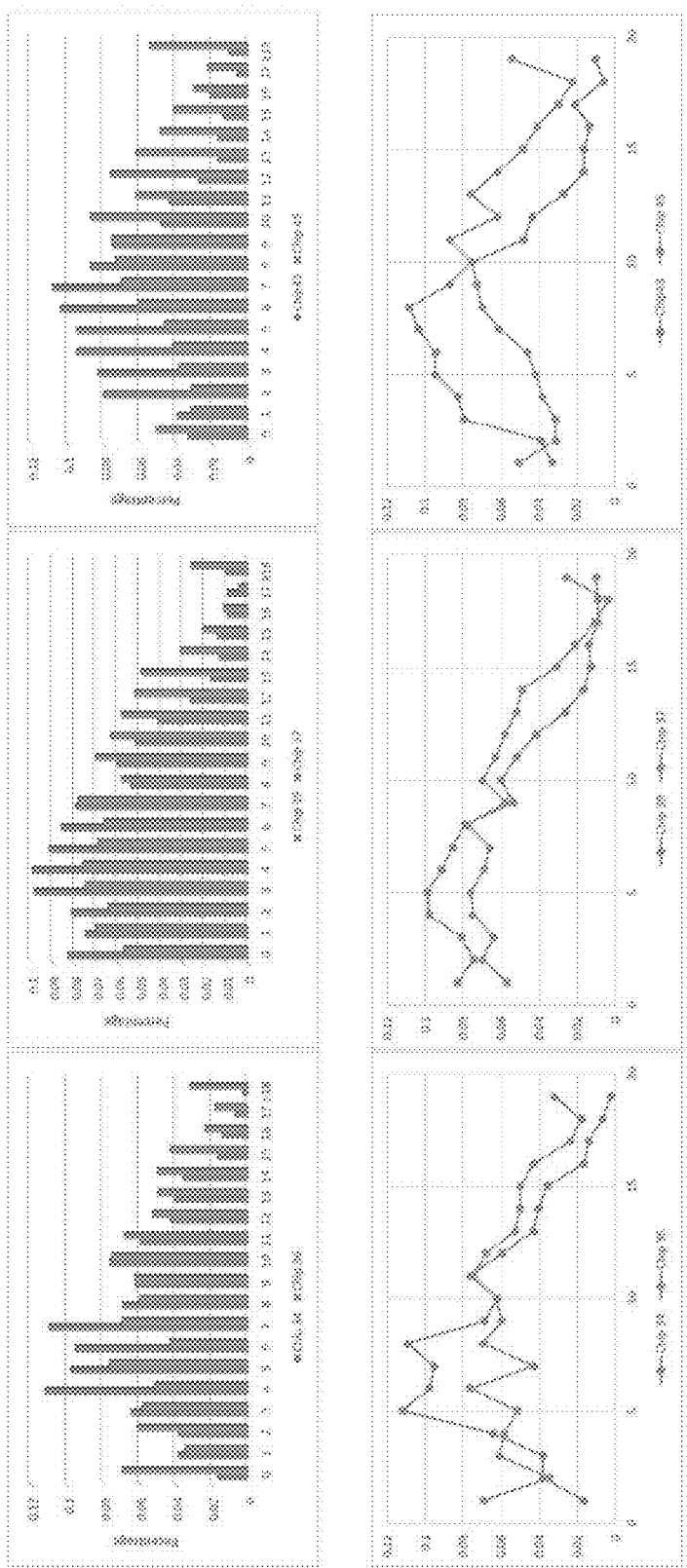
FIGS. 53A-53B depict the results of polyfunctionality analysis of U937 macrophage (control and LPS stimulated).
Figure 53B:
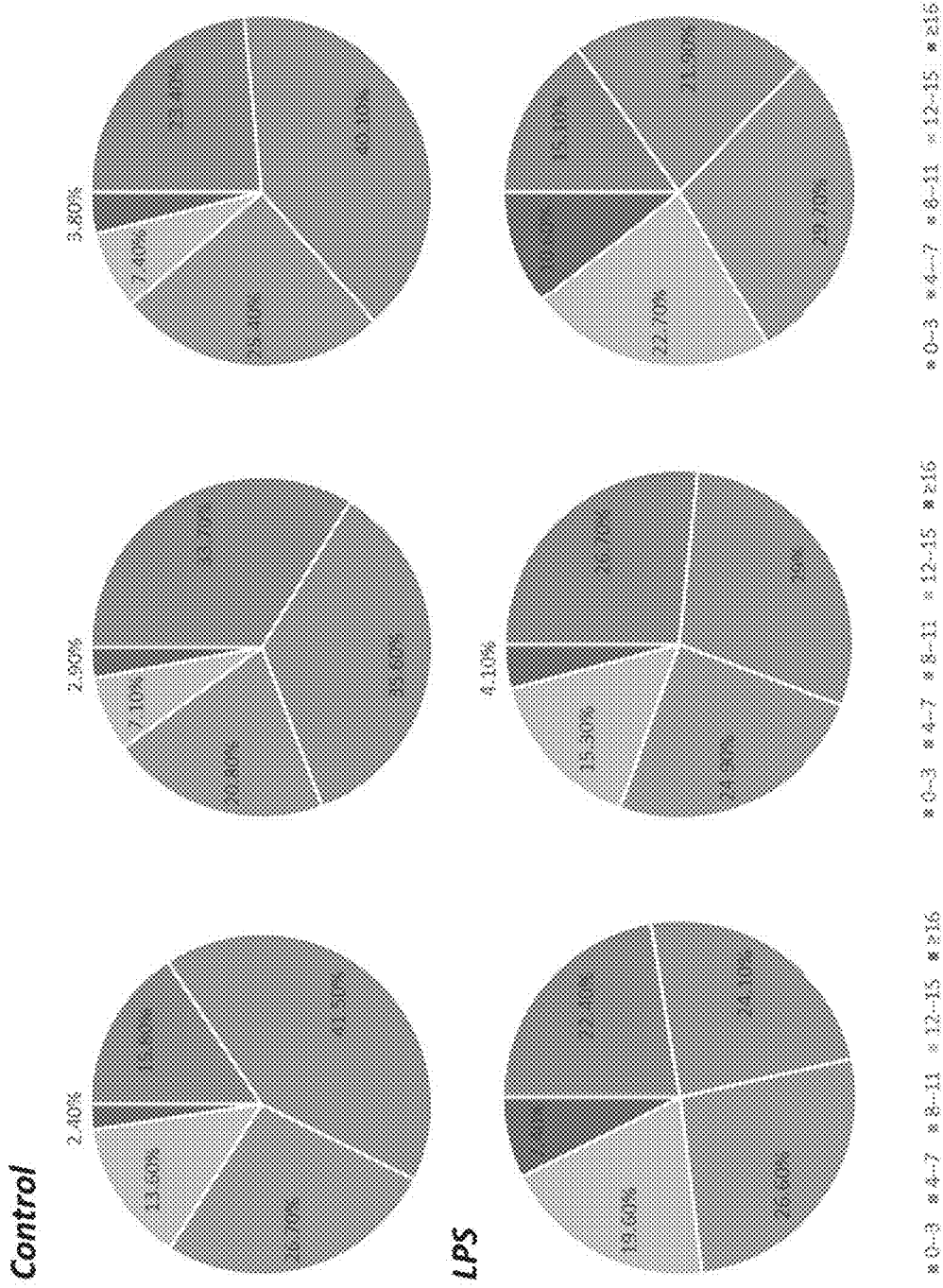

Polyfunctionality of the cells is further demonstrated in FIG. 53, which demonstrates a wide variety of single cell poyfunctionality and increased polyfunctionality upon LPS stimulation. This result was verified in three independent experiments.

Figure 45A:
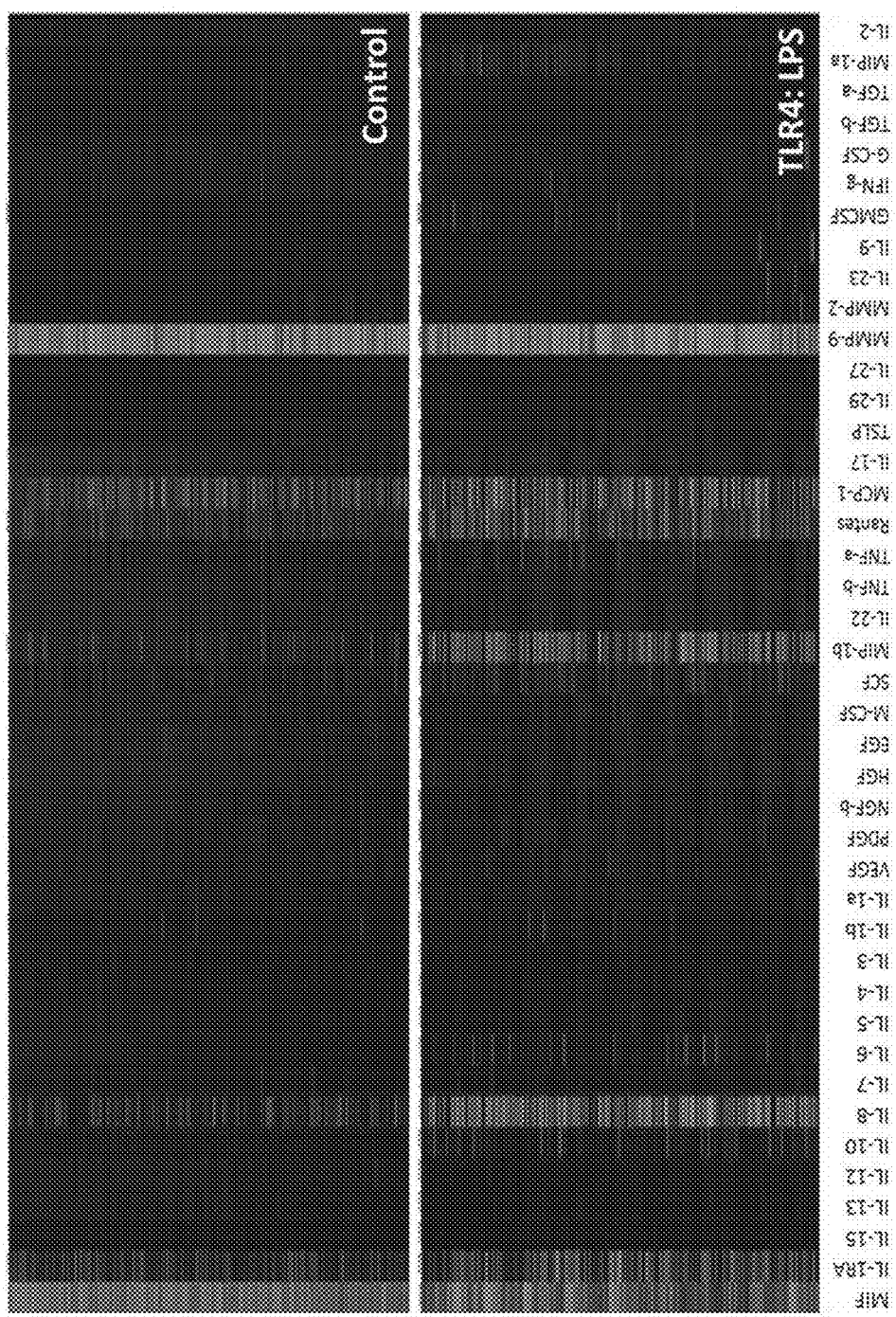
FIGS. 45A-45C depict the results of experiments demonstrating the macrophage response upon TLR 4 ligand LPS stimulation.
Figures 45B, 45C:
Figure 54:
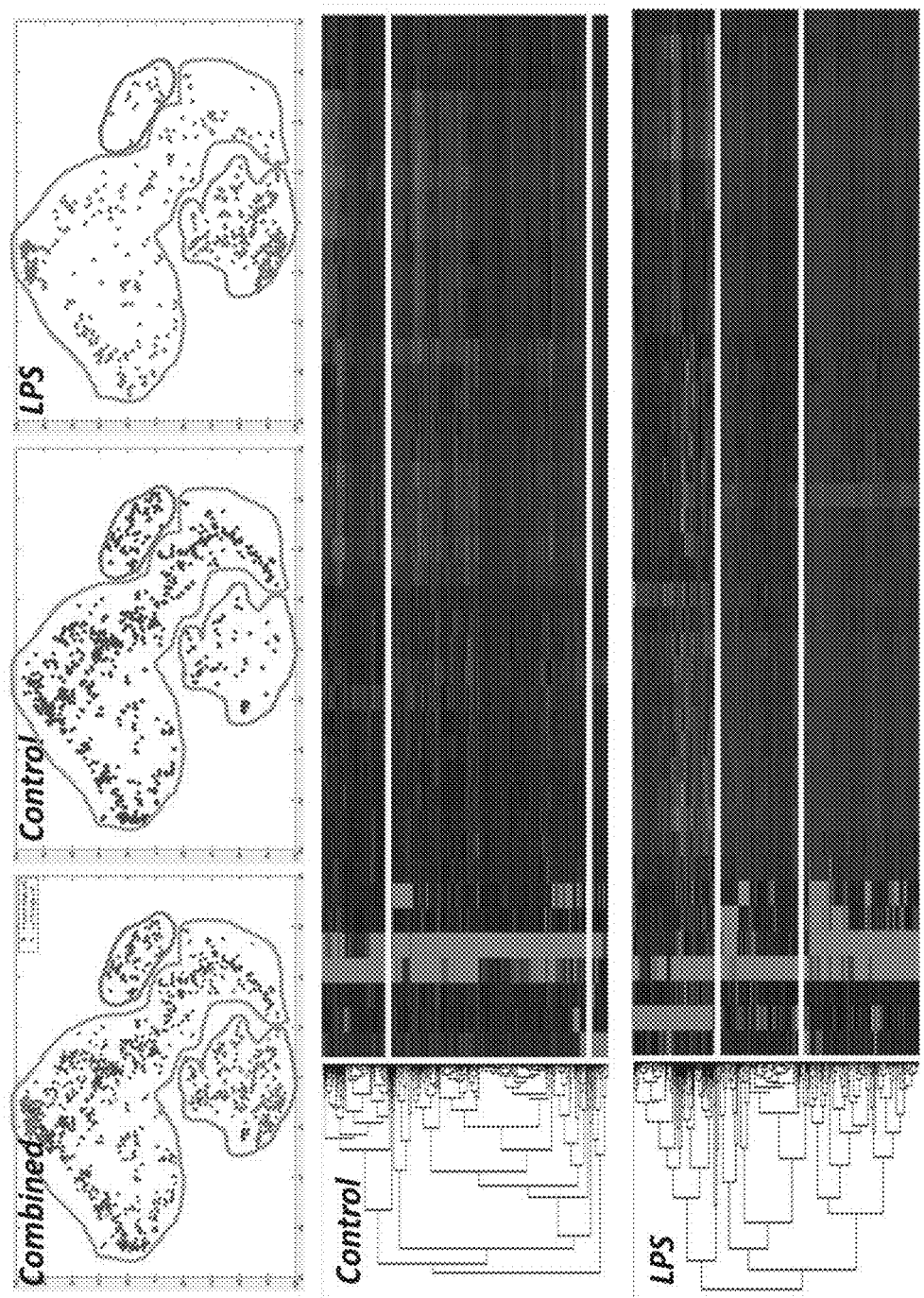
FIG. 54 depicts the comparison of VISNE and cluster results. Both untreated and LPS stimulated U937 single cells can be grouped into 3 subpopulations with these two methods based on their protein secretion patterns.
Figure 55A:
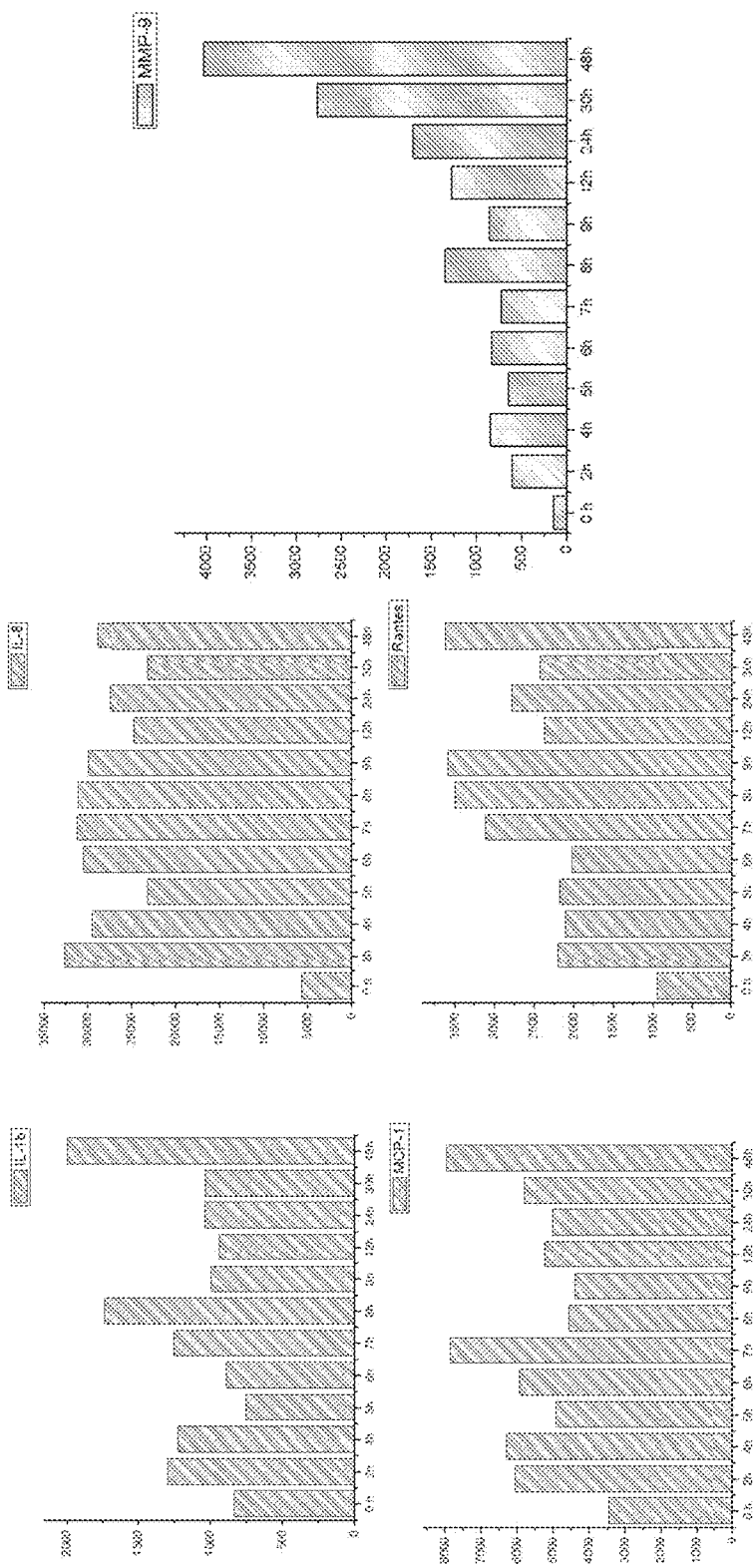
FIGS. 55A-55B show a set of graphs demonstrating U937 macrophage protein secretion dynamics between 0-48 hrs.
Figure 55B:
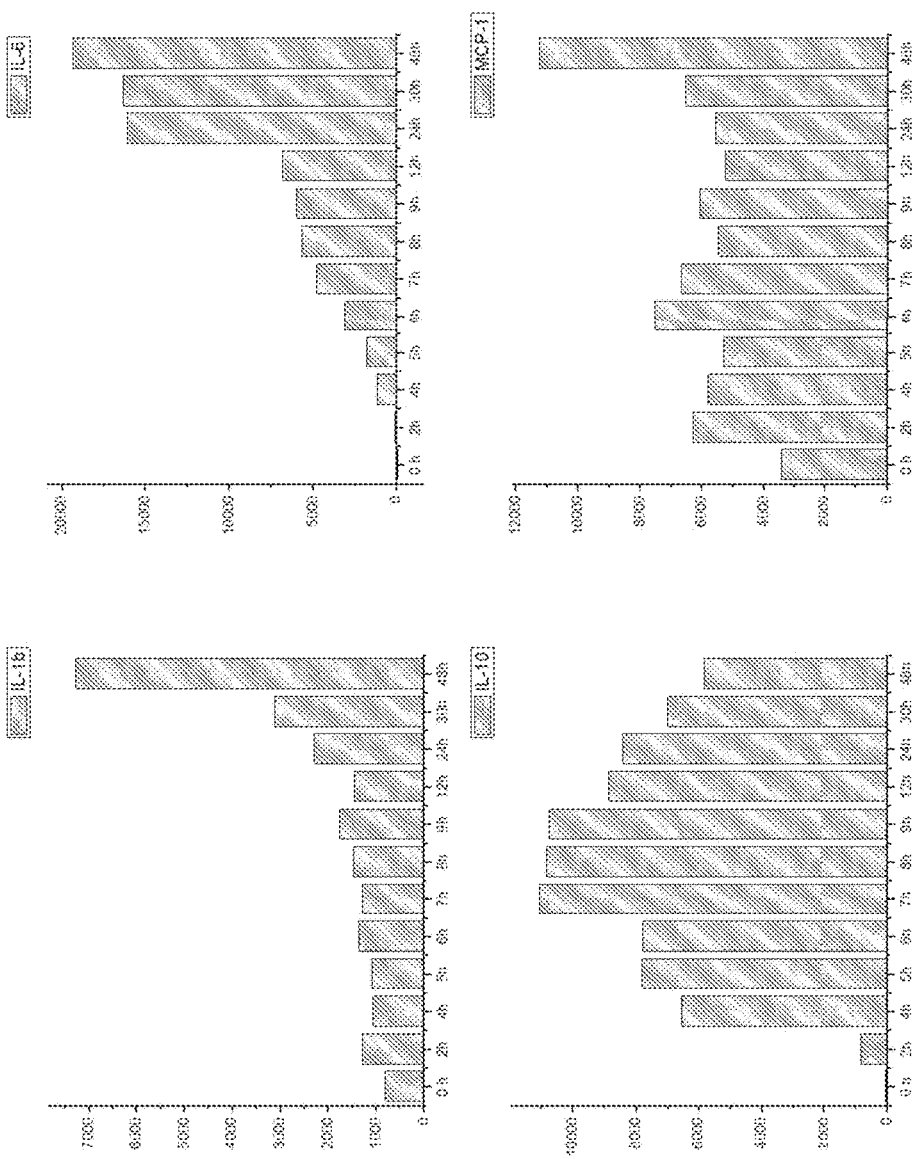
Figure 55B:
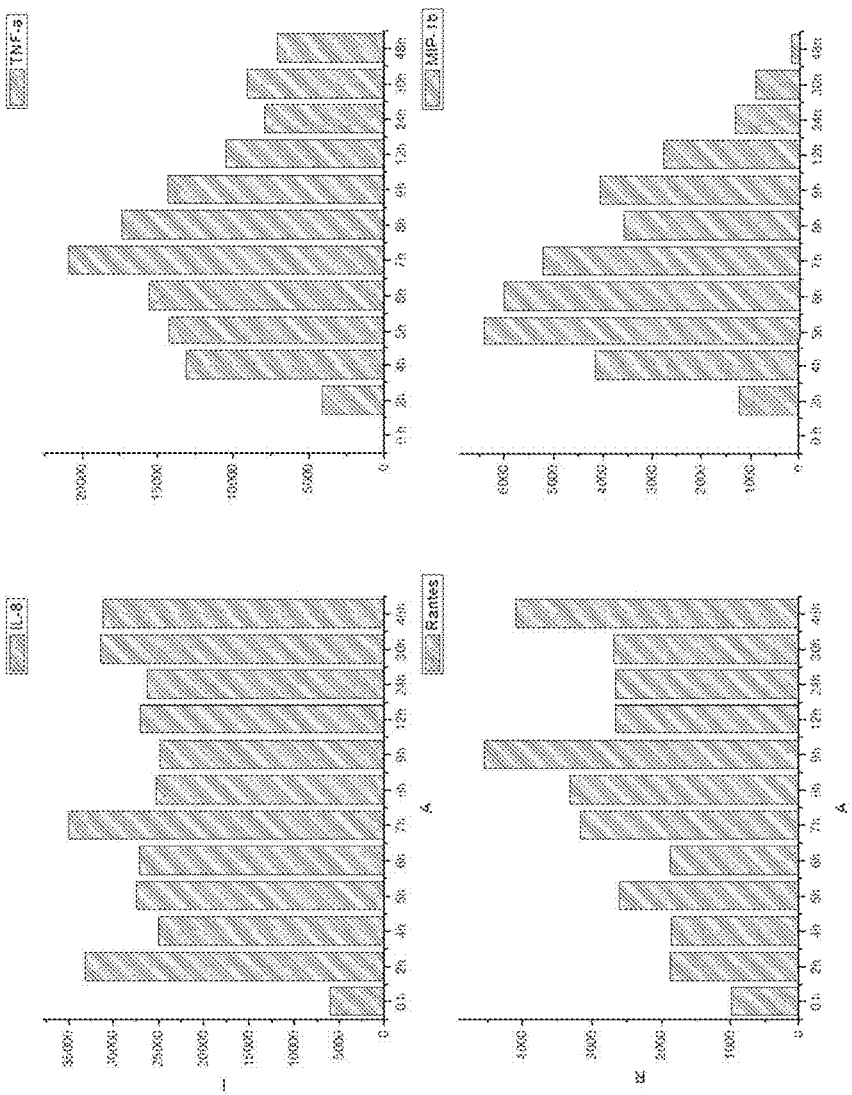
Figure 55B:
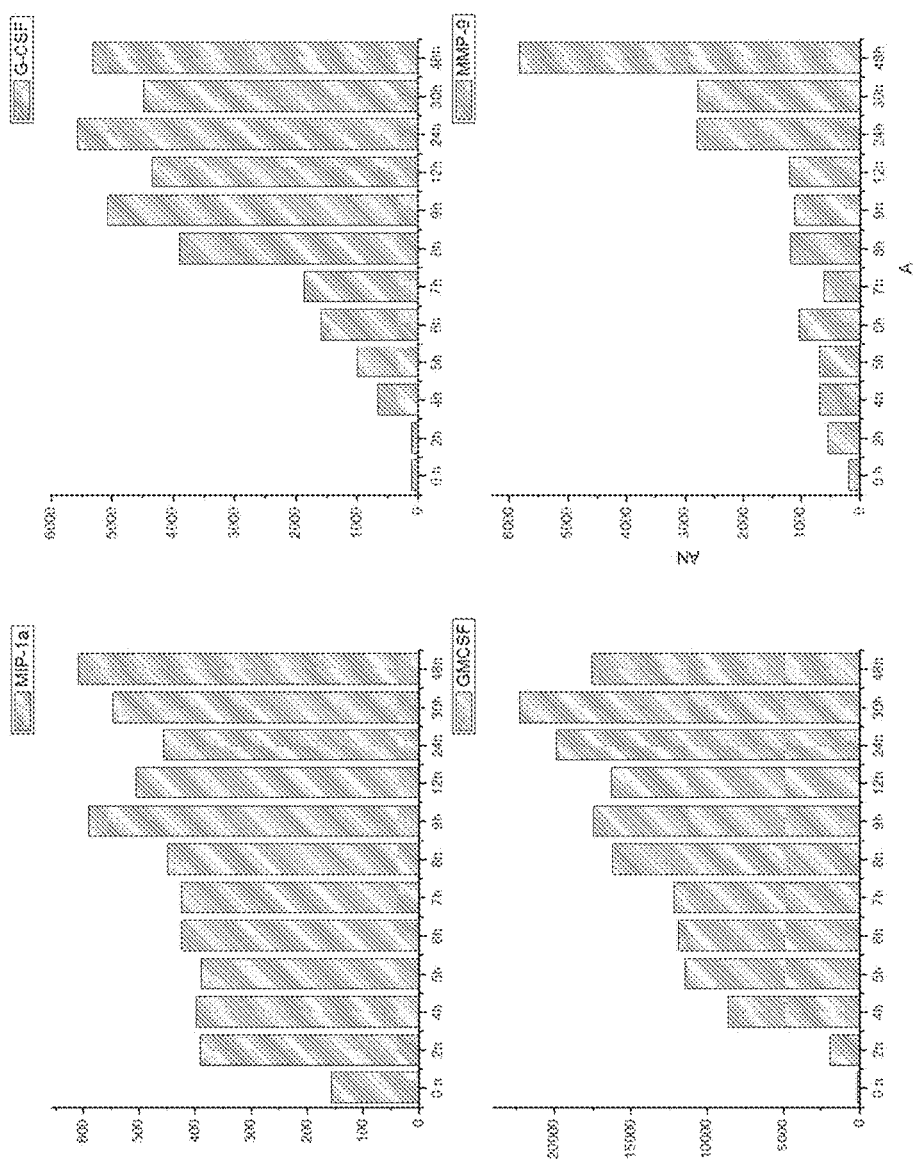

The results of single cell secretion analysis of macrophage response following stimulation of the TLR4 ligand, LPS is demonstrated in FIG. 45. Heatmaps show the comparison between untreated and LPS stimulated U937 monocyte derived macrophage protein secretion profiles (FIG. 45A). VISNE was used to visualize single cell secretion results (FIG. 45B). VISNE transforms high-dimensional single cell data into two dimensions, but still retains the high-dimensional structure of the original data. It visualizes individual cells similar to a scatter plot, in which all pairwise distances in high dimension are utilized to localize each cell's position in the plot. The X and Y axis are arbitrary numbers showing the 2D location. From this analysis it can be observed that untreated and LPS stimulated U937 single cells can be grouped into 3 subpopulations, based upon their protein secretions (in accordance with conventional cluster analysis (FIG. 54)). This is further illustrated in FIG. 45C, where individual proteins (MIF, IL-8, MCP-1, RANTES, MIP-1a, MIP-1b) secretion results with VISNE. It is clearly demonstrated that different proteins characterize the different subgroups of cells. For example, some proteins, such as IL-8, MIP-1b are sensitive to LPS stimulation, while some, such as MIF, are not.

Figures 56C, 56D, 56E:
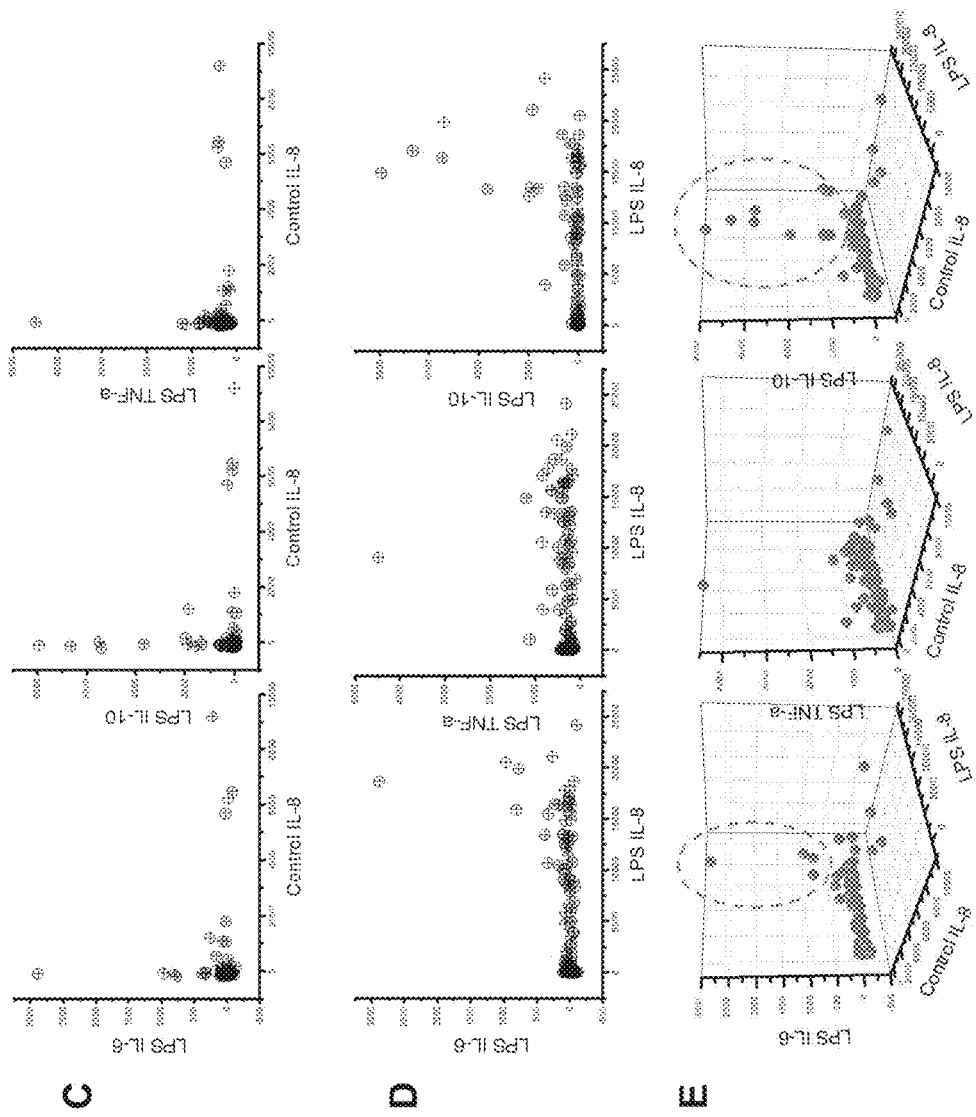
Figure 56F:
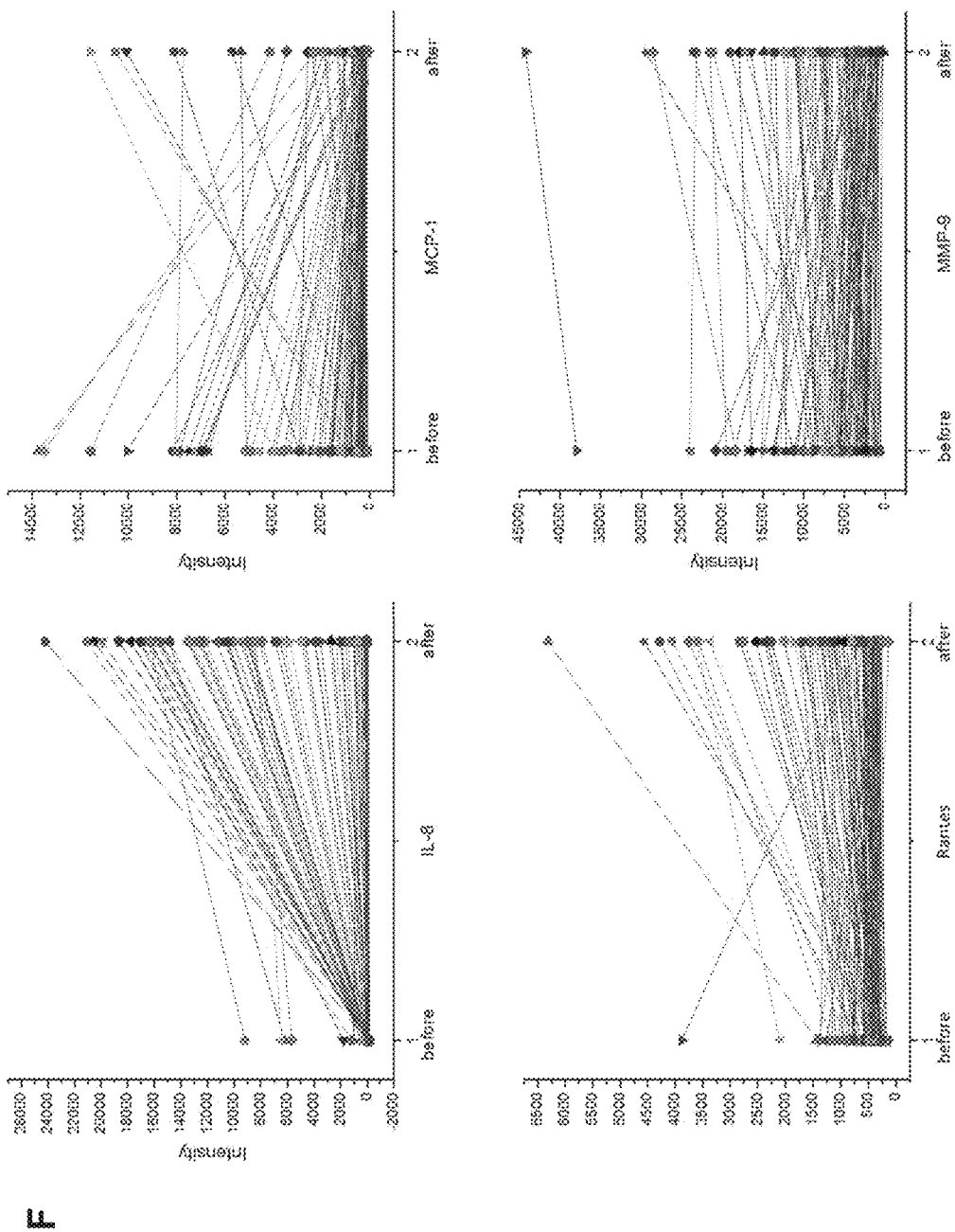

Analysis of identical cells before and after stimulation with LPS demonstrates how each individual cell may have a specific secretion profile. For example, FIG. 56 includes a series of plots demonstrating how individual cells respond to LPS stimulation. This data demonstrates that while secretion of some proteins is similar across cells, secretion of other proteins may vastly differ among the different single cells of the study population.

Figure 46A:
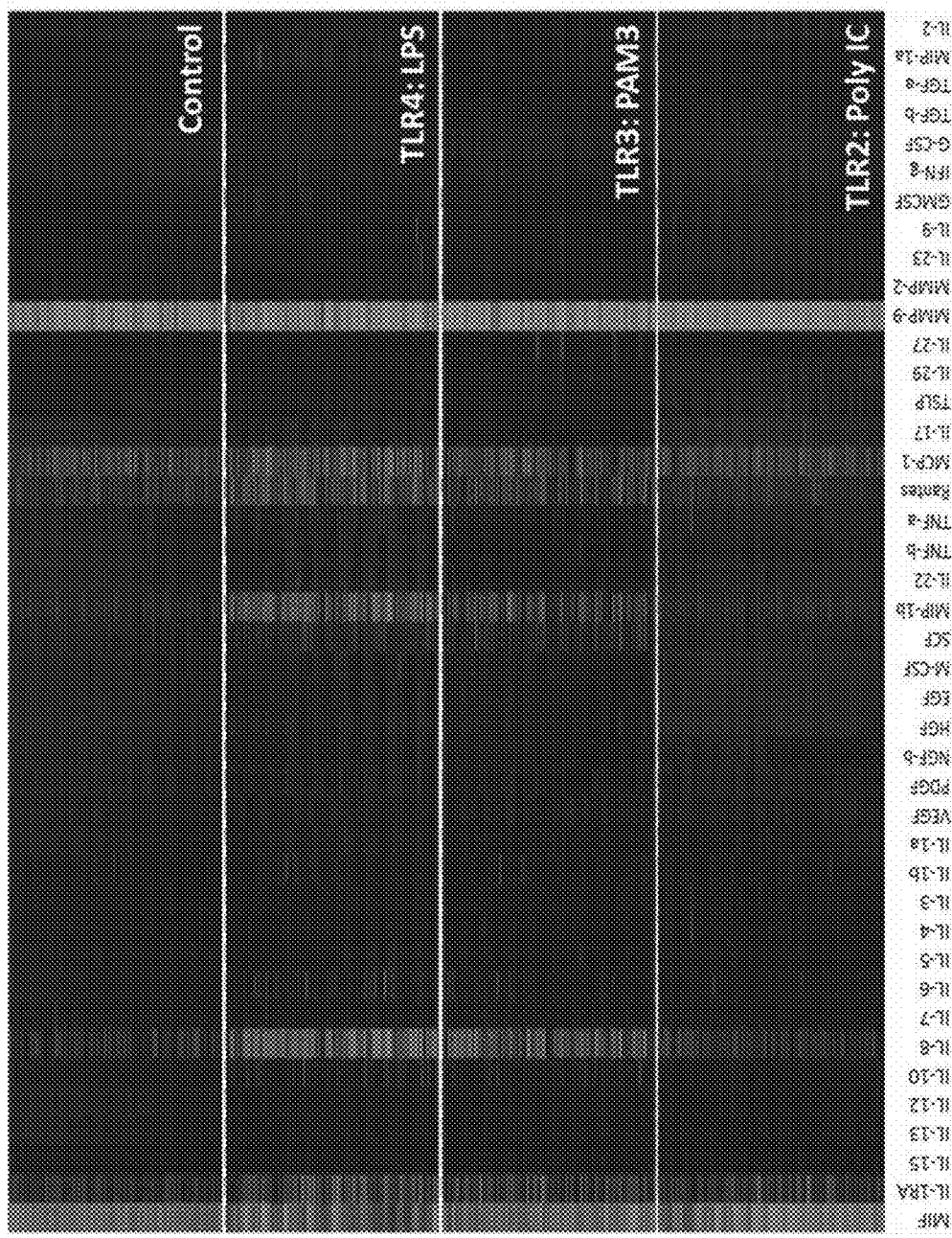
FIGS. 46A-46D depict the results of experiments demonstrating the macrophage response upon different TLR ligands (LPS, PAM3, poly IC) stimulation.
Figure 46B:
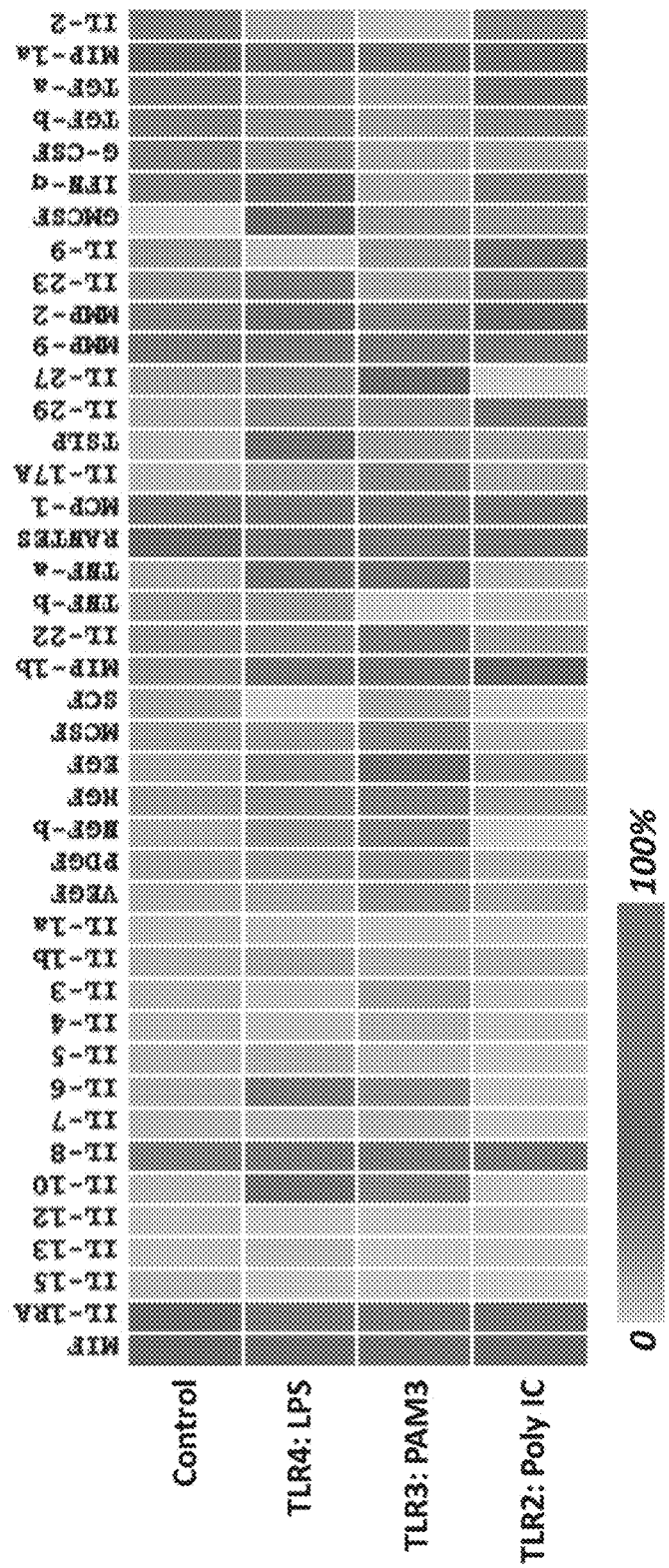
Figure 46C:
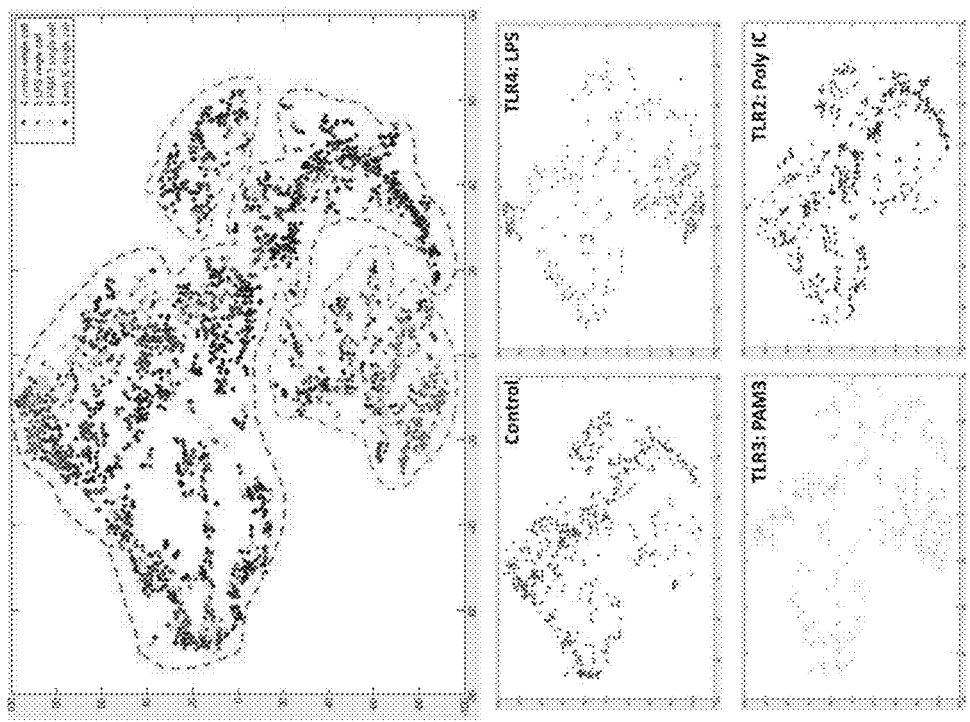
Figure 46D:
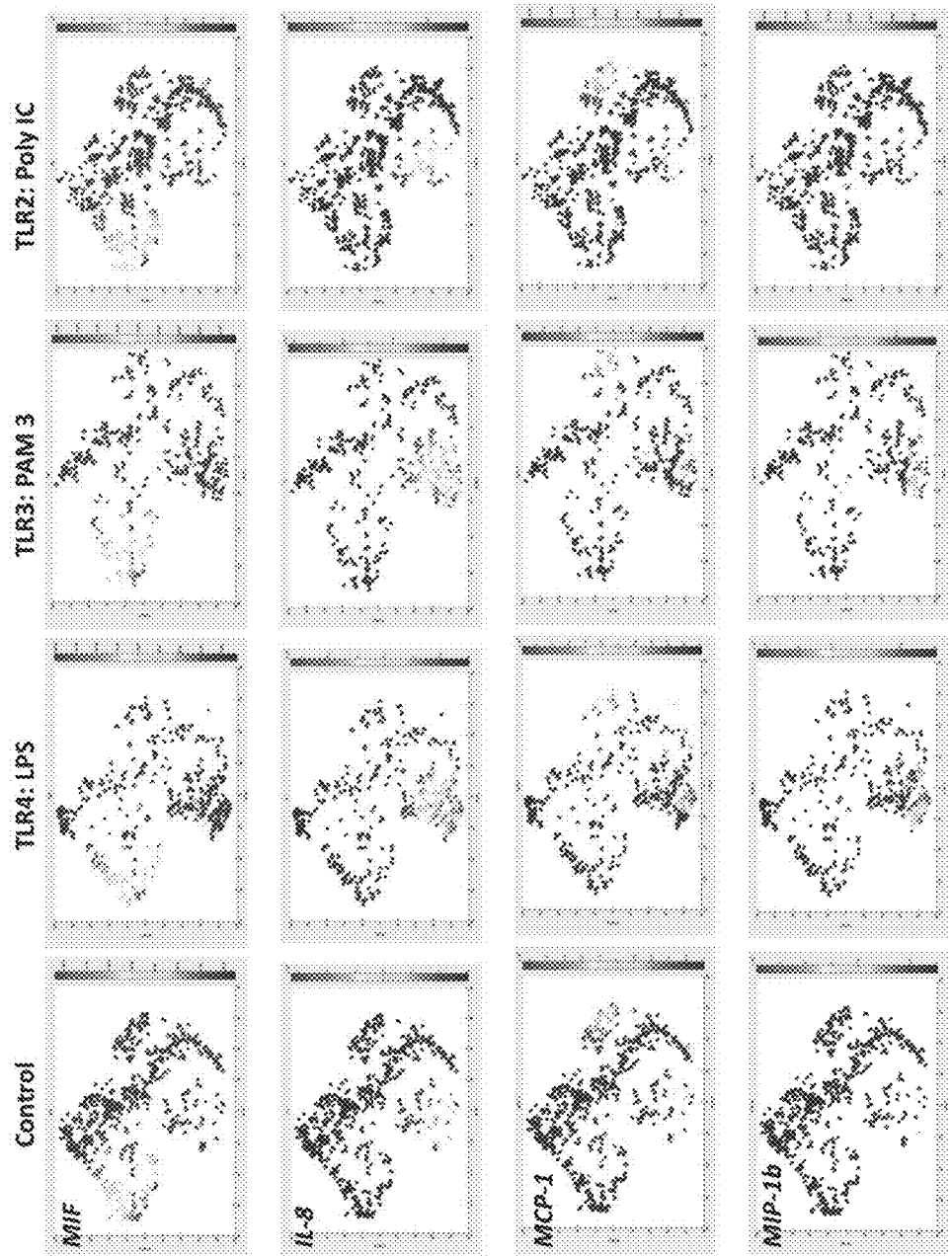

Experiments were performed to examine macrophage response to different TLR ligands (LPS, PAM3, or poly IC) stimulation. FIG. 46A depicts the heatmaps showing protein secretion profiles of untreated and stimulated (LPS, PAMP, or poly IC) U937 monocyte derived macrophage. Further, the frequency of cell secretion of each of the given proteins was analyzed under each condition (FIG. 46B). Single cell results were visualized with VISNE, from which it was observed that both untreated and stimulated single cells are grouped into 3 subpopulations based upon their secretions (FIG. 46C). This was further illustrated when observing the secretion of individual proteins (MIF, IL-8, MCP-1, and MIP-1b) with VISNE (FIG. 46D).

The presently described system provides for effective determination of cell secretion at the single cell level, which can identify important single cell differences within cell populations. The benefits of the present system are listed in FIG. 57. There are several differences in comparing the single cell secretion assay presented here and ICS. First, it is important to note that protein expression does not equal protein secretion. The present single cell assay measures the amount of protein secreted by a cell, whereas ICS measures the protein blocked within the cell. Further, during ICS, a Golgi blocker is used which may alter cell function, and is toxic to cells. Conversely the present single cell assay uses a physical barrier to block signals, which is non-toxic. Additionally, the present single cell assay uses a sandwich immunoassay format which provides greater specificity than ICS, since two different epitopes of the protein must be recognized in order to provide a signal in sandwich technique. Thus, detection threshold for a positive cell can be very different in these two systems.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variation.

What is claimed:

1. A device for multiplexed detection of molecules produced from a cell, the device comprising:
   a plurality of enclosed interfaces, wherein each enclosed interface comprises
   (a) a substrate containing at least ten spatially identifiable isolated features,
      wherein of the at least ten of the isolated features, at least two isolated features contain at least two immobilized capture antibodies per isolated feature, and
      wherein each immobilized capture antibody specifically recognizes a different protein of interest, and
   (b) a chamber configured to contain a cell and the at least ten spatially identifiable isolated features of (a).

2. The device of claim 1, wherein the chamber is a rectangle.

3. The device of claim 1, wherein the chamber is a microchamber.

4. The device of claim 1, wherein each isolated feature is separated from the next isolated feature by about 2-50 µm.

5. The device of claim 1, wherein the isolated features are arrayed with a pitch size of 50 µm.

6. The device of claim 1, wherein each isolated feature is 2-100 µm in width.

7. The device of claim 1, wherein the enclosed interfaces are arranged in an array format including parallel lines or dots.

8. The device of claim 1, wherein the isolated features are arranged in parallel within the enclosed interfaces.

9. The device of claim 3, wherein the device comprises 200 microchambers per $cm^2$ to 20,000 microchambers per $cm^2$.

10. The device of claim 3, wherein the device comprises 100 microchambers to 100,000 microchambers.

11. The device of claim 3, wherein each microchamber has a length of 10 µm to 2000 µm, a width of 10 µm to 100 µm, and a depth of 10 µm to 100 µm.

12. The device of claim 1, wherein each of the isolated features contains at least three immobilized capture antibodies.

13. The device of claim 1, wherein the isolated features are fabricated by a micro-scale printing technique.

14. The device of claim 13, wherein the micro-scale printing technique is microspotting or inkjet printing.

15. The device of claim 1, wherein the device comprises at least one cell within a chamber of at least one enclosed interface.

16. The device of claim 1, wherein the chamber comprises proteins secreted from the at least one cell.

17. The device of claim 16, wherein the proteins bind to one or more capture antibodies of at least one isolated feature of the substrate.

* * * * *